US012638445B2

(12) United States Patent
Bullington et al.

(10) Patent No.: US 12,638,445 B2
(45) **Date of Patent: *May 26, 2026**

(54) FLUID TRANSFER DEVICES WITH INTEGRATED FLOW-BASED ASSAY AND METHODS OF USING THE SAME

(71) Applicant: Magnolia Medical Technologies, Inc., Seattle, WA (US)

(72) Inventors: Gregory J. Bullington, Seattle, WA (US); Jay M. Miazga, Langley, WA (US); Shan E. Gaw, Seattle, WA (US); Paul E. Goldenbaum, San Antonio, TX (US); Dylan Guelig, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/243,540

(22) Filed: Sep. 7, 2023

(65) Prior Publication Data

US 2023/0417746 A1 Dec. 28, 2023

Related U.S. Application Data

(63) Continuation of application No. 17/119,732, filed on Dec. 11, 2020, now Pat. No. 11,789,017.

(Continued)

(51) Int. Cl.

| | |
|---|---|
| ***G01N 21/64*** | (2006.01) |
| ***B01L 3/00*** | (2006.01) |

(Continued)

(52) U.S. Cl.

CPC ...... *G01N 33/54388* (2021.08); *B01L 3/0217* (2013.01); *B01L 3/502715* (2013.01);

(Continued)

(58) Field of Classification Search

CPC ......... G01N 33/54388; G01N 33/5304; G01N 2333/72; G01N 2800/26; B01L 3/0217;

(Continued)

(56) References Cited

U.S. PATENT DOCUMENTS

| | | | |
|---|---|---|---|
| 2,674,265 | A | 4/1954 | Lee |
| 2,697,435 | A | 12/1954 | Benjamin |

(Continued)

FOREIGN PATENT DOCUMENTS

| | | | |
|---|---|---|---|
| AT | 310345 | B | 9/1973 |
| AT | E219383 | T1 | 7/2002 |

(Continued)

OTHER PUBLICATIONS

Arenas et al., "Asynchronous Testing of 2 Specimen-Diversion Devices to reduce Blood Culture Contamination: A Single-Site Product Supply Quality Improvement Project," J. Emergency Nursing, vol. 47, No. 2, pp. 256-264.e6 (Mar. 2021), 15 pages.

(Continued)

*Primary Examiner* — Jennifer Wecker
*Assistant Examiner* — Oyeleye Alexander Alabi
(74) *Attorney, Agent, or Firm* — COOLEY LLP

(57) ABSTRACT

A system includes a fluid transfer device and a lateral flow assay device. The fluid transfer device has an inlet fluidically coupleable to a bodily fluid source, an outlet fluidically coupleable to a sample reservoir, and a sequestration chamber configured to receive an initial volume of bodily fluid. The fluid transfer device can be transitioned between (1) a first state with the sequestration chamber in fluid communication with the inlet to receive the initial volume, (2) a second state with the outlet in fluid communication with the inlet to receive a subsequent flow of bodily fluid, and (3) a third state with the lateral flow assay device in fluid communication with the sequestration chamber to receive a (Continued)

portion of the initial volume of bodily fluid. The lateral flow assay device configured to provide an indication associated with a presence of a target analyte in the bodily fluid.

10 Claims, 15 Drawing Sheets

Related U.S. Application Data

(60) Provisional application No. 62/946,680, filed on Dec. 11, 2019.

(51) Int. Cl.

| | |
|---|---|
| ***B01L 3/02*** | (2006.01) |
| ***B82Y 5/00*** | (2011.01) |
| ***B82Y 30/00*** | (2011.01) |
| ***B82Y 40/00*** | (2011.01) |
| ***C07F 5/02*** | (2006.01) |
| ***C09B 57/00*** | (2006.01) |
| ***C09K 11/06*** | (2006.01) |
| ***G01N 1/30*** | (2006.01) |
| ***G01N 15/10*** | (2024.01) |
| ***G01N 15/1429*** | (2024.01) |
| ***G01N 27/626*** | (2021.01) |
| ***G01N 31/22*** | (2006.01) |
| ***G01N 33/483*** | (2006.01) |
| ***G01N 33/53*** | (2006.01) |
| ***G01N 33/543*** | (2006.01) |
| ***G01N 33/58*** | (2006.01) |
| ***G01N 33/68*** | (2006.01) |

(52) U.S. Cl.
CPC .. *G01N 33/5304* (2013.01); *B01L 2300/0819* (2013.01); *B01L 2400/0403* (2013.01)

(58) Field of Classification Search
CPC ....... B01L 3/502715; B01L 2300/0819; B01L 2400/0403; A61B 5/15003; A61B 5/150213; A61B 5/150221; A61B 5/150251; A61B 5/150755; A61B 5/157
See application file for complete search history.

(56) References Cited

U.S. PATENT DOCUMENTS

| | | | |
|---|---|---|---|
| 2,707,953 | A | 5/1955 | Ryan |
| 2,876,769 | A | 3/1959 | Cordova |
| 2,952,258 | A | 9/1960 | Chandler |
| 2,992,974 | A | 7/1961 | Belcove et al. |
| 3,013,557 | A | 12/1961 | Pallotta |
| 3,098,016 | A | 7/1963 | Sam et al. |
| 3,382,865 | A | 5/1968 | Worrall, Jr. |
| 3,405,706 | A | 10/1968 | Paul |
| 3,467,021 | A | 9/1969 | Green, Jr. |
| 3,467,095 | A | 9/1969 | Ross |
| 3,494,351 | A | 2/1970 | Horn |
| 3,494,352 | A | 2/1970 | Russo et al. |
| 3,577,980 | A | 5/1971 | Cohen |
| 3,596,652 | A | 8/1971 | Winkelman |
| 3,604,410 | A | 9/1971 | Whitacre |
| 3,635,798 | A | 1/1972 | Kirkham et al. |
| 3,640,267 | A | 2/1972 | Hurtig et al. |
| 3,648,684 | A | 3/1972 | Barnwell et al. |
| 3,650,093 | A | 3/1972 | Rosenberg |
| 3,680,558 | A | 8/1972 | Kapelowitz |
| 3,696,806 | A | 10/1972 | Sausse |
| 3,705,018 | A | 12/1972 | Taylor |
| 3,730,168 | A | 5/1973 | McWhorter |
| 3,741,197 | A | 6/1973 | Sanz et al. |
| 3,749,084 | A | 7/1973 | Cucchiara |
| 3,777,773 | A | 12/1973 | Tolbert |
| 3,779,383 | A | 12/1973 | Ayres |
| 3,803,810 | A | 4/1974 | Rosenberg |
| 3,817,240 | A | 6/1974 | Ayres |
| 3,831,602 | A | 8/1974 | Broadwin |
| 3,834,372 | A | 9/1974 | Turney |
| 3,835,835 | A | 9/1974 | Thompson et al. |
| 3,848,579 | A | 11/1974 | Villa |
| 3,848,581 | A | 11/1974 | Cinqualbre et al. |
| 3,859,998 | A | 1/1975 | Thomas et al. |
| 3,874,367 | A | 4/1975 | Ayres |
| 3,886,930 | A | 6/1975 | Ryan |
| 3,890,203 | A | 6/1975 | Mehl |
| 3,890,968 | A | 6/1975 | Pierce et al. |
| 3,937,211 | A | 2/1976 | Merten |
| 3,943,917 | A | 3/1976 | Johansen |
| 3,945,380 | A | 3/1976 | Dabney et al. |
| 3,960,139 | A | 6/1976 | Bailey |
| 3,978,846 | A | 9/1976 | Bailey |
| 3,996,923 | A | 12/1976 | Guerra |
| 4,056,101 | A | 11/1977 | Geissler et al. |
| 4,057,050 | A | 11/1977 | Sarstedt |
| 4,062,360 | A | 12/1977 | Bentley |
| 4,063,460 | A | 12/1977 | Svensson |
| 4,077,395 | A | 3/1978 | Woolner |
| 4,106,491 | A | 8/1978 | Guerra |
| 4,106,497 | A | 8/1978 | Percarpio |
| 4,133,304 | A | 1/1979 | Bailey |
| 4,133,863 | A | 1/1979 | Koenig |
| 4,150,089 | A | 4/1979 | Linet |
| 4,154,229 | A | 5/1979 | Nugent |
| 4,166,450 | A | 9/1979 | Abramson |
| 4,190,426 | A | 2/1980 | Ruschke |
| 4,193,400 | A | 3/1980 | Loveless et al. |
| 4,202,764 | A | 5/1980 | Afflerbaugh et al. |
| 4,206,282 | A | 6/1980 | Hochstein |
| 4,207,870 | A | 6/1980 | Eldridge |
| 4,210,173 | A | 7/1980 | Choksi et al. |
| 4,212,308 | A | 7/1980 | Percarpio |
| 4,226,236 | A | 10/1980 | Genese |
| 4,238,207 | A | 12/1980 | Ruschke |
| 4,257,416 | A | 3/1981 | Prager |
| 4,275,730 | A | 6/1981 | Hussein |
| 4,298,358 | A | 11/1981 | Ruschke |
| 4,312,362 | A | 1/1982 | Kaufman |
| 4,317,456 | A | 3/1982 | Percarpio |
| 4,327,746 | A | 5/1982 | Feaster |
| 4,340,067 | A | 7/1982 | Rattenborg |
| 4,340,068 | A | 7/1982 | Kaufman |
| 4,349,035 | A | 9/1982 | Thomas et al. |
| 4,354,507 | A | 10/1982 | Raitto |
| 4,370,987 | A | 2/1983 | Bazell et al. |
| 4,373,535 | A | 2/1983 | Martell |
| 4,398,544 | A | 8/1983 | Nugent et al. |
| 4,411,275 | A | 10/1983 | Raitto |
| 4,412,548 | A | 11/1983 | Hoch |
| 4,416,290 | A | 11/1983 | Lutkowski |
| 4,416,291 | A | 11/1983 | Kaufman |
| 4,425,235 | A | 1/1984 | Cornell et al. |
| 4,436,098 | A | 3/1984 | Kaufman |
| 4,444,203 | A | 4/1984 | Engelman |
| 4,459,997 | A | 7/1984 | Sarstedt |
| 4,496,458 | A | 1/1985 | Lee |
| 4,509,534 | A | 4/1985 | Tassin, Jr. |
| 4,551,131 | A | 11/1985 | Miles et al. |
| 4,581,014 | A | 4/1986 | Millerd et al. |
| 4,608,996 | A | 9/1986 | Brown |
| 4,626,248 | A | 12/1986 | Scheller |
| 4,654,027 | A | 3/1987 | Dragan et al. |
| 4,657,027 | A | 4/1987 | Paulsen |
| 4,657,160 | A | 4/1987 | Woods et al. |
| 4,673,386 | A | 6/1987 | Gordon |
| 4,676,256 | A | 6/1987 | Golden |
| 4,679,571 | A | 7/1987 | Frankel et al. |
| 4,690,154 | A | 9/1987 | Woodford et al. |
| 4,699,612 | A | 10/1987 | Hamacher |
| 4,703,763 | A | 11/1987 | McAlister et al. |
| 4,705,497 | A | 11/1987 | Shitaokoshi et al. |
| 4,714,461 | A | 12/1987 | Gabel |
| 4,715,854 | A | 12/1987 | Vaillancourt |

(56) References Cited

U.S. PATENT DOCUMENTS

| | | | |
|---|---|---|---|
| 4,772,273 | A | 9/1988 | Alchas |
| 4,820,287 | A | 4/1989 | Leonard |
| 4,838,855 | A | 6/1989 | Lynn |
| 4,865,583 | A | 9/1989 | Tu |
| 4,879,098 | A | 11/1989 | Oberhardt et al. |
| 4,886,072 | A | 12/1989 | Percarpio et al. |
| 4,890,627 | A | 1/1990 | Haber et al. |
| 4,904,240 | A | 2/1990 | Hoover |
| 4,936,315 | A | 6/1990 | Lineback |
| 4,980,297 | A | 12/1990 | Haynes et al. |
| 4,988,339 | A | 1/1991 | Vadher |
| 5,009,847 | A | 4/1991 | Solomons |
| 5,027,827 | A | 7/1991 | Cody et al. |
| 5,032,116 | A | 7/1991 | Peterson et al. |
| 5,032,288 | A | 7/1991 | Columbus et al. |
| 5,035,688 | A | 7/1991 | Inui |
| 5,045,185 | A | 9/1991 | Ohnaka et al. |
| 5,052,403 | A | 10/1991 | Haber et al. |
| 5,054,498 | A | 10/1991 | Melet |
| 5,066,284 | A | 11/1991 | Mersch et al. |
| 5,084,034 | A | 1/1992 | Zanotti |
| 5,097,842 | A | 3/1992 | Bonn |
| 5,100,394 | A | 3/1992 | Dudar et al. |
| 5,108,927 | A | 4/1992 | Dorn |
| 5,116,323 | A | 5/1992 | Kreuzer et al. |
| 5,122,129 | A | 6/1992 | Olson et al. |
| 5,126,054 | A | 6/1992 | Matkovich |
| 5,135,489 | A | 8/1992 | Jepson et al. |
| 5,147,329 | A | 9/1992 | Brannon |
| 5,208,160 | A | 5/1993 | Kikyotani et al. |
| 5,222,502 | A | 6/1993 | Kurose |
| 5,269,317 | A | 12/1993 | Bennett |
| 5,286,279 | A | 2/1994 | Wu |
| 5,330,464 | A | 7/1994 | Mathias et al. |
| 5,334,162 | A | 8/1994 | Harris |
| 5,354,537 | A | 10/1994 | Moreno |
| 5,360,011 | A | 11/1994 | McCallister |
| 5,372,143 | A | 12/1994 | Bernes et al. |
| 5,395,339 | A | 3/1995 | Talonn et al. |
| 5,417,673 | A | 5/1995 | Gordon |
| 5,429,610 | A | 7/1995 | Vaillancourt |
| 5,431,811 | A | 7/1995 | Tusini et al. |
| 5,439,022 | A | 8/1995 | Summers et al. |
| 5,439,450 | A | 8/1995 | Haedt |
| 5,450,856 | A | 9/1995 | Norris |
| 5,451,321 | A | 9/1995 | Matkovich |
| 5,454,786 | A | 10/1995 | Harris |
| 5,466,228 | A | 11/1995 | Evans |
| 5,472,605 | A | 12/1995 | Zuk, Jr. |
| 5,485,854 | A | 1/1996 | Hollister |
| 5,507,299 | A | 4/1996 | Roland |
| 5,520,193 | A | 5/1996 | Suzuki et al. |
| 5,522,804 | A | 6/1996 | Lynn |
| 5,573,510 | A | 11/1996 | Isaacson |
| 5,573,951 | A | 11/1996 | Gombrich et al. |
| 5,575,777 | A | 11/1996 | Cover et al. |
| 5,577,513 | A | 11/1996 | Van Vlasselaer |
| 5,603,700 | A | 2/1997 | Daneshvar |
| 5,632,906 | A | 5/1997 | Ishida et al. |
| 5,634,893 | A | 6/1997 | Rishton |
| 5,649,912 | A | 7/1997 | Peterson |
| 5,658,271 | A | 8/1997 | Loubser |
| 5,685,846 | A | 11/1997 | Michaels, Jr. |
| 5,691,486 | A | 11/1997 | Behringer et al. |
| 5,749,857 | A | 5/1998 | Cuppy |
| 5,759,160 | A | 6/1998 | Neese et al. |
| 5,762,633 | A | 6/1998 | Whisson |
| 5,772,608 | A | 6/1998 | Dhas |
| 5,785,682 | A | 7/1998 | Grabenkort |
| 5,811,658 | A | 9/1998 | Van Driel et al. |
| 5,824,001 | A | 10/1998 | Erskine |
| 5,857,983 | A | 1/1999 | Douglas et al. |
| 5,865,803 | A | 2/1999 | Major |
| 5,865,812 | A | 2/1999 | Correia |
| 5,871,699 | A | 2/1999 | Ruggeri |
| 5,873,841 | A | 2/1999 | Brannon |
| 5,876,926 | A | 3/1999 | Beecham |
| 5,882,318 | A | 3/1999 | Boyde |
| 5,911,705 | A | 6/1999 | Howell |
| 5,922,551 | A | 7/1999 | Durbin et al. |
| RE36,273 | E | 8/1999 | Brannon |
| 5,947,932 | A | 9/1999 | Desecki et al. |
| 5,961,472 | A | 10/1999 | Swendson et al. |
| 5,971,956 | A | 10/1999 | Epstein |
| 5,980,830 | A | 11/1999 | Savage et al. |
| 6,001,307 | A | 12/1999 | Naka et al. |
| 6,010,633 | A | 1/2000 | Zuk, Jr. et al. |
| 6,013,037 | A | 1/2000 | Brannon |
| 6,016,712 | A | 1/2000 | Warden et al. |
| 6,050,957 | A | 4/2000 | Desch |
| 6,103,271 | A | 8/2000 | Morrison et al. |
| 6,106,509 | A | 8/2000 | Loubser |
| 6,126,643 | A | 10/2000 | Vaillancouert |
| 6,159,164 | A | 12/2000 | Neese et al. |
| 6,171,493 | B1 | 1/2001 | Zia et al. |
| 6,190,855 | B1 | 2/2001 | Herman et al. |
| 6,210,909 | B1 | 4/2001 | Guirguis |
| 6,224,561 | B1 | 5/2001 | Swendson et al. |
| 6,254,581 | B1 | 7/2001 | Scott |
| 6,296,020 | B1 | 10/2001 | McNeely et al. |
| 6,299,131 | B1 | 10/2001 | Ryan |
| 6,306,614 | B1 | 10/2001 | Romaschin et al. |
| 6,325,975 | B1 | 12/2001 | Naka et al. |
| 6,328,726 | B1 | 12/2001 | Ishida et al. |
| 6,355,023 | B1 | 3/2002 | Roth et al. |
| 6,364,847 | B1 | 4/2002 | Shulze et al. |
| 6,364,890 | B1 | 4/2002 | Lum et al. |
| 6,368,306 | B1 | 4/2002 | Koska |
| 6,387,086 | B2 | 5/2002 | Mathias et al. |
| 6,398,743 | B1 | 6/2002 | Halseth et al. |
| 6,403,381 | B1 | 6/2002 | Mann et al. |
| 6,440,725 | B1 | 8/2002 | Pourahmadi et al. |
| 6,478,775 | B1 | 11/2002 | Galt et al. |
| 6,506,182 | B2 | 1/2003 | Estabrook et al. |
| 6,511,439 | B1 | 1/2003 | Tabata et al. |
| 6,520,948 | B1 | 2/2003 | Mathias et al. |
| 6,569,117 | B1 | 5/2003 | Ziv et al. |
| 6,592,555 | B1 | 7/2003 | Wen-Pi et al. |
| 6,592,613 | B1 | 7/2003 | Ishida et al. |
| 6,626,884 | B1 | 9/2003 | Dillon et al. |
| 6,629,959 | B2 | 10/2003 | Kuracina et al. |
| 6,638,252 | B2 | 10/2003 | Moulton et al. |
| 6,638,263 | B1 | 10/2003 | Theeuwes et al. |
| 6,648,835 | B1 | 11/2003 | Shemesh |
| 6,692,479 | B2 | 2/2004 | Kraus et al. |
| 6,695,004 | B1 | 2/2004 | Raybuck |
| 6,712,963 | B2 | 3/2004 | Schick |
| 6,716,187 | B1 | 4/2004 | Jorgensen et al. |
| 6,716,396 | B1 | 4/2004 | Anderson et al. |
| 6,733,433 | B1 | 5/2004 | Fell |
| 6,736,783 | B2 | 5/2004 | Blake et al. |
| 6,746,420 | B1 | 6/2004 | Prestidge et al. |
| 6,772,513 | B1 | 8/2004 | Frye-Mason et al. |
| 6,843,775 | B2 | 1/2005 | Hyun |
| 6,860,871 | B2 | 3/2005 | Kuracina et al. |
| 6,905,483 | B2 | 6/2005 | Newby et al. |
| 6,913,580 | B2 | 7/2005 | Stone |
| 6,945,948 | B2 | 9/2005 | Bainbridge et al. |
| 6,979,323 | B2 | 12/2005 | Rogers et al. |
| 7,044,941 | B2 | 5/2006 | Mathias et al. |
| 7,052,603 | B2 | 5/2006 | Schick |
| 7,055,401 | B2 | 6/2006 | Prybella et al. |
| 7,087,047 | B2 | 8/2006 | Kraus et al. |
| 7,141,097 | B2 | 11/2006 | Leahey |
| 7,241,281 | B2 | 7/2007 | Coelho et al. |
| 7,261,707 | B2 | 8/2007 | Frezza et al. |
| 7,264,608 | B2 | 9/2007 | Bischof et al. |
| 7,306,736 | B2 | 12/2007 | Collins et al. |
| 7,314,452 | B2 | 1/2008 | Madonia |
| 7,316,662 | B2 | 1/2008 | Delnevo et al. |
| 7,335,188 | B2 | 2/2008 | Graf |
| 7,351,228 | B2 | 4/2008 | Keane et al. |
| 7,384,416 | B2 | 6/2008 | Goudaliez et al. |
| 7,435,231 | B2 | 10/2008 | Mathias et al. |

(56) References Cited

U.S. PATENT DOCUMENTS 7,461,671 B2 12/2008 Ehwald et al.
7,479,131 B2 1/2009 Mathias et al.
7,544,324 B2 6/2009 Tung et al.
7,614,857 B2 11/2009 Fuechslin et al.
7,615,033 B2 11/2009 Leong
7,618,407 B2 11/2009 Demay et al.
7,648,491 B2 1/2010 Rogers
7,666,166 B1 2/2010 Emmert et al.
7,744,573 B2 6/2010 Gordon et al.
7,766,879 B2 8/2010 Tan et al.
7,896,817 B2 3/2011 Garrison
7,914,508 B2 3/2011 Engstrom
7,923,053 B2 4/2011 Kitching et al.
7,963,950 B2 6/2011 Madonia
8,070,725 B2 12/2011 Christensen
8,109,157 B2 2/2012 Kanayama et al.
RE43,283 E 3/2012 Ishida et al.
8,197,420 B2 6/2012 Patton
8,206,318 B2 6/2012 Uchiyama et al.
8,231,546 B2 7/2012 Patton
8,282,605 B2 10/2012 Tan et al.
8,287,499 B2 10/2012 Miyasaka
8,337,418 B2 12/2012 Patton
8,349,254 B2 1/2013 Hoshino et al.
8,356,644 B2 1/2013 Chong et al.
8,377,040 B2 2/2013 Burkholz et al.
8,382,712 B2 2/2013 Kim
8,383,044 B2 2/2013 Davis et al.
8,412,300 B2 4/2013 Sonderegger
8,523,826 B2 9/2013 Layton, Jr.
8,535,241 B2 9/2013 Bullington et al.
8,540,663 B2 9/2013 Davey et al.
8,568,371 B2 10/2013 Siopes et al.
8,574,203 B2 11/2013 Stout et al.
8,603,009 B2 12/2013 Tan et al.
8,647,286 B2 2/2014 Patton
8,679,063 B2 3/2014 Stout et al.
8,747,779 B2 6/2014 Sprague et al.
8,772,046 B2 7/2014 Fraden et al.
8,795,198 B2 8/2014 Tan et al.
8,808,202 B2 8/2014 Brancazio
8,827,958 B2 9/2014 Bierman et al.
8,864,684 B2 10/2014 Bullington et al.
8,876,734 B2 11/2014 Patton
8,992,505 B2 3/2015 Thorne, Jr. et al.
9,022,950 B2 5/2015 Bullington et al.
9,022,951 B2 5/2015 Bullington et al.
9,060,724 B2 6/2015 Bullington et al.
9,060,725 B2 6/2015 Bullington et al.
9,138,572 B2 9/2015 Zeytoonian et al.
9,149,576 B2 10/2015 Bullington et al.
9,155,495 B2 10/2015 Bullington et al.
9,204,864 B2 12/2015 Bullington et al.
9,205,198 B2 12/2015 Py
9,233,208 B2 1/2016 Tekeste
RE45,896 E 2/2016 Stout et al.
9,314,201 B2 4/2016 Burkholz et al.
9,320,459 B2 4/2016 Chin et al.
9,820,682 B2 11/2017 Rogers et al.
9,855,001 B2 1/2018 Patton
9,855,002 B2 1/2018 Patton
9,855,386 B2 1/2018 Close et al.
9,861,306 B2 1/2018 Patton
9,872,645 B2 1/2018 Patton
9,877,674 B2 1/2018 Holmes et al.
9,877,675 B2 1/2018 Baid
9,895,092 B2 2/2018 Burkholz
9,931,466 B2 4/2018 Bullington et al.
9,950,084 B2 4/2018 Bullington et al.
9,962,489 B2 5/2018 Hopkins
9,999,383 B2 6/2018 Bullington et al.
10,010,282 B2 7/2018 Rogers et al.
10,022,079 B2 7/2018 Hopkins
10,022,530 B2 7/2018 Tekeste
10,028,687 B2 7/2018 Patton
10,028,688 B2 7/2018 Patton
10,028,689 B2 7/2018 Patton
10,039,483 B2 8/2018 Bullington et al.
10,045,724 B2 8/2018 Patton
10,052,053 B2 8/2018 Patton
10,080,516 B2 9/2018 Ellis et al.
10,086,142 B2 10/2018 Tekeste
10,143,412 B2 12/2018 Rogers et al.
10,143,413 B2 12/2018 Garrett et al.
10,206,613 B2 2/2019 Bullington et al.
10,220,139 B2 3/2019 Bullington et al.
10,238,326 B2 3/2019 Gil et al.
10,251,590 B2 4/2019 Bullington et al.
10,265,007 B2 4/2019 Bullington et al.
10,292,633 B2 5/2019 Bullington et al.
10,299,713 B2 5/2019 Patton
10,369,285 B2 8/2019 Hopkins
10,433,779 B2 10/2019 Bullington et al.
10,463,792 B2 11/2019 Hopkins
10,596,315 B2 3/2020 Bullington et al.
10,624,977 B2 4/2020 Bullington et al.
10,736,554 B2 8/2020 Bullington et al.
10,772,548 B2 9/2020 Bullington et al.
10,813,579 B2 10/2020 Baid
10,827,964 B2 11/2020 Rogers et al.
10,856,791 B2 12/2020 McHale et al.
10,881,343 B2 1/2021 Bullington et al.
10,888,262 B2 1/2021 Russ et al.
10,912,506 B2 2/2021 Bullington et al.
D923,171 S 6/2021 Miazga
11,076,787 B2 8/2021 Bullington et al.
11,116,904 B2 9/2021 Hopkins
11,167,085 B2 11/2021 Hopkins
11,234,626 B2 2/2022 Bullington et al.
11,253,649 B2 2/2022 Hopkins
11,259,727 B2 3/2022 Bullington et al.
11,311,218 B2 4/2022 Bullington et al.
11,317,838 B2 5/2022 Bullington et al.
11,318,459 B2 5/2022 Shi et al.
11,395,611 B2 7/2022 Bullington et al.
11,395,612 B2 7/2022 Bullington et al.
11,419,531 B2 8/2022 Bullington et al.
11,529,081 B2 12/2022 Bullington et al.
11,589,786 B2 2/2023 Bullington et al.
11,607,159 B2 3/2023 Bullington et al.
11,653,863 B2 5/2023 Bullington et al.
11,660,030 B2 5/2023 Bullington et al.
11,737,693 B2 8/2023 Bullington et al.
11,786,155 B2 10/2023 Bullington et al.
11,789,017 B2 10/2023 Bullington et al.
11,819,329 B2 11/2023 Bullington et al.
11,857,321 B2 1/2024 Bullington et al.
11,890,452 B2 2/2024 Bullington et al.
11,903,709 B2 2/2024 Bullington et al.
11,903,710 B2 2/2024 Bullington et al.
11,998,332 B2 6/2024 Bullington et al.
12,083,234 B2 9/2024 Bullington et al.
12,133,968 B2 11/2024 Bullington et al.
12,138,052 B1 11/2024 Rogers et al.
12,150,763 B2 11/2024 Bullington et al.
12,186,080 B2 1/2025 Bullington et al.
12,193,816 B2 1/2025 Bullington et al.
12,290,363 B2 5/2025 Bullington et al.
12,471,815 B2 11/2025 Bullington et al.
12,471,816 B2 11/2025 Bullington et al.
12,478,300 B2 11/2025 Bullington et al.
12,478,301 B2 11/2025 Bullington et al.
2001/0031932 A1* 10/2001 Blake ............... A61B 5/150503
600/573
2001/0039058 A1 11/2001 Iheme et al.
2002/0002349 A1 1/2002 Flaherty et al.
2002/0004647 A1 1/2002 Leong
2002/0107469 A1 8/2002 Bolan et al.
2002/0183651 A1 12/2002 Hyun
2002/0193751 A1 12/2002 Theeuwes et al.
2003/0013991 A1 1/2003 Stone
2003/0055381 A1 3/2003 Wilkinson
2003/0069543 A1 4/2003 Carpenter et al.
2003/0105414 A1 6/2003 Leong

(56) References Cited

U.S. PATENT DOCUMENTS

2003/0208151 A1 11/2003 Kraus et al.
2004/0000309 A1 1/2004 Alston
2004/0009542 A1 1/2004 Dumont et al.
2004/0010228 A1 1/2004 Swenson et al.
2004/0054283 A1 3/2004 Corey et al.
2004/0054333 A1 3/2004 Theeuwes et al.
2004/0073171 A1 4/2004 Rogers et al.
2004/0124389 A1 7/2004 Phillips
2004/0127816 A1 7/2004 Galvao
2004/0147855 A1 7/2004 Marsden
2005/0004524 A1 1/2005 Newby et al.
2005/0010136 A1 1/2005 Restelli et al.
2005/0054949 A1 3/2005 McKinnon et al.
2005/0082218 A1 4/2005 Verri et al.
2005/0148993 A1 7/2005 Mathias et al.
2005/0154368 A1 7/2005 Lim et al.
2005/0161112 A1 7/2005 Ehwald et al.
2005/0199077 A1 9/2005 Prybella et al.
2005/0240161 A1 10/2005 Crawford
2005/0245885 A1 11/2005 Brown
2005/0273019 A1 12/2005 Conway et al.
2005/0277848 A1 12/2005 Graf
2005/0281713 A1 12/2005 Hampsch et al.
2006/0009713 A1 1/2006 Flaherty
2006/0018790 A1 1/2006 Naka et al.
2006/0111667 A1 5/2006 Matsuura et al.
2006/0155212 A1 7/2006 Madonia
2006/0251622 A1 11/2006 Suzuki et al.
2006/0287639 A1 12/2006 Sharp
2007/0083162 A1 4/2007 O'Reagan et al.
2007/0088279 A1 4/2007 Shue et al.
2007/0100250 A1 5/2007 Kline
2007/0119508 A1 5/2007 West et al.
2007/0172389 A1* 7/2007 Wilding .................... B01L 7/52
422/400
2007/0191716 A1 8/2007 Goldberger et al.
2007/0287948 A1 12/2007 Sakiewicz
2008/0086085 A1 4/2008 Brown
2008/0108954 A1 5/2008 Mathias et al.
2008/0114304 A1 5/2008 Nalesso et al.
2008/0145933 A1 6/2008 Patton
2008/0167577 A1 7/2008 Weilbacher et al.
2008/0185056 A1 8/2008 Diodati et al.
2008/0200837 A1 8/2008 Frazier et al.
2008/0254471 A1 10/2008 Bordano
2008/0255523 A1 10/2008 Grinberg
2008/0268514 A1* 10/2008 Muller ..................... C12N 1/04
435/235.1
2008/0312576 A1 12/2008 McKinnon et al.
2008/0319346 A1 12/2008 Crawford et al.
2009/0076441 A1 3/2009 Sebban
2009/0173685 A1 7/2009 Imai et al.
2009/0177117 A1 7/2009 Amano et al.
2009/0192447 A1 7/2009 Andersen et al.
2009/0215159 A1 8/2009 Kirby
2009/0227896 A1 9/2009 Alvin Tan et al.
2009/0301317 A1 12/2009 Andrews
2009/0306601 A1 12/2009 Shaw et al.
2010/0010372 A1 1/2010 Brown et al.
2010/0042048 A1 2/2010 Christensen
2010/0057004 A1 3/2010 Christensen et al.
2010/0094171 A1 4/2010 Conway et al.
2010/0152681 A1 6/2010 Mathias
2010/0185134 A1 7/2010 Houwen et al.
2010/0234768 A1 9/2010 Uchiyama et al.
2010/0240964 A1 9/2010 Sterling et al.
2010/0252118 A1 10/2010 Fraden et al.
2010/0255589 A1 10/2010 Saiki et al.
2010/0268118 A1 10/2010 Schweiger
2010/0286513 A1 11/2010 Pollard, Jr. et al.
2010/0298671 A1 11/2010 Asakura et al.
2011/0009717 A1 1/2011 Davis et al.
2011/0046602 A1 2/2011 Grimm et al.
2011/0092856 A1 4/2011 Freeman et al.
2011/0125058 A1 5/2011 Levinson et al.
2011/0178427 A1 7/2011 Tan et al.
2011/0198221 A1 8/2011 Angelescu
2011/0288441 A1 11/2011 Taguchi
2011/0306856 A1 12/2011 Rule et al.
2011/0306899 A1 12/2011 Brown et al.
2011/0313318 A1 12/2011 Rule et al.
2011/0319859 A1 12/2011 Zeytoonian et al.
2012/0004619 A1 1/2012 Stephens et al.
2012/0016266 A1 1/2012 Burkholz
2012/0017999 A1 1/2012 Velschow
2012/0022404 A1 1/2012 Fojtik
2012/0029494 A1 2/2012 Wittenberger et al.
2012/0035540 A1 2/2012 Ferren et al.
2012/0095367 A1 4/2012 Patton
2012/0123297 A1 5/2012 Brancazio
2012/0215131 A1 8/2012 Patton
2012/0226239 A1 9/2012 Green
2012/0245042 A1 9/2012 Liu et al.
2012/0265099 A1 10/2012 Goodnow, II et al.
2012/0265128 A1 10/2012 Kolln
2012/0277697 A1 11/2012 Haghgooie et al.
2012/0323142 A1 12/2012 Allen et al.
2013/0023792 A1 1/2013 Markey et al.
2013/0079604 A1 3/2013 Patton
2013/0085514 A1 4/2013 Lee et al.
2013/0116599 A1 5/2013 Bullington et al.
2013/0158506 A1 6/2013 Harris et al.
2013/0289420 A1 10/2013 Pfeiffer et al.
2013/0295602 A1 11/2013 Fowler et al.
2013/0317391 A1 11/2013 Bullington et al.
2014/0008366 A1 1/2014 Genosar
2014/0039348 A1 2/2014 Bullington et al.
2014/0051062 A1 2/2014 Vanapalli et al.
2014/0066880 A1 3/2014 Prince et al.
2014/0081172 A1 3/2014 Patton
2014/0107564 A1 4/2014 Bullington et al.
2014/0124542 A1 5/2014 Kojima et al.
2014/0128775 A1* 5/2014 Andreae ................ A61B 5/153
600/581
2014/0155781 A1 6/2014 Bullington et al.
2014/0155782 A1 6/2014 Bullington et al.
2014/0163419 A1 6/2014 Bullington et al.
2014/0188002 A1 7/2014 Close et al.
2014/0208978 A1 7/2014 Sunder et al.
2014/0221873 A1 8/2014 Hayakawa et al.
2014/0276039 A1 9/2014 Cowan et al.
2014/0305196 A1 10/2014 Ellis et al.
2014/0336536 A1 11/2014 Brancazio
2015/0011847 A1 1/2015 Hayden
2015/0011910 A1 1/2015 Bullington et al.
2015/0011911 A1 1/2015 Bullington et al.
2015/0018715 A1 1/2015 Walterspiel
2015/0025454 A1 1/2015 Wetzel et al.
2015/0025455 A1 1/2015 Shetty et al.
2015/0025456 A1 1/2015 Shetty et al.
2015/0073304 A1 3/2015 Millerd
2015/0073348 A1 3/2015 Bullington et al.
2015/0094615 A1 4/2015 Patton
2015/0099996 A1 4/2015 Bullington et al.
2015/0111216 A1 4/2015 Delahunt et al.
2015/0151298 A1 6/2015 Hobbs et al.
2015/0257691 A1 9/2015 Bullington et al.
2015/0314105 A1 11/2015 Gasparyan et al.
2015/0342510 A1 12/2015 Bullington et al.
2015/0351678 A1 12/2015 Bullington et al.
2015/0351679 A1 12/2015 Bullington et al.
2015/0359473 A1 12/2015 Garrett et al.
2015/0367069 A1 12/2015 Bullington et al.
2016/0008579 A1 1/2016 Burkholz et al.
2016/0038068 A1 2/2016 Chickering, III et al.
2016/0038684 A1 2/2016 Lum et al.
2016/0081606 A1 3/2016 Russ et al.
2016/0089070 A1 3/2016 Russ et al.
2016/0113560 A1 4/2016 Bullington et al.
2016/0135724 A1 5/2016 Bullington et al.
2016/0174888 A1 6/2016 Berthier et al.
2016/0174948 A1 6/2016 Kato et al.
2016/0213294 A1 7/2016 Patton
2016/0257586 A1 9/2016 Shaamsundarr

(56) References Cited

U.S. PATENT DOCUMENTS

| | | | |
|---|---|---|---|
| 2016/0361006 | A1 | 12/2016 | Bullington et al. |
| 2016/0367177 | A1 | 12/2016 | Edelhauser et al. |
| 2017/0020427 | A1 | 1/2017 | Rogers et al. |
| 2017/0020428 | A1 | 1/2017 | Rogers et al. |
| 2017/0059552 | A1 | 3/2017 | Campton et al. |
| 2017/0065733 | A1 | 3/2017 | Bullington et al. |
| 2017/0071519 | A1 | 3/2017 | Gelfand et al. |
| 2017/0114392 | A1 | 4/2017 | Sambursky et al. |
| 2017/0150913 | A1 | 6/2017 | Patton |
| 2017/0153165 | A1 | 6/2017 | Nwadigo |
| 2017/0156654 | A1 | 6/2017 | Patton |
| 2017/0172482 | A1 | 6/2017 | Patton |
| 2017/0181683 | A1 | 6/2017 | Patton |
| 2017/0227536 | A1 | 8/2017 | Matsuura |
| 2017/0276679 | A1 | 9/2017 | Chapman et al. |
| 2017/0327867 | A1 | 11/2017 | Dohale et al. |
| 2017/0361019 | A1 | 12/2017 | Hopkins |
| 2018/0078186 | A1 | 3/2018 | Patton |
| 2018/0085042 | A1 | 3/2018 | Patton |
| 2018/0092582 | A1 | 4/2018 | Patton |
| 2018/0092583 | A1 | 4/2018 | Patton |
| 2018/0092584 | A1* | 4/2018 | Bullington ........... A61B 10/007 |
| 2018/0093077 | A1 | 4/2018 | Harding et al. |
| 2018/0098723 | A1 | 4/2018 | Patton |
| 2018/0116577 | A1 | 5/2018 | Bullington et al. |
| 2018/0141041 | A1* | 5/2018 | Paek ...................... H04N 23/56 |
| 2018/0160958 | A1 | 6/2018 | Baid |
| 2018/0177445 | A1 | 6/2018 | Rogers et al. |
| 2018/0177943 | A1 | 6/2018 | Bullington et al. |
| 2018/0207300 | A1 | 7/2018 | Bullington et al. |
| 2018/0242890 | A1 | 8/2018 | Chickering, III et al. |
| 2018/0271425 | A1 | 9/2018 | Rogers et al. |
| 2018/0289894 | A1 | 10/2018 | Hopkins |
| 2018/0321270 | A1 | 11/2018 | Iwashita et al. |
| 2018/0353117 | A1 | 12/2018 | Bullington et al. |
| 2019/0000367 | A1 | 1/2019 | Lundquist et al. |
| 2019/0030293 | A1 | 1/2019 | Rogers et al. |
| 2019/0049442 | A1 | 2/2019 | Guirguis |
| 2019/0076074 | A1 | 3/2019 | Bullington et al. |
| 2019/0150818 | A1 | 5/2019 | Bullington et al. |
| 2019/0151536 | A1 | 5/2019 | Bullington et al. |
| 2019/0159711 | A1 | 5/2019 | Rogers et al. |
| 2019/0175085 | A1 | 6/2019 | Bullington et al. |
| 2019/0175087 | A1 | 6/2019 | Bullington et al. |
| 2019/0209066 | A1 | 7/2019 | Bullington et al. |
| 2019/0365303 | A1 | 12/2019 | Bullington et al. |
| 2019/0374145 | A1 | 12/2019 | Breindel et al. |
| 2020/0060595 | A1 | 2/2020 | Bullington et al. |
| 2020/0060596 | A1 | 2/2020 | Patton |
| 2020/0197925 | A1 | 6/2020 | Ivosevic et al. |
| 2020/0214611 | A1 | 7/2020 | Ivosevic |
| 2020/0215211 | A1 | 7/2020 | Bullington et al. |
| 2020/0253524 | A1 | 8/2020 | Bullington et al. |
| 2020/0281514 | A1 | 9/2020 | Rogers et al. |
| 2020/0289039 | A1 | 9/2020 | Bullington et al. |
| 2020/0305780 | A1 | 10/2020 | Rogers et al. |
| 2020/0352497 | A1 | 11/2020 | Brewer et al. |
| 2020/0359951 | A1 | 11/2020 | Bullington et al. |
| 2021/0008280 | A1 | 1/2021 | Bullington et al. |
| 2021/0085230 | A1 | 3/2021 | Brewer et al. |
| 2021/0169387 | A1 | 6/2021 | Bullington et al. |
| 2021/0178389 | A1 | 6/2021 | Bullington et al. |
| 2021/0186392 | A1 | 6/2021 | Bullington et al. |
| 2021/0290123 | A1 | 9/2021 | Sawyer |
| 2021/0345919 | A1 | 11/2021 | Brewer et al. |
| 2021/0345920 | A1 | 11/2021 | Brewer et al. |
| 2021/0345921 | A1 | 11/2021 | Brewer et al. |
| 2021/0345922 | A1 | 11/2021 | Brewer et al. |
| 2021/0353193 | A1 | 11/2021 | Bullington et al. |
| 2021/0353194 | A1 | 11/2021 | Bullington et al. |
| 2021/0361206 | A1 | 11/2021 | Bullington et al. |
| 2021/0361207 | A1 | 11/2021 | Rogers et al. |
| 2022/0023539 | A1 | 1/2022 | Hopkins |
| 2022/0071533 | A1 | 3/2022 | Bullington et al. |
| 2022/0079482 | A1 | 3/2022 | Bullington et al. |
| 2022/0151525 | A1 | 5/2022 | Bullington et al. |
| 2022/0151526 | A1 | 5/2022 | Bullington et al. |
| 2022/0151527 | A1 | 5/2022 | Bullington et al. |
| 2022/0175284 | A1 | 6/2022 | Bullington et al. |
| 2022/0183600 | A1 | 6/2022 | Bullington et al. |
| 2022/0218248 | A1 | 7/2022 | Bullington et al. |
| 2022/0218249 | A1 | 7/2022 | Bullington et al. |
| 2022/0218250 | A1 | 7/2022 | Bullington et al. |
| 2022/0287604 | A1 | 9/2022 | Armstrong et al. |
| 2022/0304600 | A1 | 9/2022 | Hammer |
| 2022/0304601 | A1 | 9/2022 | Bullington et al. |
| 2022/0304664 | A1 | 9/2022 | Hammer |
| 2022/0330858 | A1 | 10/2022 | Thompson et al. |
| 2022/0361786 | A1 | 11/2022 | Bullington et al. |
| 2022/0369970 | A1 | 11/2022 | Bullington et al. |
| 2022/0369971 | A1 | 11/2022 | Bullington et al. |
| 2022/0369972 | A1 | 11/2022 | Bullington et al. |
| 2023/0109255 | A1 | 4/2023 | Rogers et al. |
| 2023/0172502 | A1 | 6/2023 | Bullington et al. |
| 2023/0190157 | A1 | 6/2023 | Bullington et al. |
| 2023/0191033 | A1 | 6/2023 | Nason et al. |
| 2023/0240571 | A1 | 8/2023 | Bullington et al. |
| 2023/0248281 | A1 | 8/2023 | Bullington et al. |
| 2023/0363674 | A1 | 11/2023 | Bullington et al. |
| 2024/0008780 | A1 | 1/2024 | Bullington et al. |
| 2024/0041369 | A1 | 2/2024 | Bullington et al. |
| 2024/0041370 | A1 | 2/2024 | Bullington et al. |
| 2024/0057908 | A1 | 2/2024 | Bullington et al. |
| 2024/0065590 | A1 | 2/2024 | Bullington et al. |
| 2024/0131258 | A1 | 4/2024 | Bullington et al. |
| 2024/0138734 | A1 | 5/2024 | Bullington et al. |
| 2024/0164670 | A1 | 5/2024 | Patton |
| 2024/0306963 | A1 | 9/2024 | Bullington et al. |
| 2024/0306964 | A1 | 9/2024 | Bullington et al. |
| 2024/0315620 | A1 | 9/2024 | Bullington et al. |
| 2024/0315621 | A1 | 9/2024 | Bullington et al. |
| 2024/0315622 | A1 | 9/2024 | Bullington et al. |
| 2024/0315623 | A1 | 9/2024 | Bullington et al. |
| 2024/0315624 | A1 | 9/2024 | Bullington et al. |
| 2025/0073704 | A1 | 3/2025 | Bullington et al. |
| 2025/0082235 | A1 | 3/2025 | Bullington et al. |
| 2025/0120628 | A1 | 4/2025 | Bullington et al. |
| 2025/0235133 | A1 | 7/2025 | Bullington et al. |
| 2025/0235613 | A1 | 7/2025 | Bullington |
| 2025/0275697 | A1 | 9/2025 | Bullington et al. |

FOREIGN PATENT DOCUMENTS

| | | | |
|---|---|---|---|
| AU | 736156 | B2 | 7/2001 |
| AU | 2003244890 | A1 | 1/2004 |
| BR | 112012025546 | A2 | 6/2016 |
| CA | 1264275 | A | 1/1990 |
| CA | 3074105 | A1 | 3/2019 |
| CN | 86103696 | A | 1/1987 |
| CN | 2115767 | U | 9/1992 |
| CN | 1713928 | A | 12/2005 |
| CN | 1784186 | A | 6/2006 |
| CN | 1901955 | A | 1/2007 |
| CN | 2907683 | Y | 6/2007 |
| CN | 1325126 | C | 7/2007 |
| CN | 101060871 | A | 10/2007 |
| CN | 101309641 | A | 11/2008 |
| CN | 101352357 | A | 1/2009 |
| CN | 101437450 | A | 5/2009 |
| CN | 101564301 | A | 10/2009 |
| CN | 101631498 | A | 1/2010 |
| CN | 101676001 | A | 3/2010 |
| CN | 101785676 | A | 7/2010 |
| CN | 101801445 | A | 8/2010 |
| CN | 201617841 | U | 11/2010 |
| CN | 102421362 | A | 4/2012 |
| CN | 102548524 | A | 7/2012 |
| CN | 102811754 | A | 12/2012 |
| CN | 102971040 | A | 3/2013 |
| CN | 103027727 | A | 4/2013 |
| CN | 101626803 | B | 8/2013 |
| CN | 103477201 | A | 12/2013 |
| CN | 103619386 | A | 3/2014 |
| CN | 104902817 | A | 9/2015 |

(56) References Cited

FOREIGN PATENT DOCUMENTS

| | | | |
|---|---|---|---|
| CN | 104955392 | A | 9/2015 |
| CN | 104971390 | A | 10/2015 |
| CN | 104981203 | A | 10/2015 |
| CN | 105090005 | A | 11/2015 |
| CN | 105612346 | A | 5/2016 |
| CN | 105813669 | A | 7/2016 |
| CN | 107736901 | A | 2/2018 |
| CN | 107874786 | A | 4/2018 |
| CN | 209916854 | U | 1/2020 |
| CN | 111132602 | A | 5/2020 |
| CN | 111771054 | A | 10/2020 |
| DE | 7203008 | U | 5/1972 |
| DE | 2203858 | A1 | 5/1973 |
| DE | 2541494 | A1 | 3/1977 |
| DE | 2203858 | B2 | 10/1977 |
| DE | 2946660 | A1 | 5/1981 |
| DE | 3403957 | A1 | 8/1985 |
| DE | 4026732 | A1 | 2/1992 |
| DE | 29913417 | U1 | 12/2000 |
| DE | 10038026 | A1 | 2/2001 |
| DE | 10134913 | A1 | 2/2003 |
| DE | 10134913 | C2 | 6/2003 |
| DE | 10243129 | A1 | 4/2004 |
| DE | 69632870 | T2 | 7/2005 |
| DE | 102009057792 | B4 | 8/2016 |
| EP | 0181957 | A1 | 5/1986 |
| EP | 0207304 | A1 | 1/1987 |
| EP | 0448795 | A2 | 10/1991 |
| EP | 0208053 | B1 | 12/1991 |
| EP | 0329786 | B1 | 1/1993 |
| EP | 0486059 | B1 | 1/1997 |
| EP | 1144026 | B1 | 7/2004 |
| EP | 1505159 | B1 | 5/2008 |
| EP | 1980204 | A1 | 10/2008 |
| EP | 2254472 | A2 | 12/2010 |
| EP | 1381438 | B1 | 5/2012 |
| EP | 2254472 | B1 | 5/2016 |
| EP | 2854643 | B1 | 11/2016 |
| EP | 1487369 | B1 | 5/2017 |
| EP | 2986218 | B1 | 12/2017 |
| EP | 3344213 | B1 | 4/2020 |
| EP | 3634212 | A4 | 3/2021 |
| EP | 2178585 | B1 | 4/2021 |
| EP | 3721086 | A4 | 11/2021 |
| EP | 4059426 | A1 | 9/2022 |
| EP | 3988012 | B1 | 6/2023 |
| EP | 3938108 | B1 | 8/2023 |
| ES | 2564496 | T3 | 3/2016 |
| FR | 2110516 | A5 | 6/1972 |
| FR | 2691364 | B1 | 8/1999 |
| FR | 2833175 | B1 | 5/2004 |
| FR | 2851167 | B1 | 10/2005 |
| GB | 1506449 | A | 4/1978 |
| GB | 1562686 | A | 3/1980 |
| IE | 904353 | A1 | 10/1991 |
| IL | 128709 | A | 9/2004 |
| JP | S4846180 | A | 7/1973 |
| JP | S5397289 | A | 8/1978 |
| JP | S56109643 | A | 8/1981 |
| JP | S5789869 | A | 6/1982 |
| JP | S6458241 | A | 3/1989 |
| JP | H0363570 | A | 3/1991 |
| JP | H05501071 | A | 3/1993 |
| JP | H0551222 | B2 | 8/1993 |
| JP | H06500403 | A | 1/1994 |
| JP | H0716219 | A | 1/1995 |
| JP | H0910302 | A | 1/1997 |
| JP | H0951947 | A | 2/1997 |
| JP | H09229828 | A | 9/1997 |
| JP | H10153531 | A | 6/1998 |
| JP | H10211274 | A | 8/1998 |
| JP | H1156821 | A | 3/1999 |
| JP | H1176397 | A | 3/1999 |
| JP | H11197236 | A | 7/1999 |
| JP | 2001159630 | A | 6/2001 |
| JP | 2001161668 | A | 6/2001 |
| JP | 2001276181 | A | 10/2001 |
| JP | 3231086 | B2 | 11/2001 |
| JP | 2002116201 | A | 4/2002 |
| JP | 2002272710 | A | 9/2002 |
| JP | 2002528159 | A | 9/2002 |
| JP | 2003126068 | A | 5/2003 |
| JP | 3498201 | B2 | 2/2004 |
| JP | 2005237617 | A | 9/2005 |
| JP | 2006026327 | A | 2/2006 |
| JP | 3813974 | B2 | 8/2006 |
| JP | 2007175534 | A | 7/2007 |
| JP | 2008149076 | A | 7/2008 |
| JP | 2008206734 | A | 9/2008 |
| JP | 2009525819 | A | 7/2009 |
| JP | 2009536554 | A | 10/2009 |
| JP | 4382322 | B2 | 12/2009 |
| JP | 2010514501 | A | 5/2010 |
| JP | 2010524505 | A | 7/2010 |
| JP | 2010189415 | A | 9/2010 |
| JP | 4573538 | B2 | 11/2010 |
| JP | 2010536014 | A | 11/2010 |
| JP | 2011512987 | A | 4/2011 |
| JP | 4861649 | B2 | 1/2012 |
| JP | 4869910 | B2 | 2/2012 |
| JP | 5344252 | B2 | 11/2013 |
| JP | 5620541 | B2 | 11/2014 |
| JP | 2015014552 | A | 1/2015 |
| JP | 2015519145 | A | 7/2015 |
| JP | 2015215355 | A | 12/2015 |
| JP | 2016500278 | A | 1/2016 |
| JP | 2016504075 | A | 2/2016 |
| JP | 2016520827 | A | 7/2016 |
| JP | 2016523591 | A | 8/2016 |
| JP | 5997760 | B2 | 9/2016 |
| JP | 2016527939 | A | 9/2016 |
| JP | 6194415 | B2 | 9/2017 |
| JP | 6242386 | B2 | 12/2017 |
| JP | 2018034009 | A | 3/2018 |
| JP | 2018110967 | A | 7/2018 |
| JP | 2018525191 | A | 9/2018 |
| JP | 2020513906 | A | 5/2020 |
| JP | 2020121167 | A | 8/2020 |
| JP | 7204742 | B2 | 1/2023 |
| KR | 20120030087 | A | 3/2012 |
| KR | 101134279 | B1 | 4/2012 |
| KR | 20160088853 | A | 7/2016 |
| TW | 200528066 | A | 9/2005 |
| WO | WO-1984003213 | A1 | 8/1984 |
| WO | WO-1986005568 | A1 | 9/1986 |
| WO | WO-1990004351 | A1 | 5/1990 |
| WO | WO-1991018632 | A1 | 12/1991 |
| WO | WO-1992016144 | A1 | 10/1992 |
| WO | WO-1994007415 | A1 | 4/1994 |
| WO | WO-1994012093 | A1 | 6/1994 |
| WO | WO-1994015665 | A1 | 7/1994 |
| WO | WO-1995011712 | A1 | 5/1995 |
| WO | WO-1995016395 | A1 | 6/1995 |
| WO | WO-1995021639 | A1 | 8/1995 |
| WO | WO-1995024176 | A1 | 9/1995 |
| WO | WO-1996021853 | A1 | 7/1996 |
| WO | WO-1997018845 | A1 | 5/1997 |
| WO | WO-1997045714 | A1 | 12/1997 |
| WO | WO-1998034532 | A1 | 8/1998 |
| WO | WO-1998046136 | A1 | 10/1998 |
| WO | WO-1999013925 | A1 | 3/1999 |
| WO | WO-1999029232 | A1 | 6/1999 |
| WO | WO-1999048425 | A1 | 9/1999 |
| WO | WO-1999055232 | A1 | 11/1999 |
| WO | WO-2000024313 | A1 | 5/2000 |
| WO | WO-2000040291 | A1 | 7/2000 |
| WO | WO-2000041624 | A1 | 7/2000 |
| WO | WO-2001008546 | A2 | 2/2001 |
| WO | WO-2001091829 | A2 | 12/2001 |
| WO | WO-2002028457 | A1 | 4/2002 |
| WO | WO-2002045813 | A1 | 6/2002 |
| WO | WO-2002051520 | A1 | 7/2002 |
| WO | WO-2003008012 | A2 | 1/2003 |
| WO | WO-2003041767 | A1 | 5/2003 |

(56) References Cited

FOREIGN PATENT DOCUMENTS

| | | | |
|---|---|---|---|
| WO | WO-2003047660 | A1 | 6/2003 |
| WO | WO-2003078964 | A2 | 9/2003 |
| WO | WO-2003085395 | A1 | 10/2003 |
| WO | WO-2003092573 | A2 | 11/2003 |
| WO | WO-2004082467 | A2 | 9/2004 |
| WO | WO-2004103565 | A2 | 12/2004 |
| WO | WO-2005068011 | A1 | 7/2005 |
| WO | WO-2006031500 | A2 | 3/2006 |
| WO | WO-2006124634 | A1 | 11/2006 |
| WO | WO-2007033319 | A1 | 3/2007 |
| WO | WO-2008028165 | A2 | 3/2008 |
| WO | WO-2008047699 | A1 | 4/2008 |
| WO | WO-2008077047 | A2 | 6/2008 |
| WO | WO-2008101025 | A1 | 8/2008 |
| WO | WO-2008157511 | A1 | 12/2008 |
| WO | WO-2009094345 | A1 | 7/2009 |
| WO | WO-2009113999 | A2 | 9/2009 |
| WO | WO-2010087216 | A1 | 8/2010 |
| WO | WO-2011030282 | A1 | 3/2011 |
| WO | WO-2011050110 | A1 | 4/2011 |
| WO | WO-2011069145 | A2 | 6/2011 |
| WO | WO-2011114413 | A1 | 9/2011 |
| WO | WO-2011123685 | A2 | 10/2011 |
| WO | WO-2011162772 | A1 | 12/2011 |
| WO | WO-2012012127 | A2 | 1/2012 |
| WO | WO-2012114105 | A1 | 8/2012 |
| WO | WO-2013181352 | A1 | 12/2013 |
| WO | WO-2014022275 | A1 | 2/2014 |
| WO | WO-2014022750 | A1 | 2/2014 |
| WO | WO-2014058945 | A1 | 4/2014 |
| WO | WO-2014085800 | A1 | 6/2014 |
| WO | WO-2014089186 | A1 | 6/2014 |
| WO | WO-2014099266 | A2 | 6/2014 |
| WO | WO-2015021165 | A1 | 2/2015 |
| WO | WO-2015091818 | A1 | 6/2015 |
| WO | WO-2016027782 | A1 | 2/2016 |
| WO | WO-2016054252 | A1 | 4/2016 |
| WO | WO-2016201406 | A1 | 12/2016 |
| WO | WO-2017019552 | A1 | 2/2017 |
| WO | WO-2017041087 | A1 | 3/2017 |
| WO | WO-2017133953 | A1 | 8/2017 |
| WO | WO-2017218840 | A1 | 12/2017 |
| WO | WO-2017218848 | A1 | 12/2017 |
| WO | WO-2018125929 | A1 | 7/2018 |
| WO | WO-2018227191 | A1 | 12/2018 |
| WO | WO-2019055487 | A1 | 3/2019 |
| WO | WO-2019113505 | A1 | 6/2019 |
| WO | WO-2019232196 | A1 | 12/2019 |
| WO | WO-2020163744 | A1 | 8/2020 |
| WO | WO-2020185914 | A1 | 9/2020 |
| WO | WO-2020227701 | A1 | 11/2020 |
| WO | WO-2021119487 | A1 | 6/2021 |
| WO | WO-2022203747 | A1 | 9/2022 |
| WO | WO-2023230520 | A1 | 11/2023 |

OTHER PUBLICATIONS

Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.

Avatar: "Is it safe to reinfuse blood drawn from a CVAD via a syringe when checking line patency or drawing blood?" [retrieved online Jul. 31, 2024] URL:https://www.avatargroup.org.au/faq---blood-collection.html, 4 pages.

Barnard, D. R. & Arthur, M. M., "Fibronectin (cold insoluble globulin) in the neonate," Clinical and Laboratory Observations, 102(3): 453-455 (1983).

Bauman et al., "Don't Stick Me Again! Reducing Blood Culture Contamination," INOVA Fairfax Medical Campus, Emergency Department (2019), 1 page.

Baxter, "IV Tubing and Access Devices" authored by and published by Baxter, dated Nov. 6, 2006, 105 pages.

BD Saf-T-Intima Closed IV Catheter System, Becton, Dickinson and Company, 2015 Brochure. Retrieved from the Internet (Sep. 11, 2019) https://www.bd.com/en-us/offerings/capabilities/infusion-therapy/iv-catheters/bd-saf-tintima-closed-iv-catheter-system, 2 pages.

BD Vacutainer Passive Shielding Blood Collection Needle Brochure; Becton Dickinson and Company (2005), 2 pages.

Bell et al., Effectiveness of a Novel Specimen Collection System in Reducing Blood Culture Contamination Rates, J. Emergency Nursing, vol. 44, No. 6, 570 (Nov. 2018), 6 pages.

Blakeney, "Reduction of Blood Culture Contaminations Using Initial Specimen Diversion Device," Beebe Healthcare (Jun. 2018), 1 page.

Brecher, M. E. et al., "Bacterial Contamination of Blood Components," Clinical Microbiology Reviews, 18(1):195-204 (2005).

Brownfield et al., "Emergency Department Observes 83% Reduction in Blood Culture Contamination with Initial Specimen Diversion Technology Adoption," Am. J. Infection Control, vol. 49, S14, ADS 34 (Jun. 2021), 1 page.

Bruneau, Cecile, et al.; "Efficacy of a new collection procedure for preventing bacterial contamination of whole-blood donations," Transfusion (2001); 41(1):74-81.

Calam, R. R., "Recommended 'Order of Draw' for Collecting Blood Specimens Into Additive-Containing Tubes," Letter to the Editor, Clinical Chemistry, 28(6):1399 (1982), 1 page.

Cartridge and Test Information, Abbott, Art: 714258-010 Rev. Date: Aug. 15, 2016, 6 pages.

Challiner, A. et al., Queen Alexandra Hospital, Portsmouth P06 3LY, "Venous/arterial blood management protection system," Anaesthesia, Correspondence (Feb. 1992); 47(2), p. 169.

Chamarthy, P., et al.; "Mixing Characteristics in a Serpentine Micro-Channel," IMECE2004-61902; Proceedings of the ASME 2004 International Mechanical Engineering Congress and Exposition. Fluids Engineering. Anaheim, California, USA; Nov. 13-19, 2004, pp. 253-261; Exhibit 4; 10 pages.

Chang et al., "Impact of Blood Culture Diversion Device and Molecular Pathogen Identification on Vancomycin Use," San Antonio Military Medical Center (2016), 1 page.

De Korte, D. et al., "Diversion of first blood vol. results in a reduction of bacterial contamination for whole-blood collections," Vox Sanguinis, 83:13-16 (2002).

De Korte, D. et al., "Effects of skin disinfection method, deviation bag, and bacterial screening on clinical safety of platelet transfusions in the Netherlands," Transfusion, 46:476-485 (2006).

Doern et al., "A Comprehensive Update on the Problem of Blood Culture Contamination and a Discussion of Methods for Addressing the Problem," Clinical Microbiology, vol. 33, No. 1, e00009-19 (Jan. 2020), 21 pages.

Edwards Lifesciences, "Conservation. Safety. Simplicity. Edwards Vamp and Vamp Jr. Systems," 2002 Brochure. Retrieved from the Internet (Sep. 11, 2019) https://www.medline.com/media/catalog/Docs/MKT/VAMPSYSTEMBROCHURE.PDF, 4 pages.

Ernst, D. J. et al., "NCCLS simplifies the order of draw: a brief history," MLO, pp. 26-27 (2004).

Extended European Search Report for European Application No. 16808502.5, mailed Jan. 23, 2019, 5 pages.

Extended European Search Report for European Application No. 17204012.3, mailed Feb. 14, 2018, 7 pages.

Extended European Search Report for European Application No. 18188136.8, mailed May 16, 2019, 9 pages.

Extended European Search Report for European Application No. 18855938.9, mailed Aug. 2, 2021, 7 pages.

Extended European Search Report for European Application No. 18885543.1, mailed Oct. 8, 2021, 8 pages.

Extended European Search Report for European Application No. 19156636.3, mailed Aug. 27, 2019, 7 pages.

Extended European Search Report for European Application No. 19190772.4, mailed Feb. 10, 2020, 7 pages.

Extended European Search Report for European Application No. 20176877.7, mailed Dec. 1, 2020, 9 pages.

Extended European Search Report for European Application No. 20207898.6, mailed Aug. 30, 2021, 8 pages.

Extended European Search Report for European Application No. 21167069.0, mailed Nov. 10, 2021, 9 pages.

(56) References Cited

OTHER PUBLICATIONS

Extended European Search Report for European Application No. 21167625.9, mailed Oct. 8, 2021, 7 pages.
Extended European Search Report for European Application No. 21197514, mailed Mar. 30, 2022.
Extended European Search Report for European Application No. 22158983.1, mailed Aug. 1, 2022, 9 pages.
Extended European Search Report for European Application No. 22172183.0, mailed Sep. 11, 2022, 7 pages.
Extended European Search Report for European Application No. 22194769.0, mailed Feb. 28, 2023, 9 pages.
Extended European Search Report for European Application No. 22210589.2, mailed Apr. 17, 2023, 6 pages.
Extended European Search Report for European Application No. 23153164.1, mailed Aug. 7, 2023, 8 pages.
Extended European Search Report for European Application No. 23171135.9, mailed Oct. 30, 2023, 8 pages.
Extended European Search Report for European Application No. 23182529.0, mailed Dec. 19, 2023, 13 pages.
Extended European Search Report for European Application No. 23209844.2, mailed Mar. 20, 2024, 9 pages.
Extended European Search Report for European Application No. 23217471.4, mailed May 22, 2024, 8 pages.
Extended European Search Report for European Application No. 23218666.8 mailed Apr. 18, 2024, 9 pages.
Extended European Search Report for European Application No. 24217446.4, mailed Apr. 17, 2025, 8 pages.
Garstecki, P., et al.; "Formation of droplets and bubbles in a microfluidic T-junction-scaling and mechanism of break-up," Lab Chip; 6(3):437-446 (Mar. 2006).
Geisler et al., "Model to Evaluate the Impact of Hospital-Based Interventions Targeting False-Positive Blood Cultures on Economic and Clinical Outcomes," J. Hospital Infection, vol. 102, No. 4, pp. 438-444 (Mar. 2019).
Gottlieb, T., "Hazards of Bacterial Contamination of Blood Products," Anaesth Intens Care, 21:20-23 (1993).
Hall, K. K. et al., "Updated Review of Blood Culture Contamination," Clinical Microbiology Reviews, 19(4):788-802 (2006).
Hillyer, C. D. et al., "Bacterial Contamination of Blood Components Risks, Strategies, and Regulation," Hematology, pp. 575-589 (2003).
International Search Report and Written Opinion for International Application No. PCT/US2007/087951, mailed May 16, 2008, 8 pages.
International Search Report and Written Opinion for International Application No. PCT/US2013/043289, mailed Oct. 24, 2013, 15 pages.
International Search Report and Written Opinion for International Application No. PCT/US2013/052493, mailed Nov. 27, 2013, 7 pages.
International Search Report and Written Opinion for International Application No. PCT/US2013/063975, mailed Mar. 20, 2014, 16 pages.
International Search Report and Written Opinion for International Application No. PCT/US2013/071491, mailed Aug. 5, 2014, 9 pages.
International Search Report and Written Opinion for International Application No. PCT/US2013/072563, mailed Feb. 7, 2014, 11 pages.
International Search Report and Written Opinion for International Application No. PCT/US2013/073080, mailed Feb. 18, 2014, 14 pages.
International Search Report and Written Opinion for International Application No. PCT/US2016/037160, mailed Sep. 30, 2016, 15 pages.
International Search Report and Written Opinion for International Application No. PCT/US2018/036910, mailed Sep. 4, 2018, 13 pages.
International Search Report and Written Opinion for International Application No. PCT/US2018/050621, mailed Nov. 26, 2018, 11 pages.
International Search Report and Written Opinion for International Application No. PCT/US2018/064561, mailed Feb. 11, 2019, 9 pages.
International Search Report and Written Opinion for International Application No. PCT/US2019/034626, mailed Aug. 22, 2019, 16 pages.
International Search Report and Written Opinion for International Application No. PCT/US2020/022125, mailed May 26, 2020, 17 pages.
Kim, J. Y. et al., "The Sum of the Parts is Greater Than the Whole: Reducing Blood Culture Contamination," Annals of Internal Medicine, 154:202-203 (2011).
Lanteri et al., "Reduction of Blood Culture Contaminations in the Emergency Department," Department of Emergency Medicine, San Antonio Military Medical Center (2016), 1 page.
Levin, P. D. et al., "Use of the Nonwire Central Line Hub to Reduce Blood Culture Contamination," Chest, 143(3):640-645 (2013).
Li, Y., et al.; "Direct labeling and visualization of blood vessels with lipophilic carbocyanine dye Dil," Nature Protocols; 3(11):1703-1708 (2008).
Liumbruno, G. M. et al., "Reduction of the risk of bacterial contamination of blood components through diversion of the first part of the donation of blood and blood components," Blood Transfus., 7:86-93 (2009).
Marshall, L.A., et al.; "An injection molded microchip for nucleic acid purification from 25 microliter samples using isotachophoresis," J Chromatogr A.; 1331; pp. 139-142 (Feb. 2014).
Mayer, G. A, "A Method for the Reliable Determination of Clotting Time in Whole Blood," Can Med Assoc J., 72(12):927-929 (1955).
McDonald, C. P., "Interventions Implemented to Reduce the Risk of Transmission of Bacteria by Transfusion in the English National Blood Service," Transfus Med Hemother, 38:255-258 (2011).
McDonald, C.P.; "Bacterial risk reduction by improved donor arm disinfection, diversion and bacterial screening," Transfus Med., (2006); 16(6):381-396.
Meissner, G. F. et al., "A Method Based on the Use of Whole Venous Blood in Capillary Tubes," American Journal of Clinical Pathology, 33(2):29-31 (1963).
Murphy, M., "Better Blood Transfusion," Journal of the Intensive Core Society, 4(3):78-80 (2003).
Napolitano, M. et al., "Quality control of bacterial contamination of blood components: the feasibility of diversion system testing," Blood Transfus, 2:231-232 (2004).
Nielsen et al., "Initial Specimen Diversion Device Reduces Blood Culture Contamination and Vancomycin Use in Academic Medical Centre," J. Hospital Infection, vol. 120:127-133 (Feb. 2022).
Norberg, A et al., "Contamination Rates of Blood Cultures Obtained by Dedicated Phlebotomy vs Intravenous Catheter," JAMA, 289(6):726-729 (2003).
Office Action for Australian Application No. 2018279941, mailed Mar. 20, 2023, 3 pages.
Office Action for Australian Application No. 2018334138, mailed Jun. 24, 2023, 3 pages.
Office Action for Australian Application No. 2020234829, mailed Nov. 15, 2024, 3 pages.
Office Action for Australian Application No. 2022200818, mailed May 11, 2023, 4 pages.
Office Action for Australian Application No. 2024203105, mailed Jan. 21, 2025, 3 pages.
Office Action for Australian Application No. 2024203140, mailed Apr. 8, 2025, 4 pages.
Office Action for Canadian Application No. 2932536, mailed Nov. 8, 2019, 6 pages.
Office Action for Canadian Application No. 2932536, mailed Oct. 23, 2020, 6 pages.
Office Action for Canadian Application No. 3066670, mailed Oct. 4, 2024, 4 pages.
Office Action for Canadian Application No. 3074105, mailed Nov. 15, 2024, 5 pages.

(56) References Cited

OTHER PUBLICATIONS

Office Action for Canadian Application No. 3087992, mailed Mar. 20, 2025, 4 pages.
Office Action for Canadian Application No. 3120161, mailed Jun. 20, 2022, 4 pages.
Office Action for Canadian Application No. 3136331, mailed Feb. 21, 2023, 4 pages.
Office Action for Canadian Application No. 3183294, mailed Aug. 19, 2024, 5 pages.
Office Action for Chinese Application No. 201380040468.7, mailed Jun. 30, 2016, with English Translation, 9 pages.
Office Action for Chinese Application No. 201380072185.0, mailed Sep. 28, 2016, with English Translation, 17 pages.
Office Action for Chinese Application No. 201811146373.4, mailed Apr. 8, 2025, with English translation, 18 pages.
Office Action for Chinese Application No. 201811146373.4, mailed Aug. 25, 2021, with English language translation, 10 pages.
Office Action for Chinese Application No. 201811146373.4, mailed Jan. 29, 2022, with English language translation, 21 pages.
Office Action for Chinese Application No. 201811146373.4, mailed Nov. 4, 2020, with English language translation, 17 pages.
Office Action for Chinese Application No. 201880050862.1, mailed Mar. 14, 2022, with English translation, 19 pages.
Office Action for Chinese Application No. 201880066848.0, mailed Apr. 20, 2022, with English Translation, 10 pages.
Office Action for Chinese Application No. 201880088771.7, mailed Sep. 3, 2021, with English translation, 17 pages.
Office Action for Chinese Application No. 202080033513.6, mailed Oct. 9, 2022, with English translation, 19 pages.
Office Action for Chinese Application No. 202080094860.X, mailed Jan. 10, 2025, with English translation, 20 pages.
Office Action for European Application No. 20716348.6, mailed Jul. 12, 2022, 7 pages.
Office Action for Indian Application No. 202017008581, mailed Mar. 8, 2022, with English translation, 7 pages.
Office Action for Israeli Application No. 286263, mailed May 12, 2024, 4 pages.
Office Action for Israeli Application No. 309638, mailed Jul. 16, 2024, 3 pages.
Office Action for Japanese Application No. 2015-545813, mailed Jul. 4, 2017, with English Translation, 14 pages.
Office Action for Japanese Application No. 2018-081980, mailed Feb. 21, 2019, with English Translation, 9 pages.
Office Action for Japanese Application No. 2018-081980, mailed Jan. 30, 2020, 11 pages.
Office Action for Japanese Application No. 2018-086721, mailed Mar. 15, 2019, with English Translation, 6 pages.
Office Action for Japanese Application No. 2019-230734, mailed Jan. 22, 2021, with English Translation, 9 pages.
Office Action for Japanese Application No. 2019-230734, mailed Jan. 5, 2022, with English Translation, 6 pages.
Office Action for Japanese Application No. 2020-075727, mailed Jul. 21, 2021, with English translation, 37 pages.
Office Action for Japanese Application No. 2020-094488, mailed Aug. 2, 2021, with English Translation, 4 pages.
Office Action for Japanese Application No. 2020-094488, mailed Mar. 31, 2022, with English Translation, 6 pages.
Office Action for Japanese Application No. 2020-511930, mailed Aug. 23, 2022, with English translation, 9 pages.
Office Action for Japanese Application No. 2020-517772, mailed Dec. 26, 2022, with English Translation, 6 pages.
Office Action for Japanese Application No. 2020-517772, mailed Mar. 14, 2022, with English Translation, 13 pages.
Office Action for Japanese Application No. 2020-550048, mailed Aug. 5, 2022, with English Translation, 5 pages.
Office Action for Japanese Application No. 2020-566232 mailed Apr. 12, 2023, with English translation, 27 pages.
Office Action for Japanese Application No. 2021-552145, mailed Jan. 15, 2024, with English Translation, 9 pages.
Office Action for Japanese Application No. 2022-074696 mailed Feb. 20, 2023, with English translation, 11 pages.
Office Action for Japanese Application No. 2022-184274, mailed Jun. 14, 2024, with English Translation, 4 pages.
Office Action for Japanese Application No. 2022-184274, mailed Oct. 27, 2023, with English translation, 6 pages.
Office Action for Japanese Application No. 2022-212405, mailed Jun. 20, 2024, with English translation, 6 pages.
Office Action for Japanese Application No. 2022-534220, mailed Sep. 13, 2024, with English Translation, 8 pages.
Office Action for Japanese Application No. 2023-075104 mailed Feb. 29, 2024, with English Translation, 9 pages.
Office Action for Japanese Application No. 2024-020482 mailed Mar. 11, 2025, with English Translation, 16 pages.
Office Action for United Kingdom Application No. GB 1805101.1, mailed May 25, 2018, 8 pages.
Office Action for U.S. Appl. No. 11/955,635, mailed Dec. 3, 2010, 11 pages.
Office Action for U.S. Appl. No. 11/955,635, mailed Jul. 22, 2010, 11 pages.
Office Action for U.S. Appl. No. 13/335,241, mailed Apr. 20, 2012, 12 pages.
Office Action for U.S. Appl. No. 13/458,508, mailed Jul. 24, 2012, 13 pages.
Office Action for U.S. Appl. No. 13/675,295, mailed May 23, 2013, 15 pages.
Office Action for U.S. Appl. No. 13/952,964, mailed Mar. 20, 2015, 11 pages.
Office Action for U.S. Appl. No. 13/954,528, mailed Mar. 17, 2014, 10 pages.
Office Action for U.S. Appl. No. 14/089,267, mailed Jun. 19, 2014, 13 pages.
Office Action for U.S. Appl. No. 14/096,826, mailed Jul. 26, 2017, 12 pages.
Office Action for U.S. Appl. No. 14/096,826, mailed Mar. 8, 2018, 14 pages.
Office Action for U.S. Appl. No. 14/493,796, mailed Jan. 27, 2015, 7 pages.
Office Action for U.S. Appl. No. 14/494,208, mailed Jan. 27, 2015, 7 pages.
Office Action for U.S. Appl. No. 14/498,102, mailed Oct. 17, 2017, 20 pages.
Office Action for U.S. Appl. No. 14/498,102, mailed Sep. 24, 2018, 18 pages.
Office Action for U.S. Appl. No. 14/662,676, mailed Sep. 5, 2018, 25 pages.
Office Action for U.S. Appl. No. 14/712,437 mailed Oct. 25, 2018, 20 pages.
Office Action for U.S. Appl. No. 14/728,318, mailed Jul. 18, 2019, 27 pages.
Office Action for U.S. Appl. No. 14/926,784, mailed Jan. 15, 2019, 15 pages.
Office Action for U.S. Appl. No. 14/926,784, mailed Jan. 21, 2020, 17 pages.
Office Action for U.S. Appl. No. 14/926,784, mailed May 25, 2018, 15 pages.
Office Action for U.S. Appl. No. 15/088,842, mailed Nov. 23, 2016, 20 pages.
Office Action for U.S. Appl. No. 15/180,454, mailed Apr. 1, 2020, 28 pages.
Office Action for U.S. Appl. No. 15/180,454, mailed Jan. 21, 2021, 24 pages.
Office Action for U.S. Appl. No. 15/180,454, mailed Jul. 25, 2019, 27 pages.
Office Action for U.S. Appl. No. 15/432,310, mailed Apr. 12, 2017, 14 pages.
Office Action for U.S. Appl. No. 15/435,684, mailed Jun. 12, 2017, 19 pages.
Office Action for U.S. Appl. No. 15/448,891, mailed Jun. 16, 2017, 25 pages.
Office Action for U.S. Appl. No. 15/457,082, mailed Jun. 15, 2017, 22 pages.

(56) References Cited

OTHER PUBLICATIONS

Office Action for U.S. Appl. No. 15/829,015, mailed Feb. 6, 2018, 24 pages.
Office Action for U.S. Appl. No. 15/829,018, mailed Feb. 16, 2018, 13 pages.
Office Action for U.S. Appl. No. 15/829,023, mailed Feb. 7, 2018, 25 pages.
Office Action for U.S. Appl. No. 15/832,055, mailed Feb. 8, 2018, 21 pages.
Office Action for U.S. Appl. No. 15/832,087, mailed Feb. 7, 2018, 24 pages.
Office Action for U.S. Appl. No. 15/832,091, mailed Feb. 22, 2018, 16 pages.
Office Action for U.S. Appl. No. 15/854,273, mailed Jan. 13, 2020, 13 pages.
Office Action for U.S. Appl. No. 15/854,273, mailed Mar. 15, 2019, 19 pages.
Office Action for U.S. Appl. No. 15/854,273, mailed Sep. 7, 2018, 15 pages.
Office Action for U.S. Appl. No. 16/004,955, mailed Feb. 16, 2021, 28 pages.
Office Action for U.S. Appl. No. 16/129,066, mailed Sep. 3, 2020, 13 pages.
Office Action for U.S. Appl. No. 16/213,005, mailed Feb. 3, 2021, 15 pages.
Office Action for U.S. Appl. No. 16/255,055, mailed Mar. 18, 2019, 16 pages.
Office Action for U.S. Appl. No. 16/255,058, mailed Mar. 30, 2021, 16 pages.
Office Action for U.S. Appl. No. 16/274,835, mailed Feb. 12, 2021, 17 pages.
Office Action for U.S. Appl. No. 16/299,962, mailed Dec. 26, 2019, 14 pages.
Office Action for U.S. Appl. No. 16/299,962, mailed Dec. 9, 2020, 15 pages.
Office Action for U.S. Appl. No. 16/299,962, mailed Jun. 15, 2021, 17 pages.
Office Action for U.S. Appl. No. 16/299,962, mailed May 2, 2019, 14 pages.
Office Action for U.S. Appl. No. 16/376,745, mailed May 14, 2021, 13 pages.
Office Action for U.S. Appl. No. 16/379,128, mailed Apr. 26, 2022, 14 pages.
Office Action for U.S. Appl. No. 16/426,380, mailed May 7, 2021, 28 pages.
Office Action for U.S. Appl. No. 16/426,380, mailed Oct. 30, 2020, 29 pages.
Office Action for U.S. Appl. No. 16/789,034, mailed Feb. 9, 2023, 11 pages.
Office Action for U.S. Appl. No. 16/815,526, mailed Aug. 18, 2022, 13 pages.
Office Action for U.S. Appl. No. 16/934,975, mailed Oct. 6, 2022, 18 pages.
Office Action for U.S. Appl. No. 17/136,882, mailed Apr. 19, 2024, 8 pages.
Office Action for U.S. Appl. No. 17/136,882, mailed Dec. 31, 2024, 6 pages.
Office Action for U.S. Appl. No. 17/136,882, mailed Jun. 9, 2023, 11 pages.
Office Action for U.S. Appl. No. 17/136,882, mailed Nov. 8, 2023, 11 pages.
Office Action for U.S. Appl. No. 17/138,056, mailed Dec. 21, 2022, 11 pages.
Office Action for U.S. Appl. No. 17/388,971, mailed Nov. 23, 2021, 19 pages.
Office Action for U.S. Appl. No. 17/388,979, mailed Dec. 8, 2021, 21 pages.
Office Action for U.S. Appl. No. 17/390,249 mailed Nov. 8, 2023, 9 pages.
Office Action for U.S. Appl. No. 17/403,500, mailed Jul. 28, 2023, 28 pages.
Office Action for U.S. Appl. No. 17/403,500, mailed May 20, 2024, 28 pages.
Office Action for U.S. Appl. No. 17/403,500, mailed Nov. 13, 2024, 27 pages.
Office Action for U.S. Appl. No. 17/403,500, mailed Sep. 27, 2022, 29 pages.
Office Action for U.S. Appl. No. 17/516,887, mailed Jan. 13, 2025, 42 pages.
Office Action for U.S. Appl. No. 17/525,682, mailed Feb. 7, 2022, 12 pages.
Office Action for U.S. Appl. No. 17/532,382, mailed Feb. 7, 2022, 10 pages.
Office Action for U.S. Appl. No. 17/583,791, mailed Dec. 23, 2024, 19 pages.
Office Action for U.S. Appl. No. 17/591,237, mailed Aug. 25, 2023, 25 pages.
Office Action for U.S. Appl. No. 17/591,237, mailed Aug. 4, 2022, 26 pages.
Office Action for U.S. Appl. No. 17/591,237, mailed Feb. 16, 2023, 34 pages.
Office Action for U.S. Appl. No. 17/591,237, mailed Jan. 24, 2025, 34 pages.
Office Action for U.S. Appl. No. 17/591,237, mailed May 3, 2022, 20 pages.
Office Action for U.S. Appl. No. 17/591,239, mailed Aug. 23, 2023, 23 pages.
Office Action for U.S. Appl. No. 17/591,239, mailed Aug. 4, 2022, 26 pages.
Office Action for U.S. Appl. No. 17/591,239, mailed Feb. 17, 2023, 34 pages.
Office Action for U.S. Appl. No. 17/591,239, mailed Jan. 24, 2025, 32 pages.
Office Action for U.S. Appl. No. 17/591,239, mailed May 3, 2022, 21 pages.
Office Action for U.S. Appl. No. 17/684,920, mailed Jan. 31, 2023, 9 pages.
Office Action for U.S. Appl. No. 17/684,920, mailed Jul. 11, 2022, 12 pages.
Office Action for U.S. Appl. No. 17/710,389, mailed Jun. 16, 2022, 25 pages.
Office Action for U.S. Appl. No. 17/710,401, mailed Jul. 6, 2022, 22 pages.
Office Action for U.S. Appl. No. 17/710,411, mailed Jul. 6, 2022, 22 pages.
Office Action for U.S. Appl. No. 17/863,605, mailed Nov. 28, 2023, 15 pages.
Office Action for U.S. Appl. No. 18/227,185, mailed Apr. 18, 2024, 18 pages.
Office Action for U.S. Appl. No. 18/227,185, mailed Oct. 31, 2024, 17 pages.
Office Action for U.S. Appl. No. 18/380,259, mailed Jan. 29, 2024, 33 pages.
Office Action for U.S. Appl. No. 18/380,259, mailed Oct. 16, 2024, 15 pages.
Office Action for U.S. Appl. No. 18/381,369, mailed Nov. 28, 2023, 16 pages.
Office Action for U.S. Appl. No. 18/399,007, mailed Mar. 7, 2024, 8 pages.
Office Action for U.S. Appl. No. 18/407,010, mailed Mar. 13, 2024, 8 pages.
Office Action for U.S. Appl. No. 18/407,010, mailed Sep. 6, 2024, 11 pages.
Office Action for U.S. Appl. No. 18/675,824, mailed Jul. 26, 2024, 13 pages.
Office Action for U.S. Appl. No. 18/676,186, mailed Aug. 5, 2024, 13 pages.
Office Action for U.S. Appl. No. 18/680,331, mailed Mar. 25, 2025, 8 pages.
Office Action for U.S. Appl. No. 18/680,348, mailed Mar. 25, 2025, 7 pages.

(56) References Cited

OTHER PUBLICATIONS

Office Action for U.S. Appl. No. 18/680,377, mailed Mar. 26, 2025, 12 pages.
Office Action for U.S. Appl. No. 18/680,439, mailed Mar. 31, 2025, 8 pages.
Office Action for U.S. Appl. No. 18/680,466, mailed Dec. 30, 2024, 7 pages.
Office Action for U.S. Appl. No. 18/960,441, mailed Jan. 17, 2025, 8 pages.
Office Action for U.S. Appl. No. 18/990,547, mailed Jan. 31, 2025, 10 pages.
Order of Draw for Multiple Tube Collections, LabNotes, a newsletter from BD Diagnostics,—Preanalytical Systems, 17(1):3 (2007), 1 page.
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Pall Corp., "Leukotrap Filtration Systems for Whole Blood Derived Platelets: Leukotrap RC PL and Leukotrap PL Systems," 2005 Brochure, 2 pages.
Patel, R. et al., "Optimized Pathogen Detection with 30- Compared to 20-Milliliter Blood Culture Draws," Journal of Clinical Microbiology, 49(12):4047-4051 (2011).
Patton, R. G. et al., "Innovation for Reducing Blood Culture Contamination: Initial Specimen Diversion Technique," Journal of Clinical Microbiology, 48(12):4501-4503 (2010).
Perez, P. et al., "Multivariate analysis of determinants of bacterial contamination of whole-blood donations," Vox Sanguinis, 82:55-60 (2002).
Povroznik, "Initial Specimen Diversion Device Utilization Mitigates Blood Culture Contamination Across Regional Community Hospital and Acute Care Facility," Am. J. Medical Quality, vol. 37, No. 5, 405 (Mar. 2022), 8 pages.
Proehl, J. A et al., "Clinical Practice Guideline: Prevention of Blood Culture Contamination, Full Version," 2012 ENA Emergency Nurses Resources Development Committee, Emergency Nurses Association (Dec. 2012), 14 pages.
Quilici, N. et al., "Differential Quantitative Blood Cultures in the Diagnosis of Catheter-Related Sepsis in Intensive Care Units," Clinical Infectious Diseases 25:1066-1070 (1997).
Rupp et al., "Reduction in Blood Culture Contamination Through Use of Initial Specimen Diversion Device," Clinical Infectious Diseases, vol. 65, No. 2, 201 (Jul. 15, 2017), 19 pages.
Schuur, J., "Blood Cultures: When Do they Help and When Do They Harm?" Brigham & Women's Hospital, Department of Emergency Medicine, (Jun. 21-23, 2012), 42 pages.
Shen, H., et al.; "A microfluidic chip based sequential injection system with trapped droplet liquid-liquid extraction and chemiluminescence detection," Lab Chip; 6(10):1387-1389 (Oct. 2006).
Sheppard, C. A., et al.; "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1):11-19 (2000).
Sibley, C. D., et al.; "Molecular Methods for Pathogen and Microbial Community Detection and Characterization: Current and Potential Application in Diagnostic Microbiology," Infection, Genetics and Evolution 12:505-521 (2012).
Skoglund et al., "Estimated Clinical and Economic Impact through Use of a Novel Blood Collection Device To Reduce Blood Culture Contamination in the Emergency Department: a Cost-Benefit Analysis," J Clin Microbiol. (Jan. 2019); 57(1):e01015-18, 10 pages.
Steed et al., "Study Demonstrates Reduction in Blood Culture Contamination Rates with Novel Blood Culture Collection Device," Clinical Lab Products Magazine (Feb. 2018), 2 pages.
Stohl, S. et al., "Blood Cultures at Central Line Insertion in the Intensive Care Unit: Comparison with Peripheral Venipuncture," Journal of Clinical Microbiology, 49(7):2398-2403 (2011).
Supplementary European Search Report for European Application No. 13797732.8, mailed Dec. 7, 2015, 5 pages.
Supplementary European Search Report for European Application No. 13860741.1, mailed Jun. 7, 2016, 5 pages.
Tang, M. et al., "Closed Blood Conservation Device for Reducing Catheter-Related Infections in Children After Cardiac Surgery," Critical Care Nurse, 34(5):53-61 (2014).
Tompkins et al., "Getting to Zero: Impact of A Device To Reduce Blood Culture Contamination and False-Positive Central-Line-Associated Bloodstream Infection," Infection Control & Hospital Epidemiology, pp. 1-5 (Nov. 2022).
Tongma et al., "Significant Reduction of Blood Culture Contamination in the Emergency Department (ED) Using the Steripath® Blood Diversion Device," Open Forum Infectious Diseases, vol. 4, Supp. 1, 2035 (Oct. 2017), 1 page.
Wagner et al., "Diversion of Initial Blood Flow to Prevent Whole-Blood Contamination by Skin Surface Bacteria: an in vitro model," Transfusion, 40:335-338 (2000).
Wang, P. et al., "Strategies on Reducing Blood Culture Contamination," Reviews in Medical Microbiology, 23:63-66 (2012).
Weinbaum, F. I. et al., "Doing It Right the First Time: Quality Improvement and the Contaminant Blood Culture," Journal of Clinical Microbiology, 35(3):563-565 (1997).
Weinstein, M.P., "Current Blood Culture Methods and Systems: Clinical Concepts, Technology, and Interpretation of Results," Clinical Infectious Diseases, 23:40-46 (1996).
Weinstein, M.P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).
Weinstein, M.P., "MINIREVIEW: Blood Culture Contamination: Persisting Problems and Partial Progress," Journal of Clinical Microbiology, 41(6):2275-2278 (2003).
Ziegler, et al., "Controlled Clinical Laboratory Comparison of Two Supplemented Aerobic and Anaerobic Media Used in Automated Blood Culture Systems To Detect Bloodstream Infections," J. Clinical Microbiology, 36(3):657-661 (1998).
Zimmerman et al., "Reducing Blood Culture Contamination Using an Initial Specimen Diversion Device," Am. J. Infection Control, vol. 47, No. 7, pp. 822-826 (Jan. 2019).
Zimmon, D. S. et al., "Effect of Portal Venous Blood Flow Diversion on Portal Pressure," J Clin Invest, 65(6): 1388-1397 (1980).
Zundert, A V., "New Closed IV Catheter System," Acta Anaesth. Belg., 56:283-285 (2005).
Office Action for U.S. Appl. No. 17/869,256, mailed May 5, 2025, 24 pages.
Huang et al., "Rapid and sensitive detection of interleukin-6 in serum via time-resolved lateral flow immunoassay," Analytical Biochemistry, Jan. 1, 2020, vol. 588:113468, 6 pages.
International Preliminary Report on Patentability dated May 17, 2022, for International Application No. PCT/US2020/064600, 8 pages.
International Search Report and Written Opinion for International Application No. PCT/US2020/064600, dated Mar. 18, 2021, 14 pages.
International Search Report and Written Opinion for PCT Application No. PCT/US2023/067418 dated Oct. 16, 2023, 18 pages.
Invitation to Pay for International Application No. PCT/US2023/067418 dated Aug. 25, 2023, 13 pages.
Koczula et al. "Lateral flow assays." Essays in Biochemistry (2016) 60 111-120.
Office Action for U.S. Appl. No. 17/119,732, dated Aug. 25, 2022, 30 pages.
Serebrennikova et al.; "A semi-quantitative rapid multi-range gradient lateral flow immunoassay for procalcitonin," Mikrochim Acta., (2019); 186(7):423, 8 pages.
Shao et al.; "Rapid and Sensitive Lateral Flow Immunoassay Method for Procalcitonin (PCT) Based on Time-Resolved Immunochromatography," Sensors (Basel) (2017); 17(3):480, 10 pages.
AU Application No. 2020218544, Office Action mailed Jul. 31, 2024; Applicant Magnolia Medical Technologies, Inc.; 3 pages.

(56) References Cited

OTHER PUBLICATIONS

AU Application No. 2020234829, Office Action mailed Sep. 11, 2025; Applicant Magnolia Medical Technologies, Inc.; 3 pages.
AU Application No. 2024205062, Office Action mailed Sep. 8, 2025; Applicant Magnolia Medical Technologies, Inc.; 2 pages.
Becton, Dickinson and Company "BD BACTEC™ Blood Culture System," [Retrieval Date Unknown] available online URL:https://www.bd.com/en-us/products-and-solutions/products/product-families/bd-bactec-blood-culture-system; 9 pages (Publication Date Unknown).
Biomerieux "BACT/ALERT® Culture Media: Strong Outside, Strong Inside," PRN 054364 Rev.01A; [Online Retrieval Date Unknown]; URL: https://www.biomerieux.com/us/en/our-offer/clinical-products/bact-alert-culture-media-bottles.html; 10 pages (Publication Date Unknown ).
Buzard, B.A., et al.; "Evaluation of an Initial Specimen Diversion Device (ISDD) on Rates of Blood Culture Contamination in the Emergency Department," Jun. 22, 2020; Kans J Med.; 14(1):73-76 (Mar. 19, 2021).
CA Application No. 2931983, Office Action mailed Oct. 1, 2020; Applicant Magnolia Medical Technologies, Inc.; 3 pages.
CA Application No. 2931983, Office Action mailed Oct. 16, 2019; Applicant Magnolia Medical Technologies, Inc.; 4 pages.
CA Application No. 3101972, Office Action mailed May 13, 2025; Applicant Magnolia Medical Technologies, Inc.; 4 pages.
CA Application No. 3129065, Office Action mailed Feb. 11, 2025; Applicant Magnolia Medical Technologies, Inc.; 3 pages.
CA Application No. 3132981, Office Action mailed Aug. 22, 2025; Applicant Magnolia Medical Technologies, Inc.; 5 pages.
Callado, G.Y., et al.; "Diagnostic Stewardship: A Systematic Review and Meta-analysis of Blood Collection Diversion Devices Used to Reduce Blood Culture Contamination and Improve the Accuracy of Diagnosis in Clinical Settings," Open Forum Infect Dis.; 10(9):ofad433; pp. 1-10. doi: 10.1093/ofid/ofad433 (Aug. 11, 2023).
CN Application No. 201380071681.4, Office Action mailed Aug. 16, 2016; Applicant Magnolia Medical Technologies, Inc., with English Translation; 16 pages.
CN Application No. 201380071681.4, Office Action mailed Jun. 28, 2017; Applicant Magnolia Medical Technologies, Inc., with English Translation; 22 pages.
CN Application No. 201811146373.4, Office Action mailed Jul. 28, 2025; Applicant Magnolia Medical Technologies, Inc., with English Translation; 36 pages.
CN Application No. 202080025953.7, Office Action mailed Aug. 28, 2024; Applicant Magnolia Medical Technologies, Inc., with English Translation; 26 pages.
CN Application No. 202080025953.7, Office Action mailed Dec. 17, 2024; Applicant Magnolia Medical Technologies, Inc., with English Translation; 22 pages.
CN Application No. 202080025953.7, Office Action mailed Jan. 9, 2024; Applicant Magnolia Medical Technologies, Inc., with English Translation; 27 pages.
CN Application No. 202080025953.7, Office Action mailed May 24, 2025; Applicant Magnolia Medical Technologies, Inc., with English Translation; 12 pages.
CN Application No. 202310257287.5, Office Action mailed Apr. 23, 2025; Applicant Magnolia Medical Technologies, Inc., with English Translation; 21 pages.
ENA (Emergency Nurses Association) "Clinical Practice Guideline: Synopsis—Prevention of Blood Culture Contamination," last updated Jan. 9, 2023 [Retrieval Date Unknown] accessed online URL:https://www.guidelinecentral.com/guideline/308349/#section-420; 1 page (May 8, 2018).
EP Application No. 13845555.5, Supplementary European Search Report mailed Jul. 12, 2016; Applicant Bullington, Gregory J. et al.; 6 pages.
EP Application No. 13859067.4, Extended European Search Report mailed Aug. 16, 2017; Applicant Magnolia Medical Technologies, Inc.; 6 pages.
EP Application No. 13859067.4, Extended European Search Report mailed Jan. 27, 2017; Applicant Magnolia Medical Technologies, Inc.; 4 pages.
EP Application No. 13859067.4, Extended European Search Report mailed Jun. 7, 2016; Applicant Magnolia Medical Technologies, Inc.; 4 pages.
EP Application No. 16200112.7, Extended European Search Report mailed Mar. 1, 2017; Applicant Magnolia Medical Technologies, Inc.; 6 pages.
EP Application No. 17206745.6, Extended European Search Report mailed Feb. 19, 2018; Applicant Magnolia Medical Technologies, Inc.; 8 pages.
EP Application No. 17206745.6, Office Action mailed Feb. 18, 2020; Applicant Magnolia Medical Technologies, Inc.; 4 pages.
EP Application No. 20167572.5, Extended European Search Report mailed Sep. 30, 2020; Applicant Magnolia Medical Technologies, Inc.; 10 pages.
EP Application No. 20709440.0, Office Action mailed Feb. 18, 2025; Applicant Magnolia Medical Technologies, Inc.; 6 pages.
EP Application No. 23173044.1, Extended European Search Report mailed Oct. 27, 2023; Applicant Magnolia Medical Technologies, Inc.; 8 pages.
EP Application No. 23182529.0, Office Action mailed Jul. 29, 2025; Applicant Magnolia Medical Technologies, Inc.; 6 pages.
EP Application No. 25164992.7, Extended European Search Report mailed Aug. 26, 2025; Applicant Magnolia Medical Technologies, Inc.; 8 pages.
IL Application No. 238991, Office Action mailed Feb. 13, 2020; Applicant Magnolia Medical Technologies, Inc., with English Translation; 10 pages.
IL Application No. 238991, Office Action mailed Nov. 12, 2018; Applicant Magnolia Medical Technologies, Inc., with English Translation; 6 pages.
IL Application No. 273025, Office Action mailed Dec. 4, 2022; Applicant Magnolia Medical Technologies, Inc et al., with English Translation; 6 pages.
IL Application No. 285289, Office Action mailed May 6, 2024; Applicant Magnolia Medical Technologies, Inc et al.; 4 pages. (English Only).
IL Application No. 286263, Office Action mailed Aug. 5, 2025; Applicant Magnolia Medical Technologies, Inc et al.; 3 pages. (English Only).
IL Application No. 309638, Office Action mailed Aug. 11, 2025; Applicant Magnolia Medical Technologies, Inc et al.; 3 pages. (English Only).
IL Application No. 313917, Office Action mailed May 29, 2025; Applicant Magnolia Medical Technologies, Inc et al.; 4 pages. (English Only).
JP Application No. 2015-545494, Office Action mailed Jun. 19, 2017; Applicant Magnolia Medical Technologies, Inc., with English Translation; 9 pages.
JP Application No. 2021-546225, Office Action mailed Dec. 19, 2023; Applicant Magnolia Medical Technologies, Inc., with English Translation; 11 pages.
JP Application No. 2021-552145, Office Action mailed Sep. 11, 2024; Applicant Magnolia Medical Technologies, Inc., with English Translation; 4 pages.
JP Application No. 2022-184274, Office Action Appeal Decision No. 2024-016403 mailed Nov. 7, 2025, Applicant Magnolia Medical Technologies, Inc., with English translation; 73 pages.
JP Application No. 2024-014849, Office Action mailed Apr. 30, 2025; Applicant Magnolia Medical Technologies, Inc., with English Translation; 9 pages.
JP Application No. 2024-115518, Office Action mailed Jun. 11, 2025; Applicant Magnolia Medical Technologies, Inc., with English Translation; 6 pages.
JP Application No. 2024-127830, Office Action mailed Nov. 4, 2025; Applicant Magnolia Medical Technologies, Inc., with English Translation; 8 pages.
JP Application No. 2024-153369, Office Action mailed Sep. 5, 2025; Applicant Magnolia Medical Technologies, Inc., with English Translation; 10 pages.

(56) References Cited

OTHER PUBLICATIONS

JP Application No. 2024-187934, Office Action mailed Apr. 28, 2025; Applicant Magnolia Medical Technologies, Inc., with English Translation; 12 pages.
Kurin "Changing Blood Culture Collection in Hospitals Across America, Clinical Evidence, Studies" [Retrieved online Sep. 15, 2025] URL:https://www.kurin.com/studies/; 22 pages (Publication Date Unknown).
Kurin "Changing Blood Culture Collection in Hospitals Across America," [Retrieved online Sep. 15, 2025] URL:https://www.kurin.com/clinical-guidelines/; 11 pages (Publication Date Unknown).
Kurin "False Positive Blood Cultures—Improve the accuracy of blood culture," [Retrieved online Sep. 15, 2025] URL:https://www.kurin.com/false-positive-blood-cultures/; 5 pages (Publication Date Unknown).
Kurin "Kurin® Jet™ Blood Culture Collection Ordering Information," Brochure [Retrieval Date Unknown] available online URL: https://www.kurin.com/kurin-jet/ 2 pages (Publication Date Unknown).
Kurin "Kurin Launches Kurin Jet, Redefining the Blood Culture Contamination Device Market," [Retrieval Date Unknown] URL:https://www.kurin.com/kurin-launches-kurin-jet-redefining-the-blood-culture-contamination-device-market/; 5 pages (Publication Date Unknown).
Kurin "Kurin Lock® with Flash Technology: Better than conventional diversion," [Retrieved online Sep. 26, 2025] URL:https://www.kurin.com/kurin-jet/; 10 pages (Publication Date Unknown).
Kurin "Lowering the 3% Blood Culture Contamination Rate Benchmark," [Retrieved online Sep. 15, 2025] URL:https://www.kurin.com/3-percent-standard/; 4 pages (Publication Date Unknown).
Kurin "The Financial and Clinical Costs of False Positive Blood Cultures," [Retrieved online Sep. 15, 2025] URL:https://www.kurin.com/false-positives-blood-culture-cost/; 5 pages (Publication Date Unknown).
Magnolia Medical Technologies, Inc.; "Newly Released CLSI National Blood Culture Guidelines Identify Best Practices and Evidence-Based Technology Solutions Such as Steripath® to Improve Patient Safety and Outcomes," [Retrieved online Sep. 15, 2025] URL: https://magnolia-medical.com/news/newly-released-clsi-national-blood-culture-guidelines-identify-best-practices-and-evidence-based-technology-solutions-such-as-steripath-to-improve-patient-safety-and-outcomes/; 5 pages (May 5, 2022).
Mohajer, M.A., et al.; "The Impact of Initial Specimen Diversion Systems on Blood Culture Contamination," Open Forum Infect Dis.; 10(5):ofad182; pp. 1-6. doi: 10.1093/ofid/ofad182 (Apr. 5, 2023).
PCT Application No. PCT/US2016/050380, International Search Report and Written Opinion mailed Dec. 1, 2016, Applicant Magnolia Medical Technologies, Inc.; 6 pages.
PCT Application No. PCT/US2020/017261, International Search Report and Written Opinion mailed May 14, 2020, Applicant Magnolia Medical Technologies, Inc.; 13 pages.
Snyder, S.R., et al.; "Effectiveness of practices to reduce blood culture contamination: A Laboratory Medicine Best Practices systematic review and meta-analysis," Clin Biochem.; Epub Jun. 16, 2012; 45(Issues 13-14):999-1011. doi: 10.1016/j.clinbiochem.2012.06.007, 13 pages (Sep. 2012).
U.S. Appl. No. 14/049,326, Non-Final Office Action mailed Apr. 24, 2015; Inventor Bullington, Gregory J. et al.; 10 pages.
U.S. Appl. No. 14/264,481, Final Office Action mailed Apr. 13, 2017; Inventor Bullington, Gregory J. et al.; 14 pages.
U.S. Appl. No. 14/264,481, Final Office Action mailed Jul. 14, 2016; Inventor Bullington, Gregory J. et al.; 9 pages.
U.S. Appl. No. 14/264,481, Non-Final Office Action mailed Feb. 26, 2016; Inventor Bullington, Gregory J. et al.; 10 pages.
U.S. Appl. No. 14/264,481, Non-Final Office Action mailed Jul. 1, 2015; Inventor Bullington, Gregory J. et al.; 13 pages.
U.S. Appl. No. 14/264,481, Non-Final Office Action mailed Oct. 21, 2016; Inventor Bullington, Gregory J. et al.; 10 pages.
U.S. Appl. No. 14/264,481, Non-Final Office Action mailed Sep. 7, 2017; Inventor Bullington, Gregory J. et al.; 12 pages.
U.S. Appl. No. 14/838,794, Non-Final Office Action mailed Aug. 3, 2017; Inventor Bullington, Gregory J. et al.; 8 pages.
U.S. Appl. No. 14/880,397, Final Office Action mailed Sep. 24, 2018; Inventor Bullington, Gregory J. et al.; 5 pages.
U.S. Appl. No. 14/880,397, Non-Final Office Action mailed Apr. 17, 2018; Inventor Bullington, Gregory J. et al.; 6 pages.
U.S. Appl. No. 15/925,159, Final Office Action mailed May 14, 2019; Inventor Bullington, Gregory J. et al.; 15 pages.
U.S. Appl. No. 15/925,159, Non-Final Office Action mailed Nov. 26, 2018; Inventor Bullington, Gregory J. et al.; 11 pages.
U.S. Appl. No. 16/785,170, Non-Final Office Action mailed Sep. 14, 2022; Inventor Bullington, Gregory J. et al.; 11 pages.
U.S. Appl. No. 16/815,521, Non-Final Office Action mailed Oct. 25, 2023; Inventor Bullington, Gregory J. et al.; 9 pages.
U.S. Appl. No. 17/516,887, Final Office Action mailed Aug. 13, 2025; Inventor Bullington, Gregory J. et al.; 24 pages.
U.S. Appl. No. 17/591,237, Final Office Action mailed Aug. 20, 2025; Inventor Bullington, Gregory J. et al.; 24 pages.
U.S. Appl. No. 18/240,178, Non-Final Office Action mailed Feb. 27, 2025; Inventor Bullington, Gregory J. et al.; 12 pages.
U.S. Appl. No. 18/240,178, Non-Final Office Action mailed Jun. 12, 2024; Inventor Bullington, Gregory J. et al.; 16 pages.
U.S. Appl. No. 18/242,900, Non-Final Office Action mailed Oct. 23, 2025; Inventor Bullington, Gregory J. et al.; 12 pages.
U.S. Appl. No. 18/407,010, Non-Final Office Action mailed Dec. 4, 2025; Inventor Bullington, Gregory J. et al.; 7 pages.
U.S. Appl. No. 18/680,331, Final Office Action mailed Nov. 24, 2025; Inventor Bullington, Gregory J. et al.; 9 pages.
U.S. Appl. No. 18/680,348, Final Office Action mailed Nov. 24, 2025; Inventor Bullington, Gregory J. et al.; 8 pages.
U.S. Appl. No. 18/680,377, Final Office Action mailed Nov. 25, 2025; Inventor Bullington, Gregory J., et al.; 14 pages.
U.S. Appl. No. 18/680,439, Final Office Action mailed Nov. 25, 2025; Inventor Bullington, Gregory J., et al.; 10 pages.
U.S. Appl. No. 18/680,466, Final Office Action mailed Aug. 20, 2025; Inventor Bullington, Gregory J. et al.; 10 pages.
U.S. Appl. No. 19/175,765, Final Office Action mailed Nov. 26, 2025; Inventor Bullington, Gregory J. et al.; 14 pages.
U.S. Appl. No. 19/175,765, Non-Final Office Action mailed Aug. 8, 2025; Inventor Bullington, Gregory J. et al.; 11 pages.
U.S. Appl. No. 90/015,399, Order Granting Request for Ex Parte Reexamination mailed Oct. 21, 2025; Inventor Bullington, Gregory J., et al.; 43 pages.
U.S. Appl. No. 90/019,177, Ex-Parte Reexamination mailed Aug. 9, 2023; Inventor Bullington, Gregory J. et al.; 11 pages.
U.S. Appl. No. 90/019,177, Ex-Parte Reexamination mailed Dec. 1, 2023; Inventor Bullington, Gregory J. et al.; 19 pages.
U.S. Appl. No. 90/019,177, Order Granting Request for Ex Parte Reexamination mailed Apr. 26, 2023, Inventor Bullington, Gregory J., et al.; 16 pages.
U.S. Appl. No. 90/019,177, Patent Trial and Appeal Board Decision in Ex Parte Reexamination (Exhibit 1003) mailed May 20, 2025, Inventor Bullington, Gregory J., et al.; 22 pages.
U.S. Appl. No. 90/019,756, Ex Parte Reexamination Interview Summary mailed Sep. 17, 2025, Inventor Patton, Richard G.; 7 pages.
U.S. Appl. No. 90/019,756, Ex Parte Reexamination Non-Final Action mailed Nov. 10, 2025; Inventor Patton, Richard G.; 44 pages.
U.S. Appl. No. 90/019,756, Ex-Parte Reexamination mailed Jun. 17, 2025; Inventor Patton, Richard G.; et al.; 38 pages.
U.S. Appl. No. 90/019,757, Ex Parte Reexamination Final Action mailed Nov. 28, 2025; Inventor Patton, Richard G.; 46 pages.
U.S. Appl. No. 90/019,757, Ex Parte Reexamination Interview Summary mailed Sep. 17, 2025, Inventor Patton, Richard G.; 7 pages.
U.S. Appl. No. 90/019,757, Ex-Parte Reexamination Non-Final Office Action mailed Jun. 17, 2025; Inventor Patton, Richard G.; 27 pages.
U.S. Appl. No. 90/019,823, Ex Parte Reexamination Interview Summary mailed Nov. 25, 2025; Inventor Bullington, Gregory J.; 31 pages.

(56) References Cited

OTHER PUBLICATIONS

U.S. Appl. No. 90/019,823, Ex-Parte Reexamination mailed Aug. 25, 2025; Inventor Bullington, Gregory J. et al.; 30 pages.
U.S. Appl. No. 90/019,823, Order Granting Request for Ex Parte Reexamination mailed Feb. 24, 2025, Inventor Miazga, Jay M.; 16 pages.
U.S. Appl. No. 90/019,823, Response to Office Action in Ex Parte Reexamination filed Nov. 25, 2025; Inventor Bullington, Gregory J.; 211 pages.
U.S. Appl. No. 90/019,824, Ex Parte Reexamination Non-Final Action mailed Nov. 4, 2025; Inventor Bullington, Gregory J., et al.; 22 pages.
U.S. Appl. No. 90/019,824, Order Granting Request for Ex Parte Reexamination mailed Feb. 24, 2025, Inventor Bullington, Gregory J., et al.; 18 pages.
U.S. Appl. No. 90/019,825, Ex Parte Reexamination Non-Final Action mailed Nov. 17, 2025; Inventor Bullington, Gregory J., et al.; 25 pages.
U.S. Appl. No. 90/019,825, Order Granting Request for Ex Parte Reexamination mailed Feb. 25, 2025, Inventor Bullington, Gregory J., et al.; 15 pages.
Valleywise Health Medical Center Case Study "In anticipation of CMS changes, AZ hospital identifies solution to blood culture contaminations with new Kurin Jet™," Brochure; 1 page (Publication Date Unknown).
Widmer, A.F., et al.; "Sterilization of skin and catheters before drawing blood cultures," J Clin Microbiol.; 41(10):4910; 1 page (Oct. 2003).
Wilber, E.P., et al.; "Effect of an initial specimen diversion device on blood-culture contamination rates and vancomycin usage: A quasi-experimental study," Epub Aug. 3, 2023; Infect Control Hosp Epidemiol.; 45(1):100-102 (Jan. 2024).
Zwang, O., et al.; "Analysis of strategies to improve cost effectiveness of blood cultures," J Hosp Med.; 1(5):272-276. doi: 10.1002/jhm.115 (Sep. 2006).

* cited by examiner

FLUID TRANSFER DEVICES WITH INTEGRATED FLOW-BASED ASSAY AND METHODS OF USING THE SAME

CROSS-REFERENCE TO RELATED APPLICATIONS

This application is a continuation of U.S. patent application Ser. No. 17/119,732 entitled "Fluid Transfer Devices with Integrated Flow-Based Assay and Methods of Using the Same," filed Dec. 11, 2020, which claims priority to and the benefit of U.S. Provisional Patent Application Ser. No. 62/946,680, filed Dec. 11, 2019, entitled "Fluid Transfer Devices with Integrated Flow-Based Assay and Methods of Using the Same," the disclosures of each of which is incorporated herein by reference in its entirety.

BACKGROUND

Embodiments described herein relate generally to the procurement of bodily fluid samples and point of care diagnostic testing, and more particularly to bodily fluid transfer devices with an integrated flow-based assay system such as, for example, a lateral flow assay allowing for initial point of care diagnostic testing.

Health care practitioners routinely perform various types of microbial as well as other broad diagnostic tests on patients using parenterally obtained bodily fluids. In some instances, effective treatment of some serious patient conditions can be time dependent with delays in treatment potentially resulting in increased risk of morbidity and/or mortality. For example, sepsis is a serious patient condition that generally results from a bacterial infection (or less commonly a fungal or viral infection). Sepsis is an unusual systemic reaction to what otherwise can be ordinary infection, and likely represents a pattern of response by the immune system to injury. A hyper-inflammatory response is generally followed by an immunosuppressive phase during which multiple organ dysfunction is present and the patient is susceptible to nosocomial infection. Septic patients usually present with malaise, fever, chills, and leukocytosis, which may prompt doctors to evaluate such patients for the presence of bacteria in the bloodstream—typically via bacterial culture testing.

As bacterial culture testing and/or other advanced diagnostic technologies evolve and improve, the speed, accuracy (both sensitivity and specificity), and value of information that can be provided to clinicians continues to improve. Examples of such diagnostic technologies can include, for example, microbial detection, molecular diagnostics, genetic sequencing (e.g., deoxyribonucleic acid (DNA), ribonucleic acid (RNA), next-generation sequencing (NGS), etc.), biomarker identification, and/or the like. Some known culturing methods and/or other diagnostic technologies can be prone to contamination, which can produce results that are inaccurate, distorted, adulterated, falsely positive, falsely negative, and/or otherwise not representative of the actual condition (or in vivo condition) of the patient. In turn, these results can lead to faulty, inaccurate, confused, unsure, low confidence, and/or otherwise undesired clinical decision-making. In some instances, contamination can result from the presence of biological matter—including cells external to the intended sample source and/or other external contaminants—that inadvertently are included in the bodily fluid sample being analyzed. Some known devices and/or systems can be used to reduce the likelihood of contamination and/or adulteration of bodily fluid samples used for testing, which can reduce a likelihood of inaccurate or false diagnostic test results and lead to better patient outcomes. For example, some known devices can be designed to divert and sequester an initial volume of bodily fluid, which is more likely to contain contaminants.

While such diagnostic technologies are capable of providing highly sensitive and/or specific information from tests of clean or unadulterated bodily fluid, the tests often can take between 6 hours to about 5 days or more to yield results. Moreover, known diagnostic technologies are often performed using systems that require highly trained personnel and/or often employ specifically tailored culture protocols for identification of various bacterial species. Such culture methods and/or diagnostic technologies are therefore not suitable for rapid diagnosis and/or efficient screening that may be necessary to treat certain rapidly advancing illnesses. For example, sepsis can rapidly progress to multiple organ dysfunction and/or death, which may prompt doctors to prescribe treatments (e.g., antibiotics) before receiving the results of the diagnostic testing.

Accordingly, a need exists for rapid testing of bodily fluids such as, for example, point of care diagnostic testing using lateral flow assays or other rapid diagnostic technologies. In addition, a need exists for integrating rapid testing (e.g., lateral flow assays) into devices, which can be used to procure additional bodily fluid samples from the patient such as, for example, devices configured to procure bodily fluid samples with reduced contamination.

SUMMARY

Embodiments and methods described herein relate to bodily fluid transfer devices with an integrated flow-based assay (e.g., a lateral flow assay) allowing for initial point of care diagnostic testing. In some embodiments, a system includes a flow-based assay device and a fluid transfer device. The fluid transfer device has an inlet configured to be placed in fluid communication with a bodily fluid source and an outlet configured to be placed in fluid communication with a sample reservoir. The fluid transfer device includes a sequestration chamber and a port in selective communication with the sequestration chamber. The sequestration chamber is configured to be placed in fluid communication with the inlet to receive a first volume of bodily fluid when the fluid transfer device is in a first state. The outlet is configured to be placed in fluid communication with the inlet to receive a second volume of bodily fluid when the fluid transfer device is in a second state. The flow-based assay device is configured to be coupled to the port to receive a portion of the first volume of bodily fluid when the fluid transfer device is in a third state. The flow-based assay device is configured to provide an indication associated with the presence of a target analyte in the portion of the first volume of bodily fluid.

DETAILED DESCRIPTION

Figure 1:
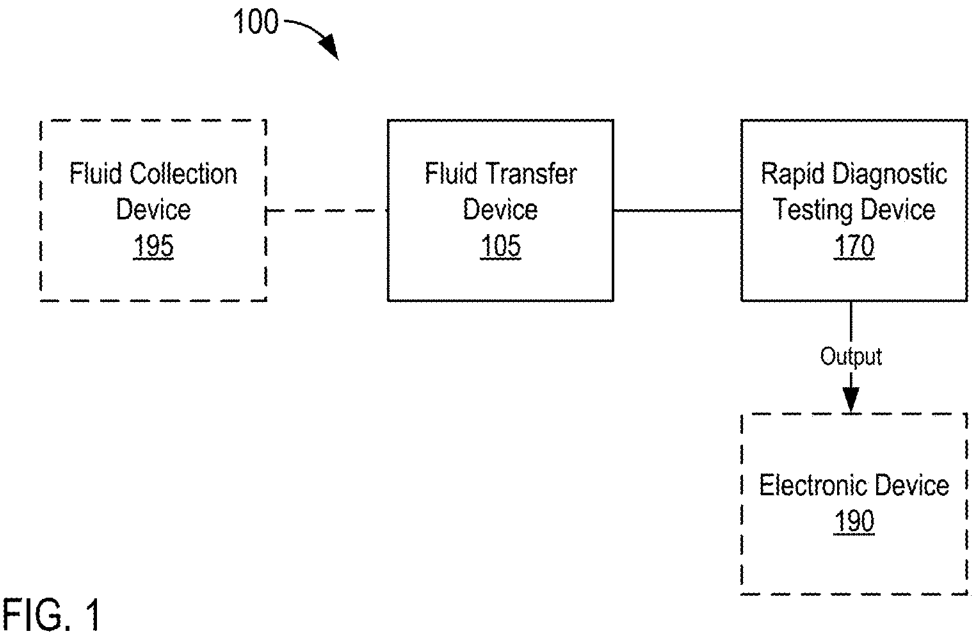
FIG. 1 is a schematic illustration of a fluid transfer and assay system according to an embodiment.

Any of the fluid transfer devices described herein can be configured to receive, procure, and/or transfer a flow, bolus, volume, etc., of bodily fluid. In addition, any of the fluid transfer devices described herein can include an integrated device for performing one or more rapid diagnostic tests on at least a portion of the bodily fluid procured by the fluid transfer device. In some embodiments, the fluid transfer device can be a syringe, a transfer adapter, and/or any other device configured to receive a flow of bodily fluid. In some embodiments, the fluid transfer device can be a fluid diversion and/or sequestration device configured to receive and sequester an initial volume of bodily fluid from subsequent sample volumes used, for example, in culture testing and/or the like. In such embodiments, the integrated device for rapid diagnostic testing can be configured to receive at least a portion of the initial volume of bodily fluid or at least a portion of the subsequent sample volumes. The integrated device for rapid diagnostic testing can be, for example, a lateral flow assay and/or any other suitable diagnostic testing device. The integrated device for rapid diagnostic testing can be used to test the volume of bodily fluid and to provide at least qualitative results, which in turn, can be output on or by the device for visual inspection. In other instances, the testing device can communicate data associated with the results to an electronic device (e.g., via a wired or wireless network), which can then perform any suitable analysis on the data and can, for example, graphically represent at least some of the data on a display of the device (e.g., the qualitative or quantitative test results).

In some implementations, a rapid diagnostic testing device can be included or integrated into a fluid transfer device (e.g., a sample collection device) and used to provide initial test results of a procured bodily fluid. The initial test results can be supplemented with additional tests of the procured bodily fluid such as culture testing. For example, the integrated rapid diagnostic testing device (also referred to herein as "rapid testing device" or "initial testing device") can provide a way for performing relatively fast testing of bodily fluid for the presence of microbes (e.g., Gram-Positive bacteria, Gram-Negative bacteria, fungi, or viruses) or other types of biological matter (e.g., specific types of cells, biomarkers, proteins, antigens, enzymes, blood components, etc.), which can inform clinician decision making regarding treatment strategies. In some implementations, the initial testing device can test for bacteria and/or other infections that can lead to and/or otherwise result in sepsis, thereby allowing the clinician to provide rapid treatment such as broad spectrum antibiotics. Moreover, the fluid transfer devices described herein can procure additional sample volumes that can be used for more sensitive testing such as culture testing or other technologies such as molecular polymerase chain reaction (PCR), magnetic resonance and other magnetic analytical platforms, automated microscopy, spatial clone isolation, flow cytometry, whole blood ("culture free") specimen analysis (e.g., NGS) and associated technologies, morphokinetic cellular analysis, and/or other common, advanced, or evolving technologies used to characterize patient specimens and/or to detect, identify, type, categorize, and/or characterize specific organisms, antibiotic susceptibilities, and/or the like.

In some embodiments, a system includes a flow-based assay device and a fluid transfer device. The fluid transfer device has an inlet configured to be placed in fluid communication with a bodily fluid source and an outlet configured to be placed in fluid communication with a sample reservoir. The fluid transfer device includes a sequestration chamber and a port in selective communication with the sequestration chamber. The sequestration chamber is configured to be placed in fluid communication with the inlet to receive a first volume of bodily fluid when the fluid transfer device is in a first state. The outlet is configured to be placed in fluid communication with the inlet to receive a second volume of bodily fluid when the fluid transfer device is in a second state. The flow-based assay device is configured to be coupled to the port to receive a portion of the first volume of bodily fluid when the fluid transfer device is in a third state. The flow-based assay device is configured to provide an indication associated with the presence of a target analyte in the portion of the first volume of bodily fluid.

In some embodiments, a system includes a fluid transfer device that has an inlet configured to receive a flow of bodily fluid from a bodily fluid source, an outlet configured to be placed in fluid communication with a sample reservoir, a sequestration chamber configured to receive a first volume of bodily fluid, and a port at least temporarily in fluid communication with the sequestration chamber. The fluid transfer device is configured to transition between a first state in which the sequestration chamber is in fluid communication with the inlet to receive a first volume of bodily fluid, and a second configuration in which the outlet is in fluid communication with the inlet to receive a second volume of bodily fluid. The port of the sequestration chamber allows a flow gas to flow through the sequestration chamber as the sequestration chamber receives the first volume of bodily fluid. A flow-based assay device is configured to be coupled to the fluid transfer device in the second state. A portion of the flow-based assay device engages the port when coupled to the fluid transfer device to allow a portion of the first volume of bodily fluid to be transferred from the sequestration chamber to the flow-based assay device. The flow-based assay device is configured to provide an indication associated with the presence of a target analyte in the portion of the initial volume of the bodily fluid.

In some embodiments, a method includes placing an inlet of a fluid transfer device in fluid communication with a bodily fluid source, receiving a first volume of bodily fluid from the inlet and into a sequestration chamber of the fluid transfer device, with a flow controller of the fluid transfer device allowing a flow of gas, but not a flow of bodily fluid, through the flow controller to vent the sequestration chamber during the receiving. Transitioning the fluid transfer device from the first state to a second state after the first volume of bodily fluid is received in the sequestration chamber. In response to the fluid transfer device being in the second state: establishing fluid communication between the inlet and an outlet of the fluid transfer device to allow a second volume of bodily fluid to flow to a sample reservoir in fluid communication with the outlet. Conveying a portion of the first volume of bodily fluid from the sequestration chamber to a sample element of a flow-based assay device fluidically coupled, at least temporarily, to the sequestration chamber; and conveying a buffer solution to the sample element of the flow-based assay device.

In some embodiments, a system includes a fluid transfer device and a lateral flow assay device. The fluid transfer device includes an inlet configured to be placed in fluid communication with a bodily fluid source, an outlet configured to be placed in fluid communication with a sample reservoir, and a sequestration chamber configured to receive an initial volume of bodily fluid. The fluid transfer device configured to be transitioned between (1) a first state in which the sequestration chamber is in fluid communication with the inlet to receive the initial volume of bodily fluid, (2) a second state in which the outlet is in fluid communication with the inlet to receive a subsequent flow of bodily fluid, and (3) a third state in which the lateral flow assay device is coupled to a port in fluid communication with the sequestration chamber. The lateral flow assay device is configured to receive a portion of the initial volume of bodily fluid and to determine the presence of a target analyte in the initial volume of bodily fluid.

As used in this specification and/or any claims included herein, the singular forms "a," "an," and "the" include plural referents unless the context clearly dictates otherwise. Thus, for example, the term "a member" is intended to mean a single member or a combination of members, "a material" is intended to mean one or more materials, and/or the like.

As used herein, "bodily fluid" can include any fluid obtained directly or indirectly from a body of a patient. For example, "bodily fluid" includes, but is not limited to, blood, cerebrospinal fluid, urine, bile, lymph, saliva, synovial fluid, serous fluid, pleural fluid, amniotic fluid, mucus, sputum, vitreous, air, and/or the like, or any combination thereof.

As used herein, the words "proximal" and "distal" refer to the direction closer to and away from, respectively, a user who would place a device into contact with a patient. Thus, for example, the end of a device first touching the body of a patient would be a distal end of the device, while the opposite end of the device (e.g., the end of the device being manipulated by the user) would be a proximal end of the device.

As used herein, the terms "about," "approximately," and/or "substantially" when used in connection with stated value(s) and/or geometric structure(s) or relationship(s) is intended to convey that the value or characteristic so defined is nominally the value stated or characteristic described. In some instances, the terms "about," "approximately," and/or "substantially" can generally mean and/or can generally contemplate a value or characteristic stated within a desirable tolerance (e.g., plus or minus 10% of the value or characteristic stated). For example, a value of about 0.01 can include 0.009 and 0.011, a value of about 0.5 can include and 0.55, a value of about 10 can include 9 to 11, and a value of about 100 can include 90 to 110. Similarly, a first surface may be described as being substantially parallel to a second surface when the surfaces are nominally parallel. While a value, structure, and/or relationship stated may be desirable, it should be understood that some variance may occur as a result of, for example, manufacturing tolerances or other practical considerations (such as, for example, the pressure or force applied through a portion of a device, conduit, lumen, etc.). Accordingly, the terms "about," "approximately," and/or "substantially" can be used herein to account for such tolerances and/or considerations.

As used herein, the terms "first," "initial," and/or "pre-sample" when used to describe a volume of bodily fluid can be used interchangeably to describe an amount, portion, or volume of bodily fluid that is collected, diverted, sequestered, tested, etc. prior to procuring a "sample" volume. A "first," "initial," and/or "pre-sample" volume can be a predetermined, defined, desired, and/or given amount of bodily fluid. For example, a predetermined and/or desired pre-sample volume of bodily fluid such as blood can be a drop of blood, a few drops of blood, a volume of about 0.1 milliliter (mL), about 0.2 mL, about 0.3 mL, about 0.4 mL, about 0.5 mL, about 0.6 mL, about 0.7 mL, about 0.8 mL, about 0.9 mL, about 1.0 mL, about 2.0 mL, about 3.0 mL, about 4.0 mL, about 5.0 mL, about 6.0 mL, about 7.0 mL, about 8.0 mL, about 9.0 mL, about 10.0 mL, about 20.0 mL, about 50.0 mL, and/or any volume or fraction of a volume therebetween. In other instances, a pre-sample volume can be greater than 50 mL or less than mL. As a specific example, a predetermined and/or desired pre-sample volume can be between about 0.1 mL and about 5.0 mL. As another example, a pre-sample volume can be, for example, a volume or combined volume of any number of lumen (e.g., the lumen of a needle and/or the combined lumen that form at least a portion of a flow path from the bodily fluid source to an initial collection chamber, portion, reservoir, etc.). As yet another example, a pre-sample volume can be, for example, a volume of bodily fluid sufficient to perform initial or pre-sample testing such as, for example, rapid diagnostic testing using lateral flow assay and/or any other rapid testing device.

As used herein, the terms "second," "subsequent," and/or "sample" when used to describe a volume of bodily fluid can be used interchangeably to describe an amount, portion, or volume of bodily fluid that is collected after collecting a first, initial, and/or pre-sample volume of bodily fluid. A "second," "subsequent," and/or "sample" volume can be either a random volume or a predetermined or desired volume of bodily fluid collected after collecting, diverting, sequestering, and/or testing a pre-sample volume of bodily fluid. In some instances, a desired sample volume of bodily fluid can be about 10 mL to about 60 mL. In other instances, a desired sample volume of bodily fluid can be less than 10 mL or greater than 60 mL. In still other instances, a desired sample volume can be at least partially based on one or more tests, assays, analyses, and/or processes to be performed on the sample volume.

In some implementations, a second, subsequent, and/or sample volume of bodily fluid can be used in one or more sample or diagnostic tests such as, for example, culture testing and/or the like. In some instances, collecting a "sample" volume of bodily fluid subsequent to the collection, sequestration, isolation, and/or testing of a "pre-sample" volume of bodily fluid can result in a lower likelihood of the sample volume containing contaminants such as dermally residing microbes and/or the like. Accordingly, the sample volume of bodily fluid can be suitable for sensitive testing that may otherwise be prone to inaccurate results due to contamination.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polysiloxanes (silicones), polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

Referring now to the drawings, FIG. 1 is a schematic illustration of a fluid transfer and assay system 100, according to an embodiment. While various components, elements, features, and/or functions may be described below, it should be understood that they have been presented by way of example only and not limitation. Those skilled in the art will appreciate that changes may be made to the form and/or features of the fluid transfer and assay system 100 without altering the ability of the fluid transfer and assay system 100 to perform the function of procuring bodily fluid samples and providing rapid diagnostic testing methods, as described herein.

The fluid transfer and assay system 100 (also referred to herein as "system") can include at least a fluid transfer device 105 and a rapid diagnostic testing device 170. In some implementations, the system 100 can optionally include at least one electronic device 190 and/or at least one fluid collection device 195.

The fluid transfer device 105 (also referred to herein as "transfer device") can be any suitable shape, size, and/or configuration, as described herein with reference to specific embodiments. In some implementations, the transfer device 105 can be configured to withdraw bodily fluid (e.g., blood) from a patient and into the transfer device 105. In addition, the transfer device 105 can be configured to transfer at least some of the withdrawn bodily fluid to one or more other devices, reservoirs, containers, vials, machines, tests, assays, etc., such as the rapid diagnostic testing device 170 and/or one or more of the optional fluid collection devices 195.

In some embodiments, the transfer device 105 can be configured to transfer, direct, and/or divert certain amounts or volumes of the bodily fluid into (or through) one or more portions of the transfer device 105, and subsequently transfer such amounts or volumes into one or more devices coupled to or integrated with the transfer device 105, into one or more sample reservoirs, containers, bottles, etc., and/or the like. For example, the transfer device 105 can be configured to transfer a first portion, amount, or volume of bodily fluid into or through a first or sequestration portion of the transfer device 105 and subsequently transfer a second portion, amount, or volume (e.g., a subsequent amount) of bodily fluid into a second or sampling portion of the transfer device 105. In some embodiments, the transfer device 105 and/or the sequestration portion of the transfer device 105 can be configured to sequester the first amount of bodily fluid (e.g., within the sequestration portion of the transfer device 105) from the subsequent amount of bodily fluid, as described in further detail herein with reference to specific embodiments. In some implementations, the transfer device 105 can be configured to transfer at least some of the first amount of bodily fluid (e.g., contained in the sequestration portion of the transfer device 105) to the rapid diagnostic testing device 170 and at least some of the second amount of bodily fluid to one or more of the optional fluid collection devices 195.

The rapid diagnostic testing device 170 (also referred to herein as "rapid testing device" or simply "testing device") can be any suitable shape, size, and/or configuration, as described herein with reference to specific embodiments. In some embodiments, the rapid testing device 170 can be removably coupled to the transfer device 105 or any suitable portion thereof (e.g., an inlet portion, an outlet portion, a sequestration portion, a sampling portion, and/or any other suitable portion). In other embodiments, the rapid testing device 170 can be integrated into the transfer device 105. For example, the transfer device 105 and the rapid testing device 170 can be unitarily or monolithically formed and/or otherwise integrated. In still other embodiments, the transfer device 105 can include and/or can form a port, adapter, and/or receiving portion to which the rapid testing device 170 can be coupled or into which the rapid testing device 170 can be inserted to establish fluid communication therebetween. In some such embodiments, coupling the rapid testing device 170 to the transfer device 105 can be operable to transition one or more flow controllers, valves, septa, ports, seals, etc. from a closed or sealed state to an open state to allow fluid communication between the transfer device 105 and the testing device 170.

In some implementations, the rapid testing device 170 can be configured to receive the first amount of bodily fluid from the transfer device 105 and to use the first amount of bodily fluid to perform one or more tests, assays, and/or diagnostic procedures. For example, the rapid testing device 170 can be a chromatographic lateral flow immunoassay that can test for any suitable analytes, biomarkers, proteins, molecules, particles, and/or the like. Chromatographic lateral flow immunoassays (referred to herein as "lateral flow assays" or "LFAs") are typically nitrocellulose-based devices configured to detect the presence of a target analyte in a sample (e.g., a biologic sample and/or bodily fluid sample such as blood, urine, etc.). In general, an LFA includes a series of capillary beds, such as pieces of porous paper, microstructured or sintered polymer(s), and/or the like that can be disposed in desired positions and/or arrangements on a substrate to direct a flow of a sample (e.g., at least some of the first amount of bodily fluid) along a portion of the LFA.

LFAs can be used for a broad range of applications where it is desirable to have a relatively fast, easy to use, and low-cost way for rapid antigen detection. LFAs are typically performed with little or no sample or reagent preparation, which can allow for usable test results in as little as a few minutes (or longer if more sensitive test results are desirable). Moreover, in some implementations, an LFA can be configured to test for analytes, and/or biomarkers that are produced by the human body in response to in vivo conditions (e.g., infections such as sepsis), which in turn, can mean that such an LFA has a relatively low sensitivity to contaminants (e.g., dermally residing microbes or the like) that may be included in the first amount of bodily fluid withdrawn from a patient via the transfer device 105.

Typically, two types of LFAs are used depending on a size and/or a number of binding sites on the target analyte. Specifically, competitive LFAs are generally used when testing for smaller analytes while sandwich LFAs are generally used when testing for larger analytes. For context, a home pregnancy test is a well-known sandwich lateral flow assay. In some instances, it may be desirable to use a sandwich LFA to test for antigens, analytes, and/or biomarkers associated with, for example, sepsis and/or other infectious conditions within a sample of bodily fluid such as blood. While the embodiments described herein include and/or implement a sandwich LFA, it should be understood that the embodiments are not limited thereto. For example, any of the embodiments described herein can use and/or implement a competitive LFA and/or any other suitable rapid diagnostic testing device.

Figure 2:
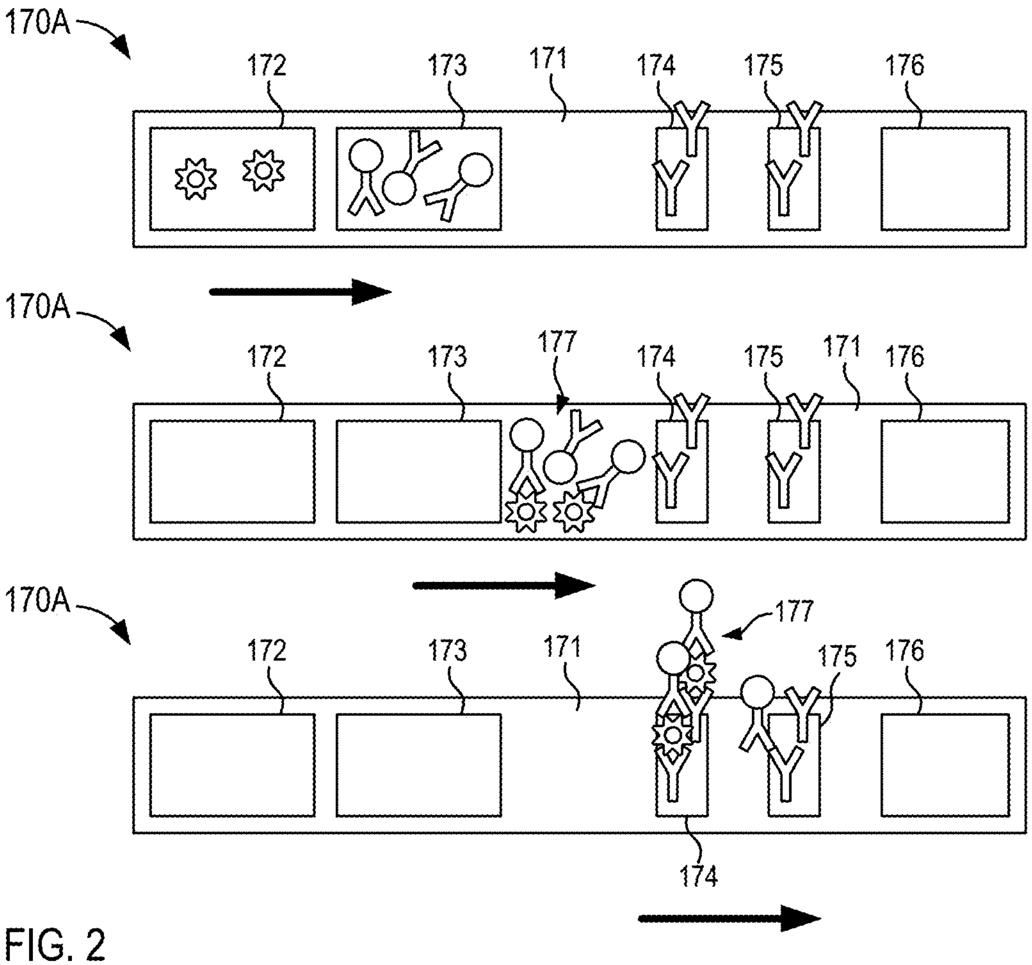
FIG. 2 is a schematic illustration of a lateral flow assay device according to an embodiment.

A schematic example of a sandwich LFA 170A is shown in FIG. 2 for context. The sandwich LFA 170A (referred to herein as "LFA") includes a substrate 171 on which a sample element 172, a conjugate element 173, a capture element 174, a control element 175, and a wick 176. The substrate 171 can be any suitable shape, size, and/or configuration. For example, the substrate 171 can be a rectangular backing card or strip of constant width and a predetermined length capable of providing sufficient surface area for accommodating the various components of the LFA 170A. The substrate 171 can be made of a semi-rigid polymer designed to deliver uniformity and lay-flat properties. The substrate 171 can include one or more pressure sensitive adhesives configured to facilitate attaching the various components of the LFA 170A, as further described herein.

As shown, the sample element 172 is generally disposed at one end of the substrate and is configured to receive a sample volume. The sample element 172 can be a pad that provides a surface to receive a sample of blood and/or other biofluids for analysis and facilitates transport of the sample to other components of the lateral flow test strip in a smooth, continuous and homogeneous manner. The sample element 172 can be any suitable shape, size, and/or configuration. The conjugate element 173 is disposed adjacent to the sample element 172 in a downstream direction. The conjugate element 173 contains a dried matrix (e.g., a salt-sugar matrix) configured to include desired bio-active particles. The bio-active particles contained in the matrix include specific antibodies and/or affinity reagents (e.g., DNA aptamers, protein binders, etc.) that have been immobilized on or in the conjugate element 173. The antibodies and/or affinity reagents can be selected based on the target molecule (e.g., an antigen or analyte), that the LFA 170A is configured to detect. In addition, the antibodies and/or affinity reagents are directly or indirectly conjugated to a molecule configured to allow detection. For example, the antibodies can be labeled with a colored particle (e.g., latex having a blue color, colloidal gold having a red color, and/or any other suitable particle), a fluorescent particle, a magnetic particle, an enzyme for subsequent signal generation, and/or the like. Thus, the labeled antibodies can bind to the desired antigens or analytes, thereby producing a labeled or target analyte 177 that can be detected in other portions or by other elements of the LFA 170A.

The capture element 174 is disposed adjacent to and/or downstream of the conjugate element 173 and contains particles or molecules that have been immobilized in or on the capture element 174. The particles or molecules can be configured to bind to the labeled analyte 177, thereby capturing or immobilizing the labeled analyte 177 in or on the capture element 174. As a concentration of the captured and/or immobilized labeled analyte 177 increases (e.g., a number of molecules within the capture element 174 increases), the optical density of the detection molecule (e.g., colored label) also increases. In this manner, the LFA 170A is configured to present a discrete colorimetric signal line, region, or strip to indicate a presence of the target analyte in the sample volume (e.g., a positive test result).

The control element 175 is disposed adjacent to and/or downstream of the capture element 174. The control element 175 contains particles or molecules that have been immobilized in or on the control element 175. In contrast to the capture element 174, the particles or molecules contained in the control element 175 can configured to bind to multiple different particles such as, for example, the labeled analyte 177, the labeled bio-active particles that are not bound to an antigen, and/or the like. Accordingly, the control element 175 can be configured to bind to and/or otherwise immobilize labeled particles not otherwise immobilized in or on the capture element 174. Thus, the control element 175 can present a colored portion or strip, which can be used to show that a reaction occurred and/or that the test was performed. For example, if a target analyte is not present in a sample volume, it may be desirable to confirm that the assay was performed properly and that the negative result (no colored strip presented on or by the capture element 174) is indicative of the condition of the sample volume and not a malfunction of the LFA 170A. The wick 176 is disposed adjacent to and/or downstream of the control element 175 and is configured to absorb or wick portions of the sample that have not been immobilized in or on the capture element 174 and/or the control element 175.

Assay

The LFA 170A can be used to test for the presence of any suitable target analyte, biomarker, molecule, particle, etc. in a sample volume (e.g., a blood sample or any other suitable sample of bodily fluid). For example, any of the embodiments described herein can include and/or implement an LFA (e.g., the LFA 170A) and/or any other suitable flow-based rapid diagnostic system configured to test for the presence of specific analytes or biomarkers that can provide information used to diagnose a patient condition such as, for example, sepsis.

For example, blood lactate can be a biomarker used in the clinical diagnosis and management of sepsis. In some instances, a host of other biomarkers can be used as an alternative to or in addition to lactate to guide clinical decision making. A non-exhaustive list of suitable biomarkers can include pro-inflammatory cytokines and/or chemokines, which are associated with the hyper-inflammatory phase of sepsis; C-reactive protein and/or procalcitonin (PCT), which are synthesized in response to infection and inflammation; biomarkers associated with the activation of neutrophil and/or monocytes; anti-inflammatory cytokines, which are associated with the immunosuppressive phase of sepsis; and/or alterations of the cell surface markers of monocytes and/or lymphocytes. In some instances, combinations of pro- and anti-inflammatory biomarkers in a multiplexed LFA can be used, for example, to identify patients who are developing severe sepsis before substantial organ dysfunction. In some instances, one or more aptamers can be synthesized to target specific pro-inflammatory biomarkers, anti-inflammatory biomarkers, and/or any other suitable biomarker such as any of those described herein.

Lactate

In some implementations, any of the embodiments described herein can be used to detect lactate biomarkers, PCT biomarkers, and/or any other suitable biomarker described herein associated with and/or otherwise used to identify sepsis. For example, in some implementations, the rapid testing device 170 can be configured to test blood lactate levels in a sample of bodily fluid (e.g., blood) using, for example, a portable blood gas analyzer. In other implementations, the rapid testing device 170 can be an LFA (e.g., the LFA 170A) configured to test for blood (e.g., whole blood, serum, etc.) lactate biomarkers (e.g., antigens). For example, the effectiveness of using serum lactate levels in the diagnosis of sepsis is shown below in Table 1, which presents the results of a study of acute hospital mortality according to serum lactate levels in septic patients requiring vasopressors (e.g., an agent that results in blood vessel constriction).

TABLE 1

| | Initial Serum Lactate Level (mmol/L) | | | |
|---|---|---|---|---|
| Hospital Mortality | <4 | 4-8 | >8 | P value |
| 24-hour mortality, n (%) | 1 (10.0) | 14 (35.0) | 19 (52.8) | 0.011 |
| 48-hour mortality, n (%) | 3 (30.0) | 26 (65.0) | 26 (72.2) | 0.033 |

Lactic acid is the end product of anaerobic breakdown of glucose in tissues, which can dissociate into lactate, the hydroxy monocarboxylic acid anion that is the conjugate base of lactic acid arising from the deprotonation of the carboxy group. Evolution of lactate in the body takes place when the energy demand by tissues is not met by adequate aerobic respiration. Lactate can be transported in the blood to the liver, where it is converted back to glucose via the Cori cycle. However, without adequate clearance of lactate by the liver and kidney the accumulated concentration of lactate can result in lactic acidosis. Clinically, causes of acidosis can be classified as type A disorders, in which there is a decreased tissue oxygenation such as with sepsis, and type B disorders causes by certain drugs and/or toxins along with systemic disease, among others. Medical evidence suggests patients with persistently elevated levels of lactate have increased morbidity and mortality. Excess lactate in the body can also cause hemorrhage, respiratory failure, trauma, seizures, ischemia, renal issues, hepatic disease, tissue hypoxia, shock, blood loss, anemia, among others. Therefore, lactate monitoring is of prime importance to diagnose and evaluate health concerns which occur in oxygen deficit situations (i.e., situations where lactate levels in the body increase beyond the accepted values). Concentrations of lactate in the blood for healthy, unstressed individuals have been reported to be in the range of 0.1-1.0 millimolar (mM). In contrast, critically ill individuals, such as those presenting with severe sepsis or septic shock, can exhibit concentrations higher than 4 mM.

Lactate can exist as one of two optical isomers, L-lactate and its mirror image, D-lactate. Analytical methods used to detect and quantify lactate include High Performance Liquid Chromatography (HPLC), fluorimetry, colorimetric test, chemiluminescence, and magnetic resonance spectroscopy. Although these methods can provide accurate results, they suffer from drawbacks such as time-consuming sample preparation, use of expensive instrumentation, and the need of trained personnel. Consequently, the use of these analytical methods to detect and quantify lactate in biofluids is better suited to centralized laboratories, and their implementation as point of care diagnostic tool can be limited.

Detection of lactate levels in biofluids including blood and/or plasma can alternatively be achieved with the use of enzymes. These enzymes can be immobilized on a solid surface or support (e.g., biosensor) to provide reactive sites which catalyze lactate chemical reactions by stabilizing transition reaction states or decreasing the activation energy of the particular lactate chemical reactions, producing one or more species that can be monitored to correlate its evolution with the concentration of lactate. For example, L-lactate can be detected using enzymes such as L-lactate oxidase (LOD) and L-lactate dehydrogenase (LDH). LOD is a globular flavoprotein that can be obtained from a variety of bacterial sources such as *Pediococcus, Aerococcus, viridans*, and *Mycobacterium*. The source of LOD can have an impact on the range of pH that the enzyme can show sufficient catalytic activity, exhibiting typical ranges between 4 and 9. LOD, being a member of the flavin mononucleotide (FMN) family, employs FMN as a cofactor to catalyze the oxidation of hydroxyl acids in its reactions involving glycolate oxidase, L-lactate, monooxygenase, flavocytochrome b2, long chain α-hydroxyl acid oxidase, and L-mandelate dehydrogenase. LOD can be immobilized on a solid support and be exposed to biofluids such as blood and plasma for detecting the presence of L-lactate. LOD can catalyze the oxidation of L-lactate to pyruvate (PA) in the presence of dissolved oxygen, producing reduced LOD and hydrogen peroxide ($H_2O_2$) as a byproduct. The hydrogen peroxide produced from lactate oxidation can be accurately quantified by a secondary chemical and/or electrochemical reaction. For example, hydrogen peroxide produced by during the oxidation of lactate in the presence of LOD enzymes can be electrochemically reduced or oxidized to generate an electrical signal that can be monitored by an electrode. The reduced LOD enzyme can be then re-oxidized in a second reaction step on the electrode, as shown in reaction scheme below:

$$\text{L-lactate} + O_2 \xrightarrow{\text{LOD}} \text{Pyruvate} + H_2O_2$$

$$H_2O_2 \longrightarrow O_2 + 2H^+ + 2e^-$$

Similar to LOD, LDH enzymes can be used to detect and quantify the presence of L-lactate in various biofluids. LDH is a quaternary protein that can be found in animals, plants, and prokaryotes. LDH is present thought tissues and is released during tissue damage. LDH enzymes include five different isozymic forms, distinguished by slight structural differences. Depending on the source, LHD enzymes are known to be stable over a relatively narrow pH range of 5-8, and more particularly, a pH range of around 7.2-7.4. LDH can also catalyze the reaction of L-lactate to pyruvate (PA) through its cofactor, Nicotinamide adenine dinucleotide (NAD), which can exist in an oxidized ($NAD^+$) and reduced (NADH) form. During the reaction, LHD converts L-lactate into Pyruvate (PA) and $NAD^+$ to NADH. Detection of lactate with LDH enzyme can be then achieved by a secondary reaction, as described above with reference to the detection of L-lactate with LOD enzymes. For example, NADH can be electrochemically oxidized under the influence of an applied electrical potential generated with an electrode, with the current generated being proportional to the L-lactate concentration, as shown in reaction scheme below:

$$\text{L-lactate} + NAD^{+} \xrightarrow{\text{LDH}} \text{Pyruvate} + NADH + H^{+}$$

$$NADH \xrightarrow{\nabla E} NAD^{+} + H^{+} + 2e^{-}$$

The use of enzymes to detect lactate in biofluids via lactate enzymatic oxidation relies on the conversion of lactate to one or more byproducts such as NADH and hydrogen peroxide ($H_2O_2$) that can be accurately quantified by means of a secondary reaction, as described above. The secondary reaction frequently involves an electrochemical transformation that generates a transient electric current proportional to the amount of lactate present in the sample, carried out at the surface of an electrode (e.g., electrochemical techniques for lactate sensing). Alternatively, the byproducts of the enzymatic reactions of lactate can be quantified by photo transfer processes (e.g., electro-chemiluminescence and fluorescence techniques for lactate sensing), as further described herein.

Biosensors that rely on electrochemical techniques for detection of lactate (i.e., electrochemical biosensors) use enzymes immobilized onto a supporting substrate located close to or in the vicinity of an electrode surface. The performance characteristics of electrochemical biosensor can vary greatly depending on the source of the enzyme, environmental conditions including pH and temperature, the methods used to immobilize the enzyme to the biosensor, the chemical nature of the matrix or support used to immobilize the enzyme and/or the electron transfer mechanism. The enzymes can be immobilized according to different methods, and their reactivity depends on their interactions with the support, the nature of the enzymes, and the presence of adsorbed species, mediators and additives. Common enzyme immobilization techniques include physical adsorption, entrapment behind a dialysis membrane or polymeric film, covalent coupling through a cross linking agent, and incorporation within the bulk of a carbon composite matrix.

Challenges associated with the immobilization of enzymes include reproducibility, stability, and deactivation due to evolution and/or accumulation of inhibitors and or fouling species. For example, LOD enzymes immobilized via physical adsorption on biosensors comprising Au electrodes can exhibit stability losses of 50% after just 1 month of storage, whereas LOD enzymes immobilized in mesoporous silica using a polymer matrix of polyvinyl alcohol (PVA) can exhibit 98% of their initial activity after 9 months. As a result, the development of sensors that use LOD enzymes to detect lactate requires identifying appropriate immobilization techniques, suitable matrix support, and used and/or storage environmental conditions, such that the activity of the enzyme or shell life can be retained for long periods of time.

Electrochemical biosensors of lactate detection typically include an apparatus comprising two or three electrode sensing platforms. Accurate measurement of lactate often includes use of a reference electrode (commonly made of $Ag/AgCl_2$), that is kept at a close proximity of the working electrode in order to maintain a stable and known potential. The working electrode serves as a transducer, while the counter electrode establishes a path to pass the current due to the potential changes at the working electrode. Common approaches to measure the electrical signals produced during detection of lactate include cyclic voltammetry, amperometry, and potentiometry. Electrochemical biosensors can offer high sensitivity, wide linear range and rapid response. However, their use presents limitations due to complex experimental set up, passivation of the system due to fouling agents, and signal reduction and interference due to competing reactions. For example, the electrochemical quantification of hydrogen peroxide ($H_2O_2$) produced during the enzymatic oxidation of L-lactate over LOD enzymes require high oxidation potentials, which leads to interferences caused by other electro-oxidizable species.

Lateral flow assays (LFA) configured to test for blood (e.g., whole blood, serum, etc.) lactate biomarkers (e.g., antigens) provide an alternate tool to facilitate and/or aid in the diagnosis of sepsis. As described above with reference to FIG. 2, an LFA can be performed over a strip comprising one or more components assembled over a plastic backing laminate or substrate 171. The components of an LFA configured for quantifying lactate in blood and/or other biofluids can include at least a sample element 172 and a conjugate element 173.

The sample element 172 can be a pad that provides a surface to receive a sample of blood and/or other biofluids for analysis and facilitates transport of the sample to other components of the lateral flow test strip in a smooth, continuous and homogeneous manner, as described above. The sample element 172 can be any suitable shape and/or size. In some embodiments the shape of the sample element 172 can be a rectangular strip configured to adsorb and receive a volume of a sample of blood and/or other biofluids. In other embodiments, the shape of the sample element 172 can be a rectangular strip in which one of its ends includes a region having larger dimensions than the width of the strip to facilitate pipetting a volume of the sample of blood and/or other biofluids. For example, the sample element 172 can be a rectangular strip that includes circular shaped region attached to one of the strip's end. The circular shaped region of the sample element 172 can provide a larger surface area for receiving the sample of blood and/or other biofluids via a micropipette. Alternatively, in some embodiments, the sample element 172 can include a large diameter circular shaped region with various rectangular strips stemming from the center of the circular shaped region in the radial direction. Each rectangular strip can facilitate transport of a portion of the sample of blood and/or other biofluids to other components of the lateral flow test strip for simultaneous detection of multiple biomarkers (i.e., multiplexing), and/or for replicating assays for validation purposes.

The sample element 172 can be disposed onto the surface of a plastic backing laminate to provide mechanical support to the LFA. In some embodiments, the sample element 172 can include an adhesive coated on one surface of the sample pad to facilitate attachment to a plastic backing laminate. The shape and dimensions of the sample element 172 can be predetermined such that the sample element can be disposed onto a plastic backing laminate. The thickness of the sample element 172 can be selected to facilitate adhesion of the sample element 172 to the plastic backing laminate while maintaining the mechanical structure of the pad. Additionally, the thickness of the sample element 172 can be selected to accommodate large volumes of blood and/or other biofluids, preventing oversaturation of the sample on the pad, and channeling to the plastic backing laminate. For example, in some embodiments, the thickness of the sample element 172 can between 0.18 mm and 0.34 mm.

The sample element 172 can be made of cellulose, nitrocellulose, glass fiber, and/or any other suitable material. In some embodiments, the sample element 172 can be made of a cellulose membrane and/or a chromatographic paper configured to facilitate linear flow rates of about 3 to 5 mm/min. The sample element 172 can also include one or more chemical reagents configured to pre-treat the sample prior to its transportation to other downstream components. In some embodiments, the surface of the sample element 172 can be impregnated with an aqueous buffer solution that provide an environment with controlled pH. In some embodiments, the surface of the sample element 172 can be impregnated with a buffer solution including, but not limited to phosphate-buffered saline (PBS), 2-ethanesulfonic acid (MES), tris (hydroxymethyl)aminomethane (TRIS), piperazine-N, N'-bis (PIPES), 3-morpholinopropane-1-sulfonic acid (MOPS), 2-[4-(2-hydroxyethyl)piperazin-1-yl] ethanesulfonic acid (HEPES), [tris(hydroxymethyl)methylamino] propanesulfonic acid (TAPS), N-Cyclohexyl-2-aminoethanesulfonic acid (CHES), and/or N-cyclohexyl-3-aminopropanesulfonic acid (CAPS).

In some embodiments, the sample element 172 can include one or more components configured to capture and separate species present in the blood and/or other biofluid that can cause interference with the LFA assay. For example, in some embodiments, the sample element 172 can include one or more regions configured to separate red blood cells present in a blood and/or other biofluid sample. In some instances, the region(s) configured to separate blood cells can be one or more separate pads that can be disposed over the sample element 172. In other embodiments, the blood separation region can be a pad located adjacent to the sample element 172. In some instances, the blood separation pad can include one or more layers such as a polyester matrix and a composite matrix, designed to have asymmetric morphologies with different porosities and pore size distributions that facilitate capture of the cellular components of blood (i.e., red cells, white cells, and platelets) in the larger pores, while allowing flow of plasma downstream trough smaller size pores.

The conjugate element 173 of an LFA for detection and quantification of lactate from blood and/or other biofluid samples can be a pad located adjacent downstream to the sample element 172. The conjugate element 173 can contain a dried matrix (e.g., a salt-sugar matrix) that includes bio-active species that can react with lactate and produces species that can be detected by colorimetric methods, as further described herein. The conjugate element 173 can be configured to accommodate one or more bio-active species that can be released upon contact with the moving liquid sample deposited on the upstream sample element 172. As described above with reference to the sample element 172, the conjugate element 173 can be a pad of any suitable shape and/or size. In some embodiments the shape of the conjugate element 173 can be a strip having a size and/or shape substantially similar to those of the sample element 172. In some embodiments, the conjugate element 173 and the sample element 172 can be made of a single pad and can be disposed at opposite ends thereof, and optionally attached to the surface of a plastic backing laminate to provide mechanical support to the LFA. In yet another embodiment, the conjugate element 173 and the sample element 171 can be made of a single pad that includes a rectangular strip in which a first end of the strip comprises a region having a larger dimension than the width of the strip to provide an area to accommodate the bio-active species for lactate oxidation and colorimetric detection, and a second end of the strip, opposite to the first end, having a larger dimension than the width of the strip to provide an area to accommodate a volume of a sample of blood and/or other biofluids. Alternatively, in some embodiments, the conjugate element 173 can be include multiple rectangular strips that are coupled to a large diameter circular shaped region in the radial direction, with the large diameter circular shaped region being configured to accommodate the sample element 171. In this configuration, each conjugate element 173 can facilitate detection of multiple biomarkers (i.e., multiplexing) present in a portion of the sample of blood and/or other biofluid, and/or for replicating assays for validation purposes.

The conjugate element 173 can include a dried matrix configured to include desired bio-active species for detection and quantification of lactate in a sample of blood and/or other biofluid. For example, in this embodiment, the matrix of the conjugate element 173 can include both a detection enzyme and a quantification enzyme. The detection enzyme can be configured to exhibit high activity and selectivity for the catalytic oxidation of lactate, producing one or more byproducts which can be monitored by means of a secondary chemical reaction to quantify the concentration of lactate present in the sample. For example, in some embodiments, the matrix of the conjugate element 173 can include a detection enzyme such as L-lactate oxidase (LOD). In other embodiments, the matrix of the conjugate element 173 can include other suitable detection enzymes such as such as L-lactate dehydrogenase (LDH). The one or more detection enzymes can be loosely deposited on the surface of the conjugate element 173 pad such that they can be dissolved in a volume of a sample of blood and/or other biofluids flown from the sample element 172.

The quantification enzyme can be configured to exhibit high activity and selectivity for the stoichiometric conversion of one or more species produced during the enzymatic oxidation of lactate, generating a signal that can be quantified. In some embodiments, the dried matrix can include one or more haem-containing enzymes such as catalases and/or peroxidases that can catalyze redox reactions with hydroperoxides such as hydrogen peroxide ($H_2O_2$) produced during lactate oxidation. The haem-containing enzyme can be, for example, a horseradish peroxidase which can catalyze the redox reaction of hydrogen peroxide ($H_2O_2$) and 3,3'-diaminobenzidine (DAB), producing a dark brown insoluble product that can be detected and quantified by colorimetry.

While the LFA 170A is described above as also including the capture element 174, a control element 175, and a wick 176, in this embodiment, detection of lactate can be performed, for example, on or at the conjugate element 173. Thus, the LFA need not include a separate capture element, control element, and/or wick.

In some embodiments, for example, the LFA can be coupled to an optical device such as an CMOS or a CCD camera configured to collect images of the 3,3'-diaminobenzidine (DAB) dark brown precipitate resulted from oxidation with hydrogen peroxide, to determine the concentration of lactate originally present in the sample. For example, in some embodiments, the conjugate element 173 of the LFA can imaged by the camera of a peripheral device such as a smartphone or a dedicated optical detector, and the intensity of the images can be analyzed by image software in order to estimate the concentration of DAB precipitate, the concentration of hydrogen peroxide, and thus the concentration of lactate originally present in the sample. In some embodiments, the concentration of lactate present in the sample can be determined by (1) recording images of the DAB brown precipitate, (2) calculating the grayscale mode value with the aid of image processing software, and (3) correlating the grayscale mode value with concentration of lactate present in samples of know lactate content. The range of grayscale mode value that an image can assume is zero to 255, with values closer to zero corresponding to darker images, and values closer to 255 corresponding to lighter images.

Later Flow Assays (LFA) configured to detect lactate in blood and/or other biofluids can overcome certain shortcomings observed with lactate detection approaches that rely on electrochemical reactions to quantify the amount of hydrogen peroxide ($H_2O_2$) produced upon lactate oxidation. As described above, the enzymatic reaction of hydrogen peroxide ($H_2O_2$) with 3,3'-diaminobenzidine (DAB) produces a brown-colored precipitate that is insoluble in the sample of blood and/or biofluid and that can be quantify by optical methods such as colorimetry. Furthermore, the reaction of hydrogen peroxide and DAB proceeds under pH and temperature conditions similar to those required for the oxidation of lactate. Thus, the use of additives in the dried matrix of the LFA can protect the both the detection enzyme and the quantification enzyme from decomposition, facilitating storage for periods of time as long as 9 months, as further described herein. In contrast, electrochemical methods to detect and quantify lactate typically require use of high oxidation potentials to convert hydrogen peroxide to an electrical signal Those potentials can frequently trigger interfering reactions of other electro-oxidizable species present in the sample of blood and/or biofluid, which leads to inaccurate results. Additionally, the immobilization of enzyme to a solid surface can present several challenges including (1) the need for complex and/or time-consuming fabrication and characterization methods, and reduced stability of the enzyme during storage.

In some embodiments, the detection enzyme and the quantification enzyme can be contained in the dried matrix in the presence of one or more chemical reagents and/or stabilizing additives configured to preserve the activity and stability of the enzymes during storage as well as during oxidation of lactate in the blood and/or other biofluid samples. For example, the dried matrix can include a weak acid or base (e.g., a buffer agent) that can be dissolved in the blood and/or other biofluid sample, and can dissociate in the sample to establish an equilibrium between their acid species and their conjugates, maintaining the pH of the sample within a range of values in which the enzymes exhibit high catalytic activity. In some embodiments, the dried matrix can include one or more buffer agents such as phosphate-buffered saline (PBS), 2-ethanesulfonic acid (MES), tris (hydroxymethyl)aminomethane (TRIS), piperazine-N, N'-bis (PIPES), 3-morpholinopropane-1-sulfonic acid (MOPS), 2-[4-(2-hydroxyethyl)piperazin-1-yl] ethanesulfonic acid (HEPES), [tris(hydroxymethyl)methylamino] propanesulfonic acid (TAPS), N-Cyclohexyl-2-aminoethanesulfonic acid (CHES), and/or N-cyclohexyl-3-aminopropanesulfonic acid (CAPS)

In some embodiments, the dried matrix can include a polysaccharide such as chitosan, a non-toxic biocompatible biopolymer which can provide antimicrobial activity, and antioxidant activity to preserve the chemical integrity of the enzymes for extensive periods of time. In some embodiments, the chitosan stabilizer can be accompanied by one or more reagents configured to increase the solubility of chitosan in the sample of blood and/or other biofluid. For example, in some embodiments, the dried matrix can include chitosan and a weak organic acid such as formic acid, acetic acid, and/or propionic acid, suitable to increase the solubility of chitosan in a volume of blood and/or a biofluid. In some embodiments, the dried matrix can include a combination of additives including chitosan, acetic acid, and/or buffer agents, adsorbed on the surface of the conjugate 173 and configured to be dissolved in a volume of blood and/or biofluid transported from the sample element 170.

The Lateral flow assays (LFA) configured to test for lactate in blood and/or other biofluids as described above can detect lactate present in various samples including buffer solutions, serum, plasma and/or whole blood. More specifically, in some embodiments, the LFA can exhibit a dynamic range of detectable lactate of 2-6 (mM), and a sensitivity equal to or higher than 0.5 mM lactate in buffer and/or serum samples. In some embodiments, the LFA can exhibit a cutoff lactate concentration of 2 mM and 4 mM in buffer/serum. The total time required to obtain lactate results using the LFA configured for lactate detection can be about 10 min. The LFA configured for lactate detection can remain relatively stable over time with a degradation occurring primarily in the first week of test, when subjected to accelerated degradations studies at 37 C. More specifically, the LFA configured for lactate detection can remain stable for up to 4 weeks at 37 C, showing small changes in the signal response, supporting the idea that the LFA assay will remain viable for an extended period of time.

Procalcitonin

In some implementations, the rapid testing device 170 can be an LFA (e.g., the LFA 170A) configured to test for the PCT biomarker. For example, the effectiveness of using the serum PCT biomarker concentrations in blood in the diagnosis of sepsis is shown below in Table 2, which presents the results of a study of the diagnosis of sepsis, severe sepsis, and septic shock according to serum PCT measurements.

TABLE 2

| | Serum PCT range (ng/ml) | | | | |
|---|---|---|---|---|---|
| Diagnosis | <0.5 | >0.5 & <2.0 | >2.0 & <10 | >10 | Total |
| Sepsis | 4 (7.7%) | 15 (28.8%) | 19 (36.5%) | 14 (26.9%) | 52 (100%) |
| Severe Sepsis | 1 (4.0%) | 5 (20.0%) | 9 (36.0%) | 10 (40.0%) | 25 (100%) |
| Septic Shock | 1 (4.3%) | 5 (17.4%) | 7 (30.4%) | 11 (47.8%) | 23 (100%) |

Procalcitonin (PCT) is a 116 amino acid peptide that has an approximate molecular weight MW of 14.5 kDa and belong to the calcitonin family of peptides. The PCT molecule consist of three sections, the amino terminus (57 amino acids), immature calcitonin (33 amino acids) and calcitonin carboxyl-terminus peptides 1 (CCP-1) known as katacalcin (21 amino acids). PCT is a precursor hormone of calcitonin, which is not detectable in healthy individuals since the peptide is not released into the blood in the absence of systematic inflammation. In case of a sepsis caused by bacterial infections, however, PCT synthesis is induced in tissues and therefore becomes detectable in blood. Production of PCT can be triggered by bacterial toxins such as endotoxins and cytokines (e.g., interleukin (IL)-1beta, interleukin-6 and tumor necrosis factor (TNF)-alpha). PCT levels can increase rapidly between 2 hr and 6 hr, and peaks within 6 hr to 24 hr of bacterial infection. In addition to bacterial infections, some fungal and parasitic infections have been associated with the release of PCT in the blood stream.

Additional conditions that trigger high levels of PCT in the body include recent major surgeries, severe trauma, severe burns, prolonged cardiogenic shock and chronic kidney diseases.

The lack of ability in some extra-thyroidal tissues to cleave PCT to its mature form, calcitonin, allows the accumulation of PCT in the blood. Consequently, PCT can be used as a biomarker with relatively high differentiation between bacterial and viral inflammations that can be used in patients suffering of sepsis. Moreover, PCT levels can be related to and/or indicative of the severity of a bacterial infection. In sepsis cases, a prompt diagnosis of bacterial infection reduces the risk of unnecessary or inappropriate use of antibiotics that could increase the resistance to antibiotics or the toxic side effects in patient.

Conventional approaches to diagnose sepsis caused by bloodstream infections include culturing blood, urine, cerebrospinal fluid, of bronchial fluid specimens. These test approaches can typically take between 24 hours to 48 hours to produce result, and often times can facilitate identification of pathogens, providing information about the type of microorganism and its susceptibility towards antibiotics. Clinical symptoms, however, can manifest in the absence of a positive culture, leading to medical treatment based on false negative results. The half-life of PCT (25 hrs to 30 hrs) coupled with its specificity for bacterial infection and its substantial absence in healthy individuals, make PCT a suitable biomarker of bacterial infection.

PCT can be quantified by immunoassays based on the sandwich ELISA principle. In those immunoassays, antibody-procalcitonin-antibody complexes are formed and quantified by one or more instrumentation techniques including chemiluminescence, enzymatic, fluorescent, and turbidimetric immunoassays. For example, the chemiluminescence assay for PCT uses a two-step sandwich approach. In this method, anti-PCT monoclonal antibodies conjugated with alkaline phosphatase are added to a patient sample in the presence of a reagent buffer. After incubation, paramagnetic particles coated with monoclonal anti-PCT antibody are added to the test. PCT binds with the paramagnetic particles while the anti-PCT antibodies in solution react with different antigenic sites of the PCT molecule. The particles are separated by magnets from the non-conjugated material. A chemiluminescent substrate is added to the test and the light generated by the reaction is measured using a luminometer, where photon generation is proportional to the concentration of PCT in the sample.

Alternatively, PCT can be measured using a quantitative homogeneous assay (BRAHMS, Hennigsdorf, Germany) based on Time Resolved Amplified Cryptate Emission technology (TRACE). The test involves directing a nitrogen laser 337 nm beam at a sample containing PCT and 2 fluorescently labeled antibodies recognizing different epitopes of the PCT peptide. Exposure to the laser excitation triggers transfer of non-radiative energy between donor and acceptor molecules; the donor molecule emitting a long-lived fluorescent signal at 620 nm, and the acceptor molecule emitting a short-lived signal at 665 nm. When both donor and acceptor molecules are brought into proximity by binding to PCT, the resultant signal is amplified at 665 nm and lasts for a few microseconds, long enough to be detected after decay of background fluorescence common in biological samples.

Lateral flow assays (LFA) configured to test for blood (e.g., whole blood, serum, etc.) PCT biomarkers (e.g., antigens) provide an alternative tool for the diagnosis of sepsis. As described above with reference to FIG. 2, an LFA can be performed over a strip comprising one or more components assembled over a substrate 171. The components of an LFA configured for detecting and quantifying PCT in blood and/or other biofluids can include a sample element 172, a conjugate element 173, a capture element 174, a control element 175, and a wick 176.

The substrate 171 can be a backing laminate or a backing card configured to provide mechanical support to components of the LFA, as described above. The substrate 171 can be any suitable shape, size, and/or configuration, as described above. For example, the substrate 171 can be a rectangular backing card or strip of constant width and a predetermined length capable of providing sufficient surface area for accommodating the various components of the LFA. The substrate 171 can be made of a semi-rigid polymer designed to deliver uniformity and lay-flat properties. The substrate 171 can include one or more pressure sensitive adhesives configured to facilitate attaching the various components of the LFA, as further described herein.

The sample element 172 can be a pad that provides a surface to receive a sample of blood and/or other biofluids for analysis and facilitates transport of the sample to other components of the lateral flow test strip in a smooth, continuous and homogeneous manner. The sample element 172 can be any suitable shape and/or size. In some embodiments the shape of the sample element 172 can be a rectangular strip configured to adsorb and receive a volume of a sample of blood and/or other biofluids. The sample element 172 can be disposed onto the surface of the substrate 171 to provide mechanical support to the LFA. In some embodiments, the sample element 172 can include an adhesive coated on one surface of the sample pad to facilitate attachment to a plastic backing laminate. The shape and dimensions of the sample element 172 can be predetermined such that the sample element can be disposed onto a plastic backing laminate. The thickness of the sample element 172 can be selected to facilitate adhesion of the sample element 172 to the plastic backing laminate while maintaining the mechanical structure of the pad. Additionally, the thickness of the sample element 172 can be selected to accommodate large volumes of blood and/or other biofluids, preventing oversaturation of the sample on the pad, and channeling to the plastic backing laminate. The sample element 172 can be made of cellulose, nitrocellulose, glass fiber, and/or any other suitable material.

The conjugate element 173 of an LFA for detection and quantification of PCT from blood and/or other biofluid samples can be a pad located adjacent downstream to the sample element 172, as shown in FIG. 2. The conjugate element 173 can be any suitable shape and/or size. In some embodiments, the shape of the sample element 172 can be a rectangular strip of similar width as that of the sample member 171, disposed onto the surface of the substrate 171 to provide mechanical support to the LFA. The conjugate element 173 can contain a dried matrix (e.g., a salt-sugar matrix) that includes bio-active particles and additives. The bio-active particles contained in the matrix include specific antibodies and/or affinity reagents (e.g., DNA aptamers, protein binders, etc.) that have been immobilized on or in the conjugate element 173. For example, in some embodiments the surface of the sample element 172 can be impregnated with an aqueous buffer solution that provide an environment with controlled pH. In some embodiments, the surface of the sample element 172 can be impregnated with a buffer solution including, but not limited to borate buffer solution, phosphate-buffered saline (PBS), 2-ethanesulfonic acid (MES), tris(hydroxymethyl)aminomethane (TRIS), piperazine-N, N'-bis (PIPES), 3-morpholinopropane-1-sulfonic acid (MOPS), 2-[4-(2-hydroxyethyl)piperazin-1-yl] ethanesulfonic acid (HEPES), [tris(hydroxymethyl)methylamino] propanesulfonic acid (TAPS), N-Cyclohexyl-2-aminoethanesulfonic acid (CHES), and/or N-cyclohexyl-3-aminopropanesulfonic acid (CAPS).

The dried matrix of the sample element 172 can include one or more surfactants used as a wetting agent for solubilizing polar species present in the sample. For example, in some embodiments, the dried matrix of the conjugate element 173 can include nonionic surfactants such as glycidol, tergitol, ethoxylated and alkoxylated fatty acids, ethoxylated amines, alkyl and nonyl-phenol ethoxylates, ethoxylated sorbitan esters, castor oil ethoxylate and the like. The dried matrix can include one or more biocide reagents configured to facilitate extending the shelf life of the LFA by inhibiting a broad spectrum of microbes. The biocide reagents can be formulated in the dried matrix of the conjugate element 173 at low concentrations in order to minimize and/or avoid potential health hazards, toxicology problems, and disposal issues. For example, in some embodiments, dried matrix can include 5-Chloro-2-methyl-4-isothiazolin-3-one (CMIT), 2-Methyl-4-isothiazolin-3-one (MIT), proprietary glycol, modified alkyl carboxylate, and/or other commercially available preservative formulations such as proclin 300™. In some embodiments, the dried matrix can include one or more detergents or any amphiphilic molecule that can be used for protein solubilization such as tween 20, Triton X, octylthio glucoside and others.

The dried matrix of the conjugate element 173 can include one or more antibodies and/or affinity reagents conjugated to a molecule configured to allow detection. In some embodiments, the dried matrix can include one or more detector antibodies that can bind to PCT and exhibit high stability. For example, in some embodiments the detector antibodies can include procalcitonin human antibodies including monoclonal anti-PCT antibody 14A2cc, monoclonal anti-CT antibody 796, PP3, and the like.

The detector antibodies can be immobilized to one or more colored particle (e.g., latex having a blue color, colloidal gold having a red color, and/or any other suitable particle), a fluorescent particle, a magnetic particle or any other suitable particle that can be used for the capture and quantification of PCT in a sample of blood and/or other biofluid. In some embodiments, the detector antibodies can be immobilized to a gold nanoparticle. Gold nanoparticles and/or gold nano-shells can be functionalized with antibodies that are exhibit specific binding activity towards certain regions of the PCT molecule (e.g., bioconjugation). During bioconjugation, the surface of gold nanoparticles can be functionalized with detector antibodies using physical methods that rely on physical interactions between the detector antibody and the surface of the gold nanoparticle, such as ionic interactions, hydrophobic interactions, and/or dative binding. Physical interactions occur by spontaneous absorption of antibodies onto the surface of the gold nanoparticles. In the case of ionic interactions, positively charged groups in the detector antibodies are attracted to the negatively charged surface of the gold nanoparticles. Hydrophobic interactions occur between hydrophobic parts of the detector antibodies and the metal surface.

Advantages of functionalization of gold nanoparticles with detector antibodies via physical methods include ease of fabrication, simplicity, low cost, rapid fabrication, and use of minimal additives and/or chemicals that can cause harmful toxicological effects. However, certain disadvantages of physical methods can include the use of large amounts of detector antibodies in the preparation of the functionalized gold nanoparticles, the random orientation of the detector antibodies and the relative ease of replacement of the detector antibody by other molecules with similar characteristics. These disadvantages can often result in high assay variability and low PCT capture capacity, due to the low specificity of the binding modality on the gold nanoparticle. For example, the conjugation of antibodies to the surface of the gold nanoparticle can proceed by nonspecific bindings sites that may occlude the regions of the antibody suitable for PCT capture. For example, in some instances, the antibodies can be physically adsorbed on the surface of the gold nanoparticle by interactions between the constant domains present in the heavy chain and the surface of the nanoparticle. In this configuration, the antigen binding sites of the antibody may be partially available for interacting with PCT. In other instances, the antibodies can be physically adsorbed on the surface of the gold nanoparticle by interactions between the PCT antigen binding cite, which precludes interactions of the antigen binding sites and PCT.

Alternatively, in some embodiments, the antibodies can be conjugated to the gold nanoparticles by chemical methods involving covalent bonds, such as chemisorption via thiol derivatives, bifunctional linkers, and/or adapter molecules. Direct functionalization of gold nanoparticles with thiol derivative groups can be achieved by the chemical reaction between gold and sulfur atoms creating a strong bond on the surface of the particle. For example, Thiol-functionalized antibodies can be directly attached to the gold nanoparticles. However, this approach presents challenges such as the use of reaction conditions that may harm the stability of the nanoparticles and may require harsh conditions.

The embodiments, implementations, and/or methods described herein can overcome these limitations, for example, by including the use of other groups that can be attached to the gold nanoparticles surface using bifunctional linkers providing specific functionalization in the surface of the gold nanoparticle. For example, carboxilated polyethylene glycol (PEG) molecules functionalized with thiol groups (PEG-SH) can be used to functionalize the surface of the gold nanoparticles. The PEG molecules functionalized to the gold nanoparticles can also include carboxyl terminated groups. These carboxyl terminated groups can be modified with a coupling chemistry including water-soluble carbodiimide (EDC) and N-hydroxy-succinimide (NHS) compounds to create a reactive functional group that binds to the primary amine groups in an antibody molecule. The water-soluble carbodiimide reacts with carboxylic moieties in the PEG containing gold nanoparticles to create an intermediate active group that will react with N-hydroxy-succinimide compound to form a reactive ester groups. When in direct contact with the antibodies, the primary amine groups in the antibody react with the ester group formed in the surface of the gold nanoparticle. This reaction is designed to create amide bonds to attach antibodies to the gold nanoparticles without adding a spacer molecule between them.

The capture element 174 of an LFA for detection and quantification of PCT from blood and/or other biofluid samples can be a pad disposed adjacent to and/or downstream of the conjugate element 173, containing particles or molecules that have been immobilized in or on the capture element 174. As described above with reference to FIG. 2, the particles or molecules can be configured to bind to the detector antibodies conjugated to the colored particles described above with reference to the conjugate element 173, as the flow downstream in a volume of the blood and/or other biofluid sample. In some embodiments, the capture element 174 can include capture antibodies immobilized and/or chemically bound to the surface of the capture element 174. The capture antibodies can be configured to interact with the detector antibodies to capture PCT bound to the detector antibody, producing a localized accumulation of the detector antibody and their conjugated colored particle. In some embodiments, the capture antibodies can be adsorbed on the surface of the capture element 174.

As described above with reference to the detection antibodies, the capture antibodies can include procalcitonin human antibodies including monoclonal anti-PCT antibody 14A2cc, monoclonal anti-CT antibody 796, PP3, and the like. The immobilized capture antibodies can be configured to bind PCT molecules which have been previously bound to the detector antibodies (and their conjugated colored particles) in the conjugate element 173. As a result, exposure of the capture element 174 to a sample of blood and/or other biofluid containing PCT previously flown through the conjugate element 173 can cause accumulation of the colored particles associated to capture antibodies that bound PCT molecules present in the sample. This accumulation of colored particles on the capture element 174 can be registered and quantified by one or more optical methods, to determine the concentration of PCT in the sample. For example, in some embodiments, the colored particles accumulated on capture element 174 can be determined by a standard lateral flow reader such as a commercially available Leelu reader (LUMOS diagnostics), configured to detect colored particles providing suitable optical sensitivity and dynamic range sufficient to cover a broad range of concentrations.

The LFA can include the control element 175 to capture detection antibodies not otherwise captured by the capture elements 174. In other embodiments, the LFA need not include a control element. The wick 176 of an LFA configured for detection and quantification of PCT from blood and/or other biofluid samples can be a pad that disposed adjacent to and/or downstream of the capture element 174 (or the control element 175 if included). As described with reference to FIG. 2, the wick 176 can be configured to absorb or wick portions of the sample that have not been immobilized in or on the capture element 174 (and/or the control element 175 if included).

The Lateral flow assays (LFA) configured to test for PCT in blood and/or other biofluids as described above can detect PCT present in various samples including buffer solutions, serum, plasma and/or whole blood. More specifically, in some embodiments, the LFA can exhibit a dynamic range of detectable PCT of 0.2 ng/mL-2 ng/mL, and a sensitivity equal to or higher than 0.1 ng/mL in buffer and serum. In some embodiments, the LFA can exhibit a cutoff PCT concentration of 0.2 ng/mL and 0.5 ng/mL in buffer/serum. The total time required to obtain results using the LFA configured for PCT detection can be about 10 min. The LFA configured for PCT detection can remain relatively stable during accelerated stability tests conducted at 37 C, without significant conjugate release and flow through the lateral flow strip.

While tests of serum lactate and/or serum PCT concentrations are described above, it should be understood that testing blood (e.g., whole blood or other suitable portions of blood) would produce similar or substantially the same results. While lactate biomarkers and PCT biomarkers are described above, it should be understood that they have been presented by way of example only and not limitation. In some implementations, the rapid testing device (e.g., the LFA 170A) can be configured to test for any suitable biomarker associated with and/or otherwise indicative of sepsis and/or any other infectious or disease condition. Moreover, it should be understood that the rapid testing device 170 and/or the LFA 170A (and/or any other suitable flow-based assay) can be used in conjunction with any of the fluid transfer devices described herein with reference to specific embodiments.

Aptamers

In some implementations, the rapid testing device 170 can be an LFA (e.g., the LFA 170A) configured to use aptamers to test for any suitable biomarker associated with sepsis and/or any other infectious condition. Aptamers are single-stranded DNA or RNA molecules that can selectively bind to corresponding targets with high affinity and specificity. These single stranded molecules consist of a variable region comprising 20-40 bases in the middle end flanked with two constant regions at each end comprising binding sites. Aptamers can fold into secondary structures and three-dimensional shapes owing to intermolecular hybridization. The equilibrium dissociation constant of aptamer-target binding in the 1 pico Molar (pM) to 1 nano Molar (nM) range. Aptamers have similar affinities as antibodies to target molecules and can be generated against desired target such as toxic small molecules, non-immunogenic targets or single molecules which are not binding to antibodies. Additionally, aptamers can be reversibly denaturized by heat or chemicals which is not possible for antibodies.

Aptamers are analogous to antibodies in the range of target recognition and variety of applications. The use of aptamers, however, may present advantages over the use of antibodies including, for example, fabrication via in vitro processes that rely on easily controlled and highly reproducible chemical reactions, in contrast to the complex experiments required to derive antibodies from bacteria, cell culture, and/or animal cells (including human cells), ability to bind targets that are not recognized by antibodies such as ions, small molecules, complex multi-active site molecules, proteins, bacteria cells, viruses, and/or cancer cells, capability to be massively amplified in a short time by the polymerase chain reaction (PCR), ease of modification to introduce functional moieties (e.g., fluorophores, quenchers, and nanomaterials), stability under harsh conditions, and safety use on in vivo applications owing to their non-immunogenic characteristics. In some instances, aptamers can improve transport properties allowing cell specific targeting and improved tissue penetration.

Aptamers can be tailored to specific targets obtained through systematic evolution of ligands by exponential enrichment (SELEX) process. This process includes three major steps: library generation, selection, and amplification. In the first step, a random library is designed and synthesized by a combinatorial chemical synthesis technique to produce oligonucleotides comprising the variable region with 20-40 bases flanked by the upstream and downstream primer binding sites at each end. The resulting library can contain $10^{12}$-$10^{15}$ ssDNA or RNA sequences. In the second step, the target molecule is incubated with the library for several minutes in the presence of a binding buffer. Aptamers will bind to the target and form aptamer-target complexes, and non-specific sequences will remain in the binding buffer. The aptamer-target complexes can be collected and washed several times with washing buffer. The aptamers can then be separated from the aptamer-target complexes by treatment with an elution buffer. The selection step can include counter-selection procedure in which the target is replaced for analogs, and the nucleic acid sequences that bind to the analogs are excluded. In the third step, the sequences eluded in the second step are amplified by PCR, in the case of DNA, and by reverse transcriptase (RT)-PCR for RNA, to produce a sub-library to use on a second round of SELEX process. The procedure can be repeated several rounds until producing aptamers with high specificity for the target.

When affinities of the sequences bound to the target are saturated, they are sent to the clone and sequence, following the identification of aptamer sequences that bind the target with high sensitivity and specificity. Several techniques can be used in order to improve the separation of unbound sequences from aptamer-target complexes. For example, in some instances the selection of aptamers can include nitrocellulose membrane filtration-based SELEX, affinity chromatography and magnetic bead-based SELEX, capillary electrophoresis and/or microfluidic-based SELEX. Nitrocellulose membrane filtration-based SELEX uses nitrocellulose membranes to retain the complexes of aptamer-target and remove unbound oligonucleotide sequences based on size Multiple pores of micron size on the surface of the membrane allow DNA or RNA oligonucleotides to pass through and the protein to be trapped on the membrane. The material is then amplified by the PCR or RT-PCR for the next round of the fabrication. Affinity chromatography and magnetic bead-based SELEX uses Agarose beads packed onto a column as stationary phase. Magnetic beads are also used for the immobilization of the target through a physical interaction or chemical reaction between a specific tag and its ligand on the beads. Capillary electrophoresis and microfluidic based SELEX are used to improve separation speed, resolution, and capacity with minimal sample dilution. In this method, unbound nucleotides are separated from aptamer-target complexes due to their differences in electrophoretic mobility in an electric field. The aptamer can be obtained by the migration speeds of the mixture of target, ligand or target-ligand complexes. Capillary electrophoresis-based SELEX can be used to select the aptamer in a few rounds compare to other methods. Microfluidic-based SELEX is a technique is a n automated and miniaturized platform that enables aptamer selection on a chip. To carry out the selection process automatically, the system includes several modules with micropumps, microvalves, reservoir manifolds, waste chambers, and PCR chambers. Other methods including atomic force microscopy, high-throughput sequencing, graphene oxide, crosslinking by UV, flow cytometry and surface plasmon resonance (SPR) can be used in connection with the SELEX process. These methods are used to enrich the selection measures and to improve efficiency of aptamer selection.

Aptamers applications include in vivo therapeutics, molecular bio sensor, target capture, drug delivery, new drug development, hazard detection, environmental monitoring, clinical diagnosis, biomarkers discovery and food inspection. Aptamers are used as recognition elements for analytical tools including electrochemical and fluorescent biosensors, colorimetric assays, surface plasmon resonance assays and amplification techniques.

Detection

In some instances, the rapid testing device 170 (e.g., the LFA 170A and/or any other suitable rapid testing device) can be configured to present test results that can be detected and/or assessed by a human (e.g., a doctor, nurse, technician, etc.) via visual inspection. For example, a doctor, nurse, technician, etc. can visually inspect the capture element 174 of the LFA 170A to determine if a strip is present along the capture element 174. In addition, the control element 175 of the LFA 170A can be visually inspected to verify the performance of the test. In some such instances, visual inspection by a human can be relatively simple to implement and may not use additional equipment to provide qualitative results (e.g., a positive or a negative test result).

In other instances, the LFA 170A can be configured to output test results, which in turn, can be received, inspected, analyzed, interpreted, etc. by one or more electronic devices (e.g., the electronic device 190 shown in FIG. 1). For example, in some instances, a portable strip reader can be used to read, scan, and/or assess the strip(s) along the capture element 174 and/or the control element 175. The strip reader can include a camera, scanner, reader, and/or the like that can use a complementary metal-oxide semiconductor (CMOS) device, a charge-coupled device (CCD), and/or any other suitable detection device or camera to detect the strip(s). In some implementations, the strip reader can be configured to define data or a digital representation of test results (strips), which can be qualitative, semi-quantitative, and/or quantitative. For example, a capture element intensity can be proportional to concentration of the analyte, thereby allowing for quantification of the analyte. In some instances, the strip reader can be configured to read, scan, and/or identify the presence of one or more strips as well as the intensity of the one or more strips, thereby providing both qualitative and quantitative data. In some implementations, the electronic device 190 can be integrated into/onto the rapid testing device 170 or it can be a stand-alone device into which the rapid testing device 170 and/or one or more cartridges (e.g., one or more portions of the rapid testing device 170) can be inserted for reading and analysis.

In some embodiments, the strip reader can be configured to provide the qualitative and/or quantitative data as an input into the electronic device 190, which can analyze, process, and/or otherwise use the data to produce one or more qualitative and/or quantitative test results. The electronic device 190 can be any suitable hardware-based computing device configured to receive, process, define, and/or store data such as, for example, one or more diagnostic test results, test standards against which to measure results data, predetermined and/or predefined treatment plans, patient profiles, disease profiles, etc. In addition, the electronic device 190 can be configured to send and/or receive data via a wired or wireless connection or network. In some embodiments, the electronic device 190 can be, for example, a mobile electronic device (e.g., a smartphone, a tablet, a laptop, and/or any other mobile or wearable device), a personal computer (PC), a workstation, a server device or a distributed network of server devices, a virtual server or machine, a virtual private server and/or the like that is executed and/or run as an instance or guest on a physical server or group of servers, and/or any other suitable device. In some implementations, the electronic device 190 can be configured to provide a graphic and/or digital representation of the test results produced by the rapid testing device 170. In addition, in some implementations, based on data associated with and/or representing the test results, the electronic device 190 can be configured to determine and graphically or digitally present one or more diagnoses, one or more treatment plans, one or more simulations, and/or any other suitable data associated with the bodily fluid sample, the patient, and/or the medical treatment of the patient.

As described above, in some implementations, the transfer device 105 can be configured transfer the first amount of bodily fluid to the rapid testing device 170 and at least some of the second amount of bodily fluid to one or more of the optional fluid collection devices 195. For example, the second or sampling portion of the transfer device 105 can include and/or can be in fluid communication with an outlet or port, which can allow the second amount of bodily fluid to be transferred out of the second or sampling portion of the transfer device 105. In some instances, the one or more optional fluid collection devices 195 can be physically and/or fluidically coupled to the transfer device 105 (e.g., via the outlet or port) to receive at least some of the second amount of bodily fluid.

In some embodiments, the optional fluid collection device(s) 195 can be any suitable device(s) for at least temporarily containing a bodily fluid. For example, a fluid collection device 195 can include, but is not limited to, any suitable vessel, container, reservoir, bottle, adapter, dish, vial, syringe, device, diagnostic and/or testing machine, and/or the like. In some embodiments, a fluid collection device can be substantially similar to or the same as known sample containers such as, for example, a Vacutainer® (manufactured by Becton Dickinson and Company (BD)), a BacT/ALERT® SN or BacT/ALERT® FA (manufactured by Biomerieux, Inc.), and/or any suitable reservoir, vial, microvial, microliter vial, nanoliter vial, container, microcontainer, nanocontainer, and/or the like. In some embodiments, a fluid collection device can be substantially similar to or the same as any of the sample reservoirs described in U.S. Pat. No. 8,197,420 entitled, "Systems and Methods for Parenterally Procuring Bodily-Fluid Samples with Reduced Contamination," filed Dec. 13, 2007 ("the '420 Patent"), the disclosure of which is incorporated herein by reference in its entirety.

In some embodiments, the fluid collection device 195 can be devoid of contents prior to receiving a sample volume of bodily fluid. For example, in some embodiments, the fluid collection device 195 or reservoir can define and/or can be configured to define or produce a vacuum, suction, and/or negative pressure condition such as, for example, a vacuum-based collection tube (e.g., a Vacutainer C), a syringe, and/or the like. In some implementations, the fluid collection device 195 can be physically and/or fluidically coupled to the transfer device 105 (e.g., the outlet or port) such that the negative pressure conditions within the fluid collection device 195 facilitate withdrawal of bodily fluid from the patient, and into or through one or more portions of the transfer device 105, as described in further detail herein with reference to specific embodiments.

In some embodiments, the fluid collection device 195 can include any suitable additives, culture media, substances, enzymes, oils, fluids, and/or the like. For example, the fluid collection device 195 can be a sample or culture bottle including, for example, an aerobic or anaerobic culture medium. The sample or culture bottle can be configured to receive a bodily fluid sample, which can then be tested (e.g., after incubation via in vitro diagnostic (IVD) tests, and/or any other suitable test) for the presence of, for example, Gram-Positive bacteria, Gram-Negative bacteria, yeast, fungi, and/or any other organism. In some instances, if such a test of the culture medium yields a positive result, the culture medium can be subsequently tested using nucleic acid-based systems (e.g., a PCR-based system(s), hybridization probe(s), nucleic acid amplification test(s) (NAATs), etc.) to identify a specific organism. In some embodiments, a sample reservoir can include, for example, any suitable additive or the like in addition to or instead of a culture medium. Such additives can include, for example, heparin, citrate, ethylenediaminetetraacetic acid (EDTA), oxalate, sodium polyanethol sulfonate (SPS), and/or the like. In some embodiments, the fluid collection device 195 can include any suitable additive or culture media and can be evacuated and/or otherwise devoid of air.

While "culture medium" is described above as a substance configured to react with organisms in a bodily fluid (e.g., microorganisms such as bacteria) and "additive" is described above as a substance configured to react with portions of the bodily fluid (e.g., constituent cells of blood, blood, synovial fluid, etc.), it should be understood that a sample reservoir can include any suitable substance, liquid, solid, powder, lyophilized compound, gas, etc. Moreover, when referring to an "additive" within a sample reservoir, it should be understood that the additive could be a culture medium, such as an aerobic culture medium and/or an anaerobic culture medium contained in a culture bottle, an additive and/or any other suitable substance or combination of substances contained in a culture bottle and/or any other suitable reservoir such as those described above. That is to say, the embodiments described herein can be used with any suitable fluid reservoir or the like containing any suitable substance or combination of substances.

In some implementations, the second amount of bodily fluid contained in the second or sampling portion of the transfer device 105 and/or contained in the optional one or more fluid collection devices 195 can be used as a biological sample in one or more tests, assays, and/or diagnostic procedures. In some instances, sequestering the first amount of bodily fluid from the second amount of bodily fluid can sequester contaminants or the like in the first amount of bodily fluid and/or in the sequestration portion of the transfer device 105. The sequestering, in turn, can leave the second amount of bodily fluid substantially free of contaminants. Accordingly, the second portion or amount of bodily fluid can be used in one or more tests such as blood culture tests and/or the like, which may be relatively sensitive to contaminants (e.g., can produce adulterated results due to the presence of contaminants). In this manner, the system 100 can be configured to procure the first amount of bodily fluid, which can be used in testing that has relatively low sensitivity to contamination, and the second amount of bodily fluid, which can be used in testing that has a relatively high sensitivity to contamination. In some instances, the testing of the first amount of bodily fluid can provide relatively quick initial results that can inform one or more treatment options, while the testing of the second amount of bodily fluid can provide more detailed test results that typically take longer to develop. Thus, for time sensitive disease conditions (e.g., sepsis), the initial results from testing the first amount of bodily fluid can allow a doctor or physician to provide rapid initial treatment while the more detailed testing of the second amount of bodily fluid is being performed.

Figure 3:
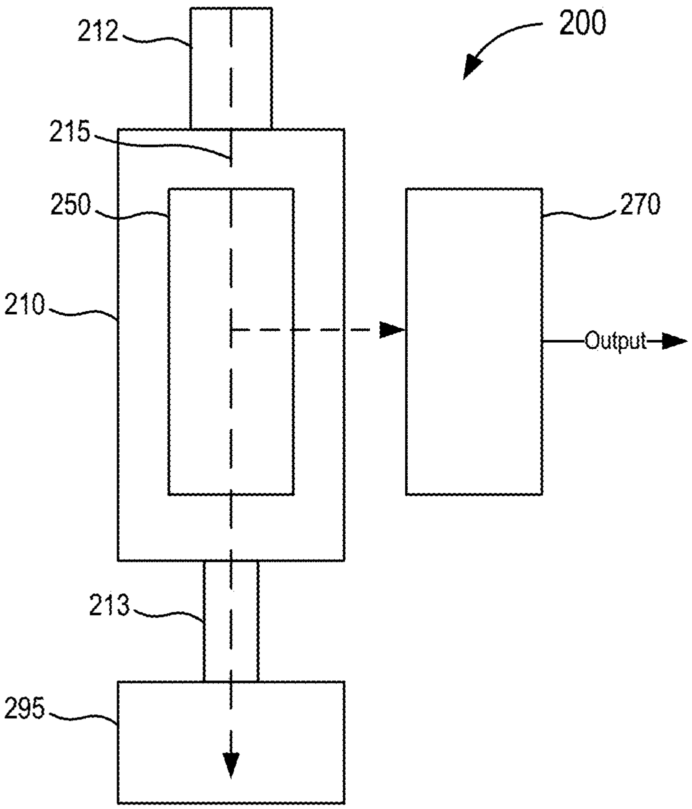
FIG. 3 is a schematic illustration of a fluid transfer and assay system according to an embodiment.

FIG. 3 is a schematic illustration of a fluid transfer and assay system 200, according to an embodiment. The fluid transfer and assay system 200 (also referred to herein as "system") can include at least a fluid transfer device 205 and a rapid diagnostic testing device 270. In addition, the system 200 can include at least one fluid collection device 295 that can be physically and/or fluidically coupled to the fluid transfer device 205.

The fluid transfer device 205 (also referred to herein as "transfer device") can be any suitable shape, size, and/or configuration. In some implementations, the transfer device 205 can be configured to withdraw bodily fluid (e.g., blood) from a patient and into and/or through the transfer device 205. In addition, the transfer device 205 can be configured to transfer at least some of the withdrawn bodily fluid to one or more other devices, reservoirs, containers, vials, machines, tests, assays, etc., such as the rapid diagnostic testing device 270 and/or one or more fluid collection devices 295.

The transfer device 205 includes a housing 210 and an actuator 250. The housing 210 of the device 205 can be any suitable shape, size, and/or configuration. For example, in some embodiments, the housing 210 can have a size that is at least partially based on an initial amount or volume of bodily fluid configured to be transferred into and/or sequestered within a portion of the housing 210. In some embodiments, the housing 210 can have a size and/or shape configured to increase the ergonomics and/or ease of use associated with the device 205. Moreover, in some embodiments, one or more portions of the housing 210 can be formed of a relatively transparent material configured to allow a user to visually inspect and/or verify a flow of bodily fluid through at least a portion of the housing 210.

The housing 210 has and/or forms an inlet 212 and an outlet 213 and defines at least one fluid flow path 215 therebetween. The inlet 212 can be any suitable inlet, opening, port, stopcock, lock (e.g., a luer lock), seal, coupler, valve (e.g. one-way, check valve, duckbill valve, umbrella valve, and/or the like), tubing, conduit, etc. The inlet 212 is configured to fluidically couple the housing 210 to a bodily fluid source (e.g., a patient). For example, the inlet 212 can be coupled to a lumen-containing device that is configured to be percutaneously disposed in a patient (e.g., a butterfly needle, intravenous (IV) catheter, peripherally inserted central catheter (PICC), midline, intermediary lumen-containing device, and/or the like). Thus, fluid can be transferred between the housing 210 and the patient via the inlet 212 and any lumen-containing device(s) coupled therebetween. More particularly, the transfer device 205 can be configured to transfer bodily fluid from the patient and/or any other bodily fluid source, through the inlet 212 (and/or any lumen-containing device coupled thereto), and into the housing 210 via the inlet 212, as described in further detail herein.

As shown in FIG. 3, the housing 210 defines one or more fluid flow paths 215 between the inlet 212 and the outlet 213. As described in further detail herein, the transfer device 205 and/or the housing 210 can be configured to transition between any number of states, operating modes, and/or configurations to selectively control bodily fluid flow through the one or more fluid flow paths 215. Moreover, the transfer device 205 and/or the housing 210 can be configured to transition automatically (e.g., based on pressure differential, time, electronically, saturation of a membrane, an absorbent and/or barrier material, etc.) or via intervention (e.g., user intervention, mechanical intervention, or the like).

The outlet 213 is in fluid communication with the one or more fluid flow paths 215 and is configured to selectively receive a flow of bodily fluid from the inlet 212 (via the fluid flow paths 215). The outlet 213 can be any suitable outlet, opening, port, stopcock, lock, seal, coupler, valve, tubing, conduit, etc. configured to physically and/or fluidically coupled to any suitable device coupled to the outlet 213 such as, for example, the fluid collection device 295 (e.g., a fluid or sample reservoir, syringe, evacuated container, culture bottle, etc.). In some embodiments, the outlet 213 can be monolithically formed with the fluid collection device 295. In other embodiments, the outlet 213 can be at least temporarily coupled to the fluid collection device 295 via an adhesive, a resistance fit, a mechanical fastener, a threaded coupling, a piercing or puncturing arrangement, any number of mating recesses, and/or any other suitable coupling or combination thereof. For example, in some embodiments, the outlet 213 can include and/or can be coupled to a fluid transfer adapter such as those described in U.S. Pat. No. 10,123,783 entitled, "Apparatus and Methods for Disinfection of a Specimen Container," filed Mar. 2, 2015 ("the '783 patent"), and/or can be coupled to a fluid transfer device such as those described in U.S. Patent Publication No. 2015/0342510 entitled, "Sterile Bodily-Fluid Collection Device and Methods," filed Jun. 2, 2015 ("the '510 publication"), the disclosure of each of which is incorporated herein by reference in its entirety. In such embodiments, the fluid transfer adapter can be coupled to and/or can receive a portion of the fluid collection device 295 and can establish fluid communication between the outlet 213 and the fluid collection device 295. In still other embodiments, the outlet 213 can be operably coupled to the fluid collection device 295 via an intervening structure (not shown in FIG. 3), such as sterile tubing and/or the like.

In some embodiments, the arrangement of the outlet 213 can be such that the outlet 213 is physically and/or fluidically sealed prior to coupling to the fluid collection device 295. In some embodiments, the outlet 213 can be transitioned from a sealed configuration to an unsealed configuration in response to being coupled to the fluid collection device 295 and/or in response to a negative pressure differential between an environment within the outlet 213 and/or housing 210 and an environment within the fluid collection device 295.

The fluid collection device 295 can be any suitable device for at least temporarily containing a bodily fluid, such as, for example, any of those described in detail above with reference to the fluid collection device 195 (e.g., an evacuated container, a sample reservoir, a syringe, a culture bottle, etc.). In some embodiments, the fluid collection device 295 can be a sample reservoir that includes a vacuum seal that maintains negative pressure conditions (vacuum conditions) inside the sample reservoir, which in turn, can facilitate withdrawal of bodily fluid from the patient, through the transfer device 205, and into the sample reservoir, via a vacuum or suction force. In embodiments in which the fluid collection device 295 is an evacuated container or the like, the user can couple the fluid collection device 295 to the outlet 213 to initiate a flow of bodily fluid from the patient and into the device 205 such that a first or initial portion of the flow of bodily fluid is transferred into and/or sequestered, for example, by the rapid diagnostic testing device 270, and a second or subsequent portion of the flow of bodily fluid bypasses and/or is otherwise diverted away from the rapid diagnostic testing device 270 and into the fluid collection device 295 (e.g., via the outlet 213), as described in further detail herein.

The actuator 250 of the device 205 is at least partially disposed within the housing 210 and is configured to control, direct, and/or otherwise facilitate a selective flow of fluid through at least a portion of the housing 210 and/or at least a portion of the one or more fluid flow paths 215. The actuator 250 can be any suitable shape, size, and/or configuration. In some embodiments, the actuator 250 can be a member or device configured to transition between two or more states (e.g., at least a first state and a second state). For example, the actuator 250 can be a valve, plunger, seal, membrane, bladder, flap, plate, rod, switch, and/or the like. The actuator 250 can be actuated and/or transitioned between any number of states (e.g., at least a first state and a second state) in any suitable manner. For example, transitioning the actuator 250 can include activating, pressing, moving, translating, rotating, switching, sliding, opening, closing, and/or otherwise reconfiguring the actuator 250.

In some implementations, the actuator 250 can be configured to transition between at least the first and the second state in response to a manual actuation by the user (e.g., manually exerting a force on a button, slider, plunger, switch, valve, rotational member, conduit, etc.). In other implementations, the actuator 250 can be configured to automatically transition between at least the first state and the second state in response to a pressure differential (or lack thereof), a change in potential or kinetic energy, a change in composition or configuration (e.g., a portion of an actuator could at least partially dissolve or transform), and/or the like. In still other implementations, the actuator 250 can be mechanically and/or electrically actuated or transitioned (e.g., via a motor, a spring-release mechanism, and/or the like) based on a predetermined time, volume of bodily fluid received, volumetric flow rate of a flow of bodily fluid, flow velocity of a flow of bodily fluid, etc. While examples of actuators and/or ways in which an actuator can transition are provided, it should be understood that they have been presented by way of example only and not limitation.

In the embodiment shown in FIG. 3, the actuator 250 can be configured to selectively establish fluid communication between the inlet 212 and the rapid diagnostic testing device 270 when in a first state and to selectively establish fluid communication between the inlet 212 and the outlet 213 when in a second state. When in the first state, the actuator 250 can be configured to allow bodily fluid to from the inlet 212, through at least a portion of the fluid flow path 215 and to or into the rapid diagnostic testing device 270. In some embodiments, the actuator 250 can be configured to sequester, separate, isolate, and/or otherwise prevent fluid communication between the outlet 213 and inlet 212, at least a portion of the fluid flow path 215, and/or the rapid diagnostic testing device 270. When in the second state, the actuator 250 can be configured to allow a subsequent volume of bodily fluid (e.g., a volume of bodily fluid after the initial volume of bodily fluid) to be transferred from the inlet 212, through at least a portion of the fluid flow path 215, and to the outlet 213 (and/or the fluid collection device 295 fluidically coupled to the outlet 213), as described in further detail herein. In addition, when in the second state, the actuator 250 can be configured to sequester, separate, isolate, and/or otherwise prevent fluid communication between the rapid diagnostic testing device 270 and the inlet 212, the outlet 213, and/or at least a portion of the fluid flow path 215, as described in further detail herein.

The rapid diagnostic testing device 270 (also referred to herein as "rapid testing device" or simply "testing device") can be any suitable shape, size, and/or configuration. In some embodiments, the rapid testing device 270 can be removably coupled to the transfer device 205 or any suitable portion thereof (e.g., an inlet portion, an outlet portion, a sequestration portion, a sampling portion, and/or any other suitable portion). In other embodiments, the rapid testing device 270 can be integrated into the transfer device 205. For example, the transfer device 205 and the rapid testing device 270 can be unitarily or monolithically formed and/or otherwise integrated. In still other embodiments, the transfer device 205 can include and/or can form a port, adapter, and/or receiving portion to which the rapid testing device 270 can be coupled or into which the rapid testing device 270 can be inserted to establish fluid communication therebetween. In some such embodiments, coupling the rapid testing device 270 to the transfer device 205 can be operable to transition one or more flow controllers, valves, septa, ports, seals, etc. from a closed or sealed state to an open state to allow fluid communication between the transfer device 205 and the testing device 270.

In some implementations, the rapid testing device 270 can be configured to receive the first amount of bodily fluid from the transfer device 205 and to use the first amount of bodily fluid to perform one or more tests, assays, and/or diagnostic procedures. The rapid testing device 270 can be any suitable testing device. For example, the rapid testing device 270 can be an LFA or the like, as described in detail above with reference to the LFA 170A shown in FIG. 2. In some implementations, the testing device 270 can be an LFA configured to test for the presence of specific analytes or biomarkers that can provide information used to diagnose a patient condition such as, for example, sepsis and/or any other disease state. For example, the LFA can be configured to test for lactate and/or PCT biomarkers, which can be indicators of sepsis. In other embodiments, the testing device can be an LFA configured to test for any of the target analytes and/or biomarkers described above with reference to the LFA 170A shown in FIG. 2.

In some instances, the rapid testing device 270 can be configured to output test results associated with testing the volume of bodily fluid transferred from the transfer device 205 while the transfer device 205 and/or the actuator 250 is in the first state. The test results (indicated in FIG. 3 by the arrow labelled "Output") can be detected and/or assessed by a human via visual inspection, and/or can be detected and/or assessed by one or more electronic devices (e.g., the electronic device 290). In some instances, the test results output by the rapid testing device 270 can be qualitative, semi-quantitative, and/or quantitative. Accordingly, the rapid testing device 270 can be structurally and/or functionally similar to or the same as the rapid testing device 170 described in detail above and therefore, is not described in further detail herein.

As described above, the system 200 can be used to procure one or more volumes of bodily fluid from a patient, which can be used in one or more tests, assays, and/or diagnostic procedures. For example, in some instances, a user such as a doctor, physician, nurse, phlebotomist, technician, etc. can manipulate the device 205 to establish fluid communication between the inlet 212 and the bodily fluid source (e.g., a vein of a patient, cerebral spinal fluid (CSF) from the spinal cavity, urine collection, and/or the like). As a specific example, in some instances, the inlet 212 can be coupled to and/or can include a needle or the like that can be manipulated to puncture the skin of the patient and to insert at least a portion of the needle in the vein of the patient, thereby placing the inlet 212 in fluid communication with the bodily fluid source (e.g., the vein, an IV catheter, a PICC, etc.).

In some instances, the actuator 250 can be in a first state when the inlet 212 is placed in fluid communication with the bodily fluid source (e.g., the portion of the patient), such that at least a portion of the fluid flow path 215 establishes fluid communication between the inlet 212 and the rapid testing device 270 (and/or a portion of the device 205 to which the rapid testing device 270 is coupled). As such, the transfer device 205 can be configured to transfer an initial volume of bodily fluid from the bodily fluid source (e.g., the patient) to the rapid testing device 270. In some implementations, the initial volume of bodily fluid can flow to the rapid testing device 270 passively (e.g., without user intervention and/or transitioning of one or more components) in response to a positive pressure associated with the vasculature of the patient and/or in response to any of the fluid transfer methods described in U.S. Patent Publication No. 2018/

0353117 entitled, "Fluid Control Devices and Methods of Using the Same," filed Jun. 11, 2018 ("the '117 publication"), the disclosure of which is incorporated herein by reference in its entirety.

In other implementations, the transfer device 205 and/or a portion thereof can be configured to produce a negative pressure differential (e.g., a partial vacuum, a suction force, and/or the like) within at least a portion of the fluid flow path 215 that can initiate and/or sustain a flow of the initial volume of bodily fluid from the bodily fluid source and to the rapid testing device 270. For example, in some instances, the actuator 250 can be stored in a third state (e.g., a storage state) prior to use and can be transitioned from the storage state to the first state to initiate the flow of the initial volume of bodily fluid. In such instances, the transitioning of the actuator 250 can generate a negative pressure that can draw the bodily fluid from the inlet 212 and to the rapid testing device 270. In some such implementations, the actuator 250 can be transitioned to generate a negative pressure differential in a manner similar to and/or substantially the same as any of those described in U.S. Pat. No. 8,535,241 entitled, "Fluid Diversion Mechanism for Bodily-Fluid Sampling," filed Oct. 22, 2012 ("the '241 patent"); U.S. Pat. No. 9,060,724 entitled, "Fluid Diversion Mechanism for Bodily-Fluid Sampling," filed May 29, 2013 ("the '724 patent"); U.S. Pat. No. 9,155,495 entitled, "Syringe-Based Fluid Diversion Mechanism for Bodily-Fluid Sampling," filed Dec. 2, 2013 ("the '495 patent"); U.S. Patent Publication No. 2016/0361006 entitled, "Devices and Methods for Syringe Based Fluid Transfer for Bodily-Fluid Sampling," filed Jun. 23, 2016 ("the '006 publication"); and/or U.S. Provisional Patent Application Ser. No. 62/802,999 entitled, "Devices and Methods for Bodily Fluid Collection and Distribution," filed Feb. 8, 2019 ("the '999 Application"), the disclosure of each of which is incorporated herein by reference in its entirety. In still other implementations, the initial volume of bodily fluid can flow to the rapid testing device 270 in response to a negative pressure differential generated by the fluid collection device 295, as described in further detail herein with reference to other embodiments.

The initial volume of bodily fluid can be any suitable volume of bodily fluid, such as any of the volumes or amounts described above. For example, in some instances, the transfer device 205 can remain in the first state or configuration until a predetermined and/or desired volume (e.g., the initial volume) of bodily fluid is transferred to the rapid testing device 270. In some embodiments, the initial volume can be associated with and/or at least partially based on a desired volume sufficient for the rapid testing device 270 to perform one or more tests or assays. In other embodiments, the initial volume of bodily fluid can be associated with and/or at least partially based on an amount or volume of bodily fluid that is equal to or greater than a volume associated with the fluid flow path defined between the bodily fluid source and the rapid testing device 270. In still other embodiments, the transfer device 205 can be configured to transfer a flow of bodily fluid (e.g., the initial volume) into the rapid testing device 270 until a pressure differential between the rapid testing device 270 and the inlet 212 or the bodily fluid source is brought into substantial equilibrium and/or is otherwise reduced below a desired threshold.

In some implementations, the rapid testing device 270 can initiate a test and/or assay of or on the initial volume of bodily fluid when the initial volume is transferred into, for example, a sample element or the like (e.g., the sample element 171). In some instances, the rapid testing device 270 can be configured to provide one or more solutions, buffers, mixtures, additives, and/or the like that can be mixed or combined with the initial volume. In this manner, the initial volume of bodily fluid (whether alone or mixed with additional components) can flow through the rapid testing device 270 (e.g., an LFA as described above with reference to FIG. 2), which in turn, can perform one or more tests or assays on the initial volume. For example, in some instances, the rapid testing device 270 can be an LFA configured to test for the presence of lactate and/or PCT, as described in detail above. Moreover, once the test or assay is complete, the rapid testing device 270 can be configured to output a test result, which can be detected and/or assessed by a human and/or one or more electronic devices, as described in detail above.

After the initial volume of bodily fluid is transferred and/or diverted into the rapid testing device 270, the transfer device 205 can be transitioned from the first state or configuration to a second state or configuration. For example, in some embodiments, the actuator 250 can be transitioned from its first state to its first state when the initial volume of bodily fluid is transferred into the rapid testing device 270, which in turn, places the transfer device 205 in its second state. In some embodiments, the arrangement of the transfer device 205 can be such that the transfer device 205 cannot transition to the second state prior to collecting the initial volume in the rapid testing device 270.

In some embodiments, the arrangement of the transfer device 205, the actuator 250, and/or the rapid testing device 270 can be such that a flow of bodily fluid into the rapid testing device 270 substantially stops or slows in response to receiving the initial volume. In some instances, the user can visually inspect a portion of the device 205 and/or housing 210 to determine that the initial volume of bodily fluid is disposed in the rapid testing device 270 and/or that the flow of bodily fluid into the rapid testing device 270 has slowed or substantially stopped. In some embodiments, the user can exert a force on the actuator 250 and/or can otherwise actuate the actuator 250 to transition the actuator 250 from its first state to its first state. In other embodiments, the actuator 250 can be transitioned automatically (e.g., without user intervention). Moreover, in some implementations, the device 205 and/or actuator 250 can be transitioned from the first state to the second state while the rapid testing device 270 is performing the test(s) or assay(s) on the initial volume of bodily fluid. Said another way, the rapid testing device 270 can perform the assay on the initial volume of bodily fluid while the device 205 is used to transfer one or more subsequent volumes of bodily fluid (e.g., in one or more parallel processes or the like).

In some embodiments, the transitioning of the actuator 250 from its first state to its second state (e.g., placing the transfer device 205 in its second state or configuration) can sequester, isolate, separate, and/or retain the initial volume of the bodily fluid in the rapid testing device 270. Said another way, the actuator 250 can sequester and/or isolate the rapid testing device 270 from the inlet 212, the outlet 213, and one or more portions of the fluid flow path 215. As described in further detail herein, in some instances, contaminants such as, for example, dermally residing microbes or the like dislodged during the venipuncture event, other external sources of contamination, colonization of catheters and PICC lines that are used to collect samples, and/or the like can be entrained and/or included in the initial volume of the bodily fluid. Thus, such contaminants are sequestered in the initial volume. Moreover, the arrangement of the rapid testing device 270 can be such that the tests and/or assays performed by the rapid testing device 270 are not susceptible to such contamination, which means that the accuracy of the test results output by the rapid testing device 270 is not affected by such contamination, as described in detail above.

In addition to sequestering the rapid testing device 270 from the inlet 212, the outlet 213, and at least a portion of the fluid flow path 215, placing the actuator 250 in its second state also establishes fluid communication between the inlet 212 and the outlet 213 via at least a portion of the fluid flow path 215. For example, in some embodiments, transitioning the actuator 250 from its first state to its second state can, for example, open or close a port or valve, move one or more seals, move or remove one or more obstructions, define one or more portions of a flow path, and/or the like.

In some implementations, the fluid collection device 295 can be fluidically coupled to the outlet 213 at any time prior to and/or at the same time as the actuator 250 being transitioned from the first state to the second state. As described above, the fluid collection device 295 can be any suitable reservoir, container, and/or device configured to receive a volume of bodily fluid. For example, the fluid collection device 295 can be an evacuated reservoir or container that defines a negative pressure and/or can be a syringe that can be manipulated to produce a negative pressure. In some instances, coupling the outlet 213 to the fluid collection device 295 selectively exposes at least a portion of the fluid flow path 215 to the negative pressure and/or suction force within the fluid collection device 295. Thus, in response to the negative pressure and/or suction force, one or more subsequent volume(s) of the bodily fluid can flow from the inlet 212, through at least a portion of the fluid flow path 215, through the outlet 213, and into the fluid collection device 295. As described above, sequestering the initial volume of bodily fluid (e.g., in the rapid testing device 270) prior to collecting or procuring one or more subsequent volumes of bodily fluid reduces and/or substantially eliminates an amount of contaminants in the one or more subsequent volumes. Accordingly, the subsequent volumes of bodily fluid can be used in one or more tests such as blood culture tests and/or the like, which may be relatively sensitive to contaminants (e.g., can produce adulterated results due to the presence of contaminants). In this manner, the system 200 can be configured to procure the initial volume of bodily fluid, which can be used in testing that has relatively low sensitivity to contamination, and the subsequent volume(s) of bodily fluid, which can be used in testing that has a relatively high sensitivity to contamination. In some instances, the testing of the initial volume of bodily fluid (e.g., by the rapid testing device 270) can provide relatively quick initial results that can inform one or more treatment options, while the testing of the subsequent volume(s) of bodily fluid can provide more detailed test results that typically take longer to develop.

Figure 4:
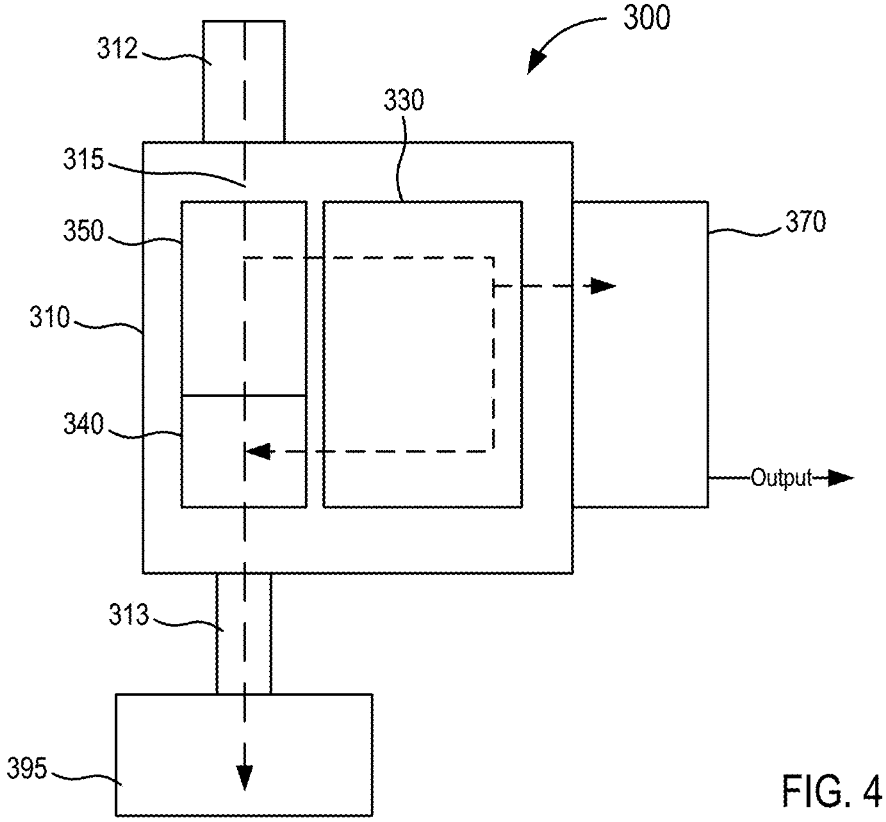
FIG. 4 is a schematic illustration of a fluid transfer and assay system according to an embodiment.

FIG. 4 is a schematic illustration a fluid transfer and assay system 300, according to an embodiment. The fluid transfer and assay system 300 (also referred to herein as "system") can include at least a fluid transfer device 305 and a rapid diagnostic testing device 370. In some implementations, the system 300 can include at least one fluid collection device 395 that can be physically and/or fluidically coupled to the fluid transfer device 305. Portions and/or aspects of the fluid transfer device 305, the rapid diagnostic testing device 370, and/or the fluid collection device 395 can be similar to and/or substantially the same as the fluid transfer devices 105 and/or 205, the rapid diagnostic testing devices 170 (and/or the LFA 170A) and/or 270, and/or the fluid collection devices 195 and/or 295, respectively, described in detail above with reference FIG. 3. Accordingly, such portions and/or aspects are not described in further detail herein.

The fluid transfer device 305 (also referred to herein as "transfer device") can be any suitable shape, size, and/or configuration. In some implementations, the transfer device 305 can be configured to withdraw bodily fluid (e.g., blood) from a patient and into and/or through the transfer device 305. In addition, the transfer device 305 can be configured to transfer at least some of the withdrawn bodily fluid to one or more other devices, reservoirs, containers, vials, machines, tests, assays, etc., such as the rapid diagnostic testing device 370 and/or one or more fluid collection devices 395.

The transfer device 305 includes a housing 310, a flow controller 340, and an actuator 350. The housing 310 of the device 305 can be any suitable shape, size, and/or configuration. For example, in some embodiments, the housing 310 can be similar to and/or the substantially the same as the housing 210 described above with reference to FIG. 3. Specifically, the housing 310 has and/or forms an inlet 312 and an outlet 313 and defines at least one fluid flow path 315 therebetween. The inlet 312 can be any suitable inlet or port and can be configured to establish fluid communication between the housing 310 to a bodily fluid source (e.g., a patient). The outlet 313 can be any suitable outlet or port and can be configured to establish fluid communication between the housing 310 and the fluid collection device 395. Moreover, the fluid collection device 395 can be similar to or substantially the same as the fluid collection device 295 and thus, is not described in further detail herein. The one or more fluid flow paths 315 defined by the housing 310 extends between the inlet 312 and the outlet 313 and can selectively establish fluid communication therebetween, as described in further detail herein.

The housing 310 can differ from the housing 210, however, by including, forming, and/or coupling to a sequestration chamber 330. As described in further detail herein, the sequestration chamber 330 is selectively in fluid communication with the fluid flow path 315. In addition, the sequestration chamber 330 includes, is coupled to, and/or is otherwise in fluid communication with the rapid diagnostic testing device 370. The sequestration chamber 330 can be configured to (1) receive a flow and/or volume of bodily fluid from the inlet 312, (2) sequester (e.g., separate, segregate, contain, retain, isolate, etc.) at least a portion of the flow and/or volume of bodily fluid therein, and (3) transfer at least a portion of the flow and/or volume of bodily fluid into the rapid diagnostic testing device, as described in further detail herein.

The sequestration chamber 330 can have any suitable arrangement such as, for example, those described herein with respect to specific embodiments. For example, in some embodiments, the sequestration chamber 330 can be at least partially formed by the housing 310. In other embodiments, the sequestration chamber 330 can be a reservoir placed and/or disposed within a portion of the housing 310. In other embodiments, the sequestration chamber 330 can be formed and/or defined by a portion of the fluid flow path 315. That is to say, the housing 310 can define one or more lumens and/or can include one or more lumen defining device(s) configured to receive an initial flow or volume of bodily fluid from the inlet 312, thereby forming and/or functioning as the sequestration chamber 330. While examples of a sequestration chamber are described herein, it should be understood that the transfer device 305 and/or the housing 310 can have a sequestration chamber arranged in any suitable manner and therefore, the sequestration chamber 330 is not intended to be limited to those shown and described herein.

The sequestration chamber 330 can have any suitable volume and/or fluid capacity. For example, in some embodiments, the sequestration chamber 330 can have a volume and/or fluid capacity between about 0.1 mL and about 5.0 mL. In some embodiments, the sequestration chamber 330 can have a volume measured in terms of an amount of bodily fluid (e.g., the initial or first amount of bodily fluid) configured to be transferred in the sequestration chamber 330. For example, in some embodiments, the sequestration chamber 330 can have a volume sufficient to receive an initial volume of bodily fluid as small as a microliter or less of bodily fluid (e.g., a volume as small as 20 drops of bodily fluid, 10 drops of bodily fluid, 5 drops of bodily fluid, a single drop of bodily fluid, or any suitable volume therebetween). In other embodiments, the sequestration chamber 330 can have a volume sufficient to receive an initial volume of bodily fluid up to, for example, about 5.0 mL, 10.0 mL, 15.0 mL, 20.0 mL, 30.0 mL, 40.0 mL, 50.0 mL, or more. In some embodiments, the sequestration chamber 330 can have a volume that is equal to at least some of the volumes of one or more lumen(s) placing the sequestration chamber 330 in fluid communication with the bodily fluid source (e.g., a combined volume of a lumen of a needle, the inlet 312, and at least a portion of the fluid flow path 315). In still other embodiments, the sequestration chamber 330 can have a volume that is based at least in part on a desired volume of bodily fluid used in or by the rapid diagnostic testing device 370.

As shown in FIG. 4, the device 305 includes the flow controller 340, which is at least partially disposed within the housing 310 and is configured to control, direct, and/or otherwise facilitate a selective flow of fluid through at least a portion of the housing 310, at least a portion of the fluid flow path 315, and/or at least a portion of the sequestration chamber 330. In this context, the flow of fluids, for example, can be a liquid such as water, oil, dampening fluid, bodily fluid, and/or any other suitable liquid, and/or can be a gas such as air, oxygen, carbon dioxide, helium, nitrogen, ethylene oxide, and/or any other suitable gas.

The flow controller 340 can be any suitable shape, size, and/or configuration. In some embodiments, the flow controller 340 can be, for example, a valve, a membrane, a diaphragm, a bladder, a plunger, a piston, a bag, a pouch, and/or any other suitable member having a desired stiffness, flexibility, and/or durometer, or any suitable combination thereof. In some embodiments, the flow controller 340 can be, for example, a restrictor, a vent, an absorbent member, a selectively permeable member (e.g., a fluid impermeable barrier or seal that at least selectively allows the passage of air or gas therethrough), a port, a junction, an actuator, and/or the like, or any suitable combination thereof. In some embodiments, the flow controller 340 can be similar to or substantially the same as any of those described in the '117 publication; U.S. Patent Publication No. 2019/0076074 entitled, "Fluid Control Devices and Methods of Using the Same," filed Sep. 12, 2018 ("the '074 publication"); U.S. patent application Ser. No. 16/426,380 entitled, "Fluid Control Devices and Methods of Using the Same," filed May 30, 2019 ("the '380 application"); and/or U.S. Provisional Patent Application Ser. No. 62/816,477 entitled, "Fluid Control Devices and Methods of Using the Same," filed Mar. 11, 2019 ("the '477 application"), the disclosure of each of which is incorporated herein by reference in its entirety.

In some embodiments, the transfer device 305 can be configured to selectively transfer a volume of bodily fluid to the sequestration chamber 330 or to the outlet 313 based at least in part on a pressure differential between two or more portions of the transfer device 305. For example, a pressure differential can result from fluidically coupling the outlet 313 to the fluid collection device 395, which can define and/or can be configured to produce a negative pressure (e.g., an evacuated reservoir, a syringe, a pressure charged canister, and/or other source or potential energy to create a vacuum or pressure differential). In other embodiments, the pressure differential can result from a change in volume and/or temperature. In still other embodiments, the pressure differential can result from at least a portion of the transfer device 305, the housing 310, the actuator 350, and/or portions of the fluid flow path 315 being evacuated and/or charged (e.g., the sequestration chamber 330 and/or any other suitable portion). In some embodiments, the pressure differential can be established automatically or via direct or indirect intervention (e.g., by the user).

In some embodiments, the flow controller 340 can be configured to facilitate air (or other fluid) displacement through one or more portions of the transfer device 305, which in some instances, can allow for or result in a pressure differential and/or pressure equalization across one or more portions of the housing 310. Moreover, a flow of a fluid (e.g., gas and/or liquid) resulting from a pressure differential can be selectively controlled via the flow controller 340. For example, the flow controller 340 can be configured to transition between one or more operating states or conditions to control the fluid flow. In some embodiments, the flow controller 340 can be a member or device formed of an absorbent or semi-permeable material configured to selectively allow fluid flow therethrough. For example, such an absorbent material can be transitioned from a first state in which the material allows a flow of gas (e.g., air) therethrough but prevents a flow of liquid (e.g., bodily fluid) therethrough, to a second state in which the material substantially prevents a flow of gas and liquid therethrough (e.g., the flow controller 340 can be a selectively permeable blood barrier), as described in detail in the '117 publication and/or the '380 application.

In some embodiments, the flow controller 340 can be configured to transition from a first state to a second state in response to a negative pressure differential and/or suction force exerted on at least a portion of the flow controller 340. For example, the flow controller 340 can include one or more valves, membranes, diaphragms, and/or the like. For example, the flow controller 340 can be in a first state prior to using the device 305 (e.g., a storage or non-use state) and in response to the outlet 313 being fluidically coupled to the fluid collection device 395 (e.g., a collection device defining or configured to define a negative pressure and/or suction force), the flow controller 340 can be transitioned to a second state. In some embodiments, the flow controller 340 can be a bladder configured to transition or "flip" from a first state to a second state in response to a negative pressure differential and/or suction force exerted on a surface of the bladder, as described in detail in the '380 application and/or the '477 application.

In some embodiments, a size, shape, arrangement, and/or constituent material of the flow controller 340 can be configured and/or otherwise selected such that the flow controller 340 transitions from the first state to the second state in a predetermined manner and/or with a predetermined or desired rate. In some instances, controlling a rate at which the flow controller 340 transitions from the first state to the second state can, in turn, control and/or modulate a rate of bodily fluid flow into the sequestration chamber 330 and/or a magnitude of a suction force generated in the sequestration chamber 330 that is operable in drawing the initial volume of bodily fluid into the sequestration chamber 330. Although not shown in FIG. 4, in some embodiments, the housing 310 and/or the flow controller 340 can include any suitable member, feature, opening, etc., configured to modulate a suction force exerted on or through the flow controller 340, which in turn, can modulate the rate at which the flow controller 340 transitions from the first state to the second state. In some instances, controlling a rate at which the flow controller 340 transitions and/or a magnitude of a pressure differential and/or suction force generated within the sequestration chamber 330 can reduce, for example, hemolysis of a blood sample and/or a likelihood of collapsing a vein (e.g., which is particularly important when procuring bodily fluid samples from fragile patients). In some instances, modulating the transitioning of the flow controller 340 and/or the pressure differential generated in the sequestration chamber 330 can at least partially control an amount or volume of bodily fluid transferred into the sequestration chamber 330 (i.e., can control a volume of the initial amount of bodily fluid).

In some embodiments, the flow controller 340 can include any suitable combination of devices, members, and/or features. It should be understood that the flow controllers included in the embodiments described herein are presented by way of example and not limitation. Thus, while specific flow controllers are described herein, it should be understood that fluid flow can be controlled through the transfer device 305 by any suitable manner.

The actuator 350 of the device 305 is at least partially disposed within the housing 310 and is configured to control, direct, and/or otherwise facilitate a selective flow of fluid through at least a portion of the housing 310 and/or at least a portion of the one or more fluid flow paths 315. The actuator 350 can be any suitable shape, size, and/or configuration. In some embodiments, the actuator 350 can be a member or device configured to transition between any number of states and in any suitable manner. In addition, the actuator 350 can be actuated in any suitable manner (e.g., user actuation, automatic actuation, mechanical actuation, electronic actuation, chemical actuation, and/or the like). For example, the actuator 350 can be the similar to and/or substantially the same as any of those described above with reference to the actuator 250.

In the embodiment shown in FIG. 4, the actuator 350 can be configured to selectively establish fluid communication between the inlet 312 and the sequestration chamber 330 when in a first state and to selectively establish fluid communication between the inlet 312 and the outlet 313 when in a second state. When in the first state, the actuator 350 can be configured to allow bodily fluid to from the inlet 312, through at least a portion of the fluid flow path 315 and to or into the sequestration chamber 330. In some embodiments, the actuator 350 can be configured to sequester, separate, isolate, and/or otherwise prevent fluid communication between the outlet 313 and inlet 312, at least a portion of the fluid flow path 315, and/or the sequestration chamber 330. When in the second state, the actuator 350 can be configured to allow a subsequent volume of bodily fluid (e.g., a volume of bodily fluid after the initial volume of bodily fluid) to be transferred from the inlet 312, through at least a portion of the fluid flow path 315, and to the outlet 313 (and/or the fluid collection device 395 fluidically coupled to the outlet 313), as described in further detail herein. In addition, when in the second state, the actuator 350 can be configured to sequester, separate, isolate, and/or otherwise prevent fluid communication between the sequestration chamber 330 and the inlet 312, the outlet 313, and/or at least a portion of the fluid flow path 315. In the embodiment shown in FIG. 4, the transfer device 305 is such that the actuator 350 and the flow controller 340 collectively control the flow of fluid (e.g., a gas and/or a liquid) through the device, as described in further detail herein.

The rapid diagnostic testing device 370 (also referred to herein as "rapid testing device" or simply "testing device") can be any suitable shape, size, and/or configuration. In some embodiments, the rapid testing device 370 can be removably coupled to the transfer device 305 or any suitable portion thereof. For example, in the embodiment shown in FIG. 4, the rapid testing device 370 can be at least fluidically coupled to the sequestration chamber of the transfer device 305. In other embodiments, the rapid testing device 370 can be integrated into the transfer device 305 such that the rapid testing device 370 is in fluid communication with the sequestration chamber 330. For example, the transfer device 305 and the rapid testing device 370 can be unitarily or monolithically formed and/or otherwise integrated. In still other embodiments, the housing 310 can include and/or can form a port, adapter, and/or receiving portion to which the rapid testing device 370 can be coupled or into which the rapid testing device 370 can be inserted to establish fluid communication between the rapid testing device 370 and the sequestration chamber 330.

In some such embodiments, coupling the rapid testing device 370 to the transfer device 305 can be operable to transition one or more flow controllers, valves, septa, ports, seals, etc. from a closed or sealed state to an open state to allow fluid communication between the transfer device 305 and the testing device 370. Although not shown in FIG. 4, in some embodiments, the transfer device 305 can include a second actuator and/or the like that can be manipulated to establish fluid communication between the sequestration chamber 330 and the rapid testing device 370. In other embodiments, the actuator 350 can be transitioned to establish fluid communication between the sequestration chamber 330 and the rapid testing device 370.

In some implementations, the rapid testing device 370 can be configured to receive the first amount of bodily fluid from the transfer device 305 and to use the first amount of bodily fluid to perform one or more tests, assays, and/or diagnostic procedures. The rapid testing device 370 can be any suitable testing device. For example, the rapid testing device 370 can be an LFA or the like, as described in detail above with reference to the LFA 170A shown in FIG. 2. In some implementations, the testing device 370 and/or aspects or portions thereof can be substantially similar to the rapid testing devices 170 and/or 270 described in detail above. Accordingly, the rapid testing device 370 and/or aspects or portions thereof is/are not described in further detail herein.

As described above, the system 300 can be used to procure one or more volumes of bodily fluid from a patient, which can be used in one or more tests, assays, and/or diagnostic procedures. For example, in some instances, a user such as a doctor, physician, nurse, phlebotomist, technician, etc. can manipulate the device 305 to establish fluid communication between the inlet 312 and the bodily fluid source (e.g., a vein of a patient, cerebral spinal fluid (CSF) from the spinal cavity, urine collection, and/or the like), as described above. In some instances, the actuator 350 can be in a first state when the inlet 312 is placed in fluid communication with the bodily fluid source (e.g., the portion of the patient), such that at least a portion of the fluid flow path 315 establishes fluid communication between the inlet 312 and the sequestration chamber 330.

As such, the transfer device 305 can be configured to transfer an initial volume of bodily fluid from the bodily fluid source (e.g., the patient) to the rapid testing device 370. More specifically, in the embodiment shown in FIG. 4, once the inlet 312 is placed in fluid communication with the bodily fluid source (e.g., the portion of the patient), the outlet 313 can be fluidically coupled to the fluid collection device 395. As described above, in some embodiments, the fluid collection device 395 can be any suitable reservoir, container, and/or device configured to receive a volume of bodily fluid. For example, the fluid collection device 395 can be an evacuated reservoir or container that defines a negative pressure and/or can be a syringe that can be manipulated to produce a negative pressure. In some instances, coupling the outlet 313 to the fluid collection device 395 selectively exposes at least a portion of the fluid flow path 315 to the negative pressure and/or suction force within the fluid collection device 395. In some implementations, the actuator 350 can be in the first state such that the outlet 313 is sequestered from the inlet 312. In addition, when the actuator 350 is in the first state, the outlet 313 can be in fluid communication with the flow controller 340 (e.g., via a portion of the fluid flow path 315). The flow controller 340 can similarly be in its first state when the fluid collection device 395 is coupled to the outlet 313.

In embodiments in which the flow controller 340 is a selectively permeable member or membrane, the arrangement of the flow controller 340 and the actuator 350 can be such that a flow of air or gas is allowed to pass through the flow controller 340 between the outlet 313 and the sequestration chamber 330. In such embodiments, this arrangement results in at least a portion of the negative pressure differential or suction force generated by the fluid collection device 395 being transferred into and/or through the sequestration chamber 330, which in turn, can be operable in drawing the initial volume of bodily fluid from the bodily fluid source, through the inlet 312 and at least a portion of the fluid flow path 315, and into the sequestration chamber 330, as described in detail in the '117 publication and/or the '380 application.

Alternatively, in embodiments in which the flow controller 340 is a diaphragm, flap, valve, sleeve, etc., the arrangement of the flow controller 340 and the actuator 350 can be such that a portion and/or surface of the flow controller 340 is in fluid communication with the outlet 313 (e.g., via a portion of the fluid flow path 315). As such, the negative pressure and/or suction force can be exerted on the portion and/or surface of the flow controller 340, which in turn, can be operable to transition the flow controller 340 from its first state, in which the sequestration chamber 330 has a first volume, to its second state, in which the sequestration chamber 330 has a second volume, greater than the first volume. The sequestration chamber 330 can be such that the increase in volume results in a decrease in pressure within the sequestration chamber 330, thereby generating a negative pressure differential operable to draw bodily fluid into the sequestration chamber 330. Thus, in such embodiments, the initial volume of bodily fluid can be drawn into the sequestration chamber 330 in response to the transitioning of the flow controller 340 (e.g., the increase in volume of the sequestration chamber 330 as a result of the flow controller 340 transitioning from the first state to the second state), as described in detail in the '380 application and/or the '477 application.

The initial volume of bodily fluid can be any suitable volume of bodily fluid, such as any of the volumes or amounts described above. For example, in some instances, the transfer device 305 can remain in the first state or configuration until a predetermined and/or desired volume (e.g., the initial volume) of bodily fluid is transferred to the sequestration chamber 330. In some embodiments, the initial volume can be associated with and/or at least partially based on a volume of the sequestration chamber 330 or a portion thereof (e.g., a volume sufficient to fill the sequestration chamber 330 or a desired portion of the sequestration chamber 330). In some embodiments, the initial volume can be associated with and/or at least partially based on a desired volume sufficient for the rapid testing device 370 to perform one or more tests or assays. In other embodiments, the initial volume of bodily fluid can be associated with and/or at least partially based on an amount or volume of bodily fluid that is equal to or greater than a volume associated with the fluid flow path defined between the bodily fluid source and the sequestration chamber 330. In still other embodiments, the transfer device 305 can be configured to transfer a flow of bodily fluid (e.g., the initial volume) into the sequestration chamber 330 until a pressure differential between the sequestration chamber 330 and the inlet 312 or the bodily fluid source is brought into substantial equilibrium and/or is otherwise reduced below a desired threshold.

In some embodiments, the transfer device 305 can be configured to transfer a flow of bodily fluid (e.g., the initial volume) into the sequestration chamber 330 until the flow controller 340 is transitioned to its second configuration. Said another way, in some embodiments, transferring the initial volume of bodily fluid into the sequestration chamber 330 can be operable to place the flow controller 340 in its second state or configuration. For example, in embodiments in which the flow controller 340 is a selectively permeable member, transferring the initial volume of bodily fluid into the sequestration chamber 330 can be such that at least a portion of the initial volume wets and/or saturates the flow controller 340, which in turn, places the flow controller 340 in its second state, as described in detail in the '117 application and/or the '380 application. In embodiments in which the flow controller 340 is a diaphragm and/or the like, the transferring of the initial volume into the sequestration chamber 330 can substantially coincide with the flow controller 340 being placed in its second state and/or configuration (e.g., in response to the negative pressure produced by the fluid collection device 395), as described in detail in the '380 application and/or the '477 application. Moreover, in the embodiment shown in FIG. 4, the arrangement of the flow controller 340 is such that when in its second state and/or configuration, the flow controller 340 sequesters and/or fluidically isolates the sequestration chamber 330 from the outlet 313 such that the negative pressure and/or suction force produced by the fluid collection device 395 no longer acts on or through the sequestration chamber 330.

In some implementations, at least a portion of the initial volume of bodily fluid can be transferred from the sequestration chamber 330 and into the rapid testing device 370 when the flow controller 340 is in its second state and prior to the actuator being transitioned from its first state to its second state. In some embodiments, the actuator 350 is configured to sequester the sequestration chamber 330 from the inlet 313, the outlet 315, and at least a portion of the fluid flow path 315. In such embodiments, the portion of the initial volume of bodily fluid can be transferred from the sequestration chamber 330 prior to transitioning the actuator 350 from its first state to its second state, during the transitioning, and/or after transitioning the actuator 350 from its first state to its second state. In some implementations, the transferring of the portion of the initial volume can be automatic. In other implementations, the transferring of the portion of the initial volume can be in response to one or more user inputs and/or the like.

In some embodiments, transferring the portion of the initial volume of bodily fluid into the rapid testing device 370 can initiate a test and/or assay of or on the portion of the initial volume of bodily fluid, as described in detail above with reference to the rapid testing device 270. Moreover, the rapid testing device 370 can be configured to perform any suitable test and/or assay. For example, the rapid testing device 370 can be an LFA configured to test for the presence of lactate and/or PCT, as described in detail above. Moreover, once the test or assay is complete, the rapid testing device 370 can be configured to output a test result, which can be detected and/or assessed by a human and/or one or more electronic devices, as described in detail above.

In some embodiments, the transitioning of the actuator 350 from its first state to its second state (e.g., placing the transfer device 305 in its second state or configuration) can sequester, isolate, separate, and/or retain the initial volume of the bodily fluid in the sequestration chamber 330 and/or the rapid testing device 370. Said another way, the actuator 350 can sequester and/or isolate the sequestration chamber 330 from the inlet 312, the outlet 313, and one or more portions of the fluid flow path 315. In some instances, sequestering the initial volume of bodily fluid in the sequestration chamber 330 can also sequester contaminants in the initial volume. Moreover, the arrangement of the rapid testing device 370 can be such that the tests and/or assays performed by the rapid testing device 370 are not susceptible to such contamination, which means that the accuracy of the test results output by the rapid testing device 370 is not affected by such contamination, as described in detail above.

In addition to sequestering the sequestration chamber 330 from the inlet 312, the outlet 313, and at least a portion of the fluid flow path 315, placing the actuator 350 in its second state (and having the flow controller 340 in its second state) also establishes fluid communication between the inlet 312 and the outlet 313 via at least a portion of the fluid flow path 315. For example, in some embodiments, transitioning the actuator 350 from its first state to its second state can, for example, open or close a port or valve, move one or more seals, move or remove one or more obstructions, define one or more portions of a flow path, and/or the like. Thus, in response to the negative pressure and/or suction force generated by the fluid collection device 395, one or more subsequent volume(s) of the bodily fluid can flow from the inlet 312, through at least a portion of the fluid flow path 315, through the outlet 313, and into the fluid collection device 395. As described above, sequestering the initial volume of bodily fluid (e.g., in the rapid testing device 370) prior to collecting or procuring one or more subsequent volumes of bodily fluid reduces and/or substantially eliminates an amount of contaminants in the one or more subsequent volumes. Accordingly, the system 300 can be configured to procure the initial volume of bodily fluid, which can be used in rapid testing that has relatively low sensitivity to contamination, and the subsequent volume(s) of bodily fluid, which can be used in testing that has a relatively high sensitivity to contamination, as described above with reference to the systems 100 and/or 200.

Figure 5A:
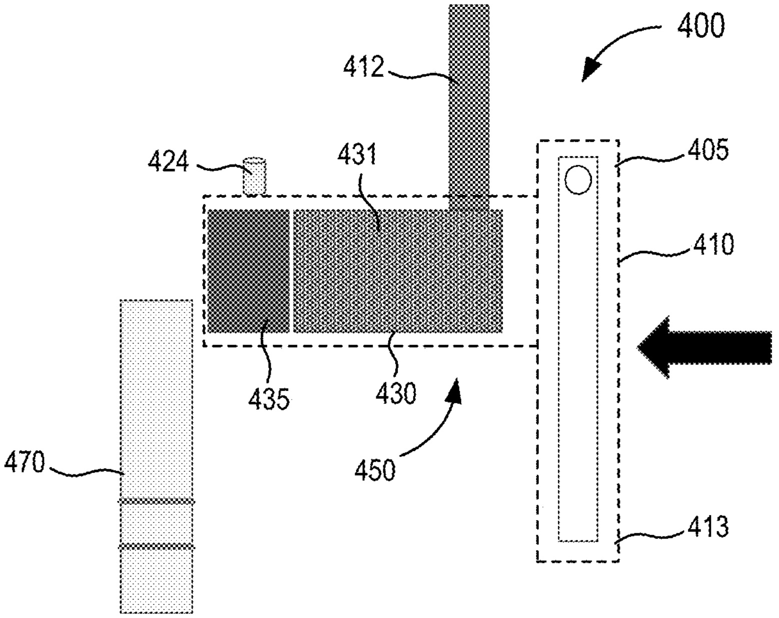
FIGS. 5A and 5B are schematic illustrations of a fluid transfer and assay system in a first state and a second state, respectively, according to an embodiment.
Figure 5B:
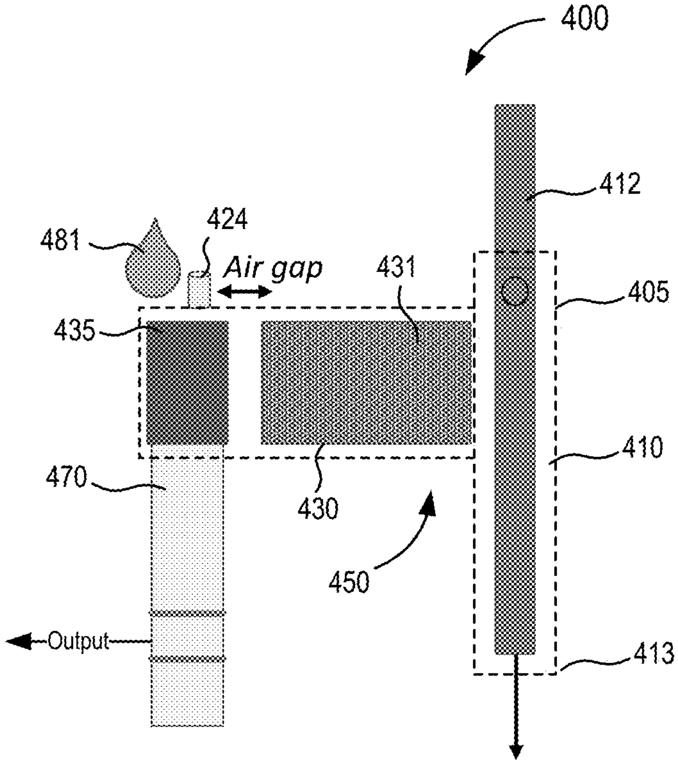

FIGS. 5A and 5B are schematic illustrations a fluid transfer and assay system 400, according to an embodiment, and shown in a first state and a second state, respectively. The fluid transfer and assay system 400 (also referred to herein as "system") can include at least a fluid transfer device 405 and a rapid diagnostic testing device 470. Portions and/or aspects of the fluid transfer device 405 and/or the rapid diagnostic testing device 470 can be similar to and/or substantially the same as the fluid transfer devices 105, 205, and/or 305, and/or the rapid diagnostic testing devices 170 (and/or the LFA 170A), 270 and/or 370, respectively, described in detail above. Accordingly, such portions and/or aspects are not described in further detail herein.

The fluid transfer device 405 (also referred to herein as "transfer device") can be any suitable shape, size, and/or configuration. In some implementations, the transfer device 405 can be configured to withdraw bodily fluid (e.g., blood) from a patient and into and/or through the transfer device 405. In addition, the transfer device 405 can be configured to transfer at least some of the withdrawn bodily fluid to one or more other devices, reservoirs, containers, vials, machines, tests, assays, etc., such as the rapid diagnostic testing device 470 and/or one or more fluid collection devices (not shown in FIGS. 5A and 5B).

The transfer device 405 includes at least a housing 410 and an actuator 450. The housing 410 of the device 405 can be any suitable shape, size, and/or configuration. For example, in some embodiments, the housing 410 can be similar to and/or the substantially the same as the housings 210 and/or 310 described above. Specifically, the housing 410 has and/or forms an inlet 412 and an outlet 413 and can define at least one fluid flow path therebetween (not shown in FIGS. 5A and 5B). The inlet 412 can be any suitable inlet or port and can be configured to establish fluid communication between the housing 410 to a bodily fluid source (e.g., a patient). The outlet 413 can be any suitable outlet or port and can be configured to establish fluid communication between the housing 410 and a fluid collection device (not shown in FIGS. 5A and 5B), such as any of those described in detail above. The one or more fluid flow paths defined by the housing 410 extend between the inlet 412 and the outlet 413 and can selectively establish fluid communication therebetween, as described in further detail herein.

As described above with reference to the housing 310, the housing 410 shown in FIGS. and 5B includes, forms, and/or couples to a sequestration chamber 430 configured to be selectively placed in fluid communication with the fluid flow path and/or at least the inlet 412. In addition, the sequestration chamber 430 includes, is coupled to, and/or is otherwise configured to be placed in fluid communication with the rapid diagnostic testing device 470. The sequestration chamber 430 can have any suitable shape, size, and/or configuration. For example, in some embodiments, the sequestration chamber 430 can have a volume and/or fluid capacity between about 0.1 mL and about 5.0 mL. In some embodiments, the sequestration chamber 430 can have a volume measured in terms of an amount of bodily fluid (e.g., the initial or first amount of bodily fluid) configured to be transferred into the sequestration chamber 430 and/or configured to be tested by the rapid diagnostic testing device 470. In some embodiments, the sequestration chamber 430 and/or at least a portion thereof can be substantially similar in at least form and/or function to the sequestration chamber 330 described above with reference to FIG. 4. Thus, portions and/or aspects of the sequestration chamber 430 are not described in further detail herein.

In the embodiment shown in FIGS. 5A and 5B, at least a portion of the sequestration chamber 430 can include an absorbent and/or hydrophilic material 431. In addition, the sequestration chamber 430 includes a sampling portion 435 and a vent 424. The absorbent material 431 can be disposed within a portion of the sequestration chamber 430. For example, one or more inner surfaces of the sequestration chamber 431 can be lined with and/or formed by the absorbent material 431. As shown in FIGS. 5A and 5B, the arrangement of the sequestration chamber 430 can be such that a sampling portion 435 of the sequestration chamber 430 is downstream of the absorbent material 431 (e.g., relative to a portion of the sequestration chamber 430 is temporarily fluidically coupled to the inlet 412. In this manner, the absorbent material 431 can be configured to receive and/or absorb a first portion or part of an initial volume of bodily fluid transferred into the sequestration chamber 430. In some implementations, the absorbent material 431 can become saturated after absorbing a predetermined amount or volume of bodily fluid such that any additional amount or volume of bodily fluid transferred into the sequestration chamber 430 can flow into the sampling portion 435. As described in further detail herein, the sampling portion 435 of the sequestration chamber 430 can be placed in fluid communication with the rapid diagnostic testing device 470 to transfer a part of the initial volume of bodily fluid disposed in the sampling portion 435 into the rapid diagnostic testing device 470.

The vent 424 is coupled to the housing 410 and/or the sequestration chamber 430 and is in fluid communication with an internal volume of the sequestration chamber 430. The vent 424 can be configured to vent and/or otherwise allow a flow of air or gas out of the sequestration chamber 430 as the initial volume of bodily fluid is transferred into the sequestration chamber 430. In some implementations, venting air or gas out of the sequestration chamber 430 (e.g., via the vent 424) can reduce an amount of pressure within the sequestration chamber 430 that may otherwise limit and/or impede the flow of bodily fluid into the sequestration chamber 430. In some implementations, venting air or gas through the vent 424 can allow for a negative pressure differential that can facilitate the transfer of the initial volume of bodily fluid into the sequestration chamber 430. While the absorbent material 431 and the vent 424 are shown in FIGS. 5A and 5B as being separate components, in other embodiments, the absorbent material 431 can form one or more vents configured to vent the sequestration chamber 430 as well as being configured to absorb a first part or portion of the initial volume. For example, the absorbent material 431 can form one or more walls or one or more portions of a wall of the sequestration chamber 430.

The actuator 450 of the device 405 can be any suitable shape, size, and/or configuration. In some embodiments, the actuator 450 and/or aspects or portions thereof can be similar to and/or substantially the same as the actuators 150, 250, and/or 350 described in detail above. In some embodiments, the actuator 450 can be at least partially disposed within and/or partially formed by the housing 410. As described above, the actuator 450 can be configured to control, direct, and/or otherwise facilitate a selective flow of fluid through at least a portion of the housing 410 and/or at least a portion of the one or more fluid flow paths. In some embodiments, the actuator 450 can be a member or device configured to transition between any number of states (e.g., two, three, four, or more) and in any suitable manner (e.g., user actuation, automatic actuation, mechanical actuation, electronic actuation, chemical actuation, and/or the like).

More particularly, in the embodiment shown in FIGS. 5A and 5B, the actuator 450 can be configured to transition between a first state in which the inlet 412 is in fluid communication with the sequestration chamber 430 (FIG. 5A) and a second state in which the inlet 412 is in fluid communication with the outlet 413 (FIG. 5B). In some embodiments, the actuator 450 can be configured to sequester, separate, isolate, and/or otherwise prevent fluid communication between the outlet 413 and inlet 412 and/or the outlet 413 and the sequestration chamber 430 when in the first state. Conversely, in the second state, the actuator 450 can be configured to allow a subsequent volume of bodily fluid (e.g., a volume of bodily fluid after the initial volume of bodily fluid) to be transferred from the inlet 412, through one or more fluid flow paths (not shown in FIGS. 5A and 5B) and to the outlet 413 (and/or a fluid collection device fluidically coupled to the outlet 413). In addition, when in the second state, the actuator 450 can be configured to sequester, separate, isolate, and/or otherwise prevent fluid communication between the sequestration chamber 430 and the inlet 412, the sequestration chamber 430 and the outlet 413, and/or the sequestration chamber 430 and at least a portion of the fluid flow path extending between the inlet 412 and the outlet 413. As such, the actuator 450 can be structurally and/or functionally similar to the actuators 150, 250, and/or 350 described in detail above.

The rapid diagnostic testing device 470 (also referred to herein as "rapid testing device" or simply "testing device") can be any suitable shape, size, and/or configuration. In some embodiments, the rapid testing device 470 can be removably coupled to the transfer device 405 or any suitable portion thereof. For example, in the embodiment shown in FIGS. 5A and 5B, the rapid testing device 470 can be configured to engage or couple to the housing 410 and/or sequestration chamber 4350 such that the rapid testing device 470 is placed in fluid communication with the sampling portion 435 of the sequestration chamber 430. In some embodiments, the housing 410 can include and/or can form a port, adapter, and/or receiving portion to which the rapid testing device 470 can be coupled or into which the rapid testing device 470 can be inserted to establish fluid communication between the rapid testing device 470 and the sampling portion 435 of the sequestration chamber 430. Moreover, in the embodiment shown in FIGS. 5A and 5B, transitioning the actuator 450 from its first state to its second state can establish fluid communication between the sequestration chamber 430 and the rapid testing device 470 (e.g., via one or more flow controllers, valves, septa, ports, seals, aligned flow paths, and/or other suitable member or device for establishing fluid communication). In some embodiments, transitioning the actuator 450 from its first state to its second state can establish fluid communication between the sequestration chamber 430 and the rapid testing device 470.

In some implementations, the rapid testing device 470 can be configured to receive the first amount of bodily fluid from the sampling portion 435 of the sequestration chamber 430 and to use the first amount of bodily fluid to perform one or more tests, assays, and/or diagnostic procedures. The rapid testing device 470 can be any suitable testing device. For example, the rapid testing device 470 can be an LFA or the like, as described in detail above with reference to the LFA 170A shown in FIG. 2. In some implementations, the testing device 470 and/or aspects or portions thereof can be substantially similar to the rapid testing devices 170, 270, and/or 370 described in detail above. Accordingly, the rapid testing device 470 and/or aspects or portions thereof is/are not described in further detail herein.

The system 400 can be used to procure one or more volumes of bodily fluid from a patient, which can be used in one or more tests, assays, and/or diagnostic procedures. As described above, for example, the inlet 412 can be placed in fluid communication with a bodily fluid source. In some instances, the actuator 450 can be in a first state when the inlet 412 is placed in fluid communication with the bodily fluid source (e.g., the portion of the patient), thereby establishing fluid communication between the inlet 412 and the sequestration chamber 430 and sequestering the outlet 413 from the inlet 412, as shown in FIG. 5A. As such, the transfer device 405 can be configured to transfer an initial volume of bodily fluid from the bodily fluid source (e.g., the patient) to the rapid testing device 470. In some implementations, the initial volume of bodily fluid can flow to and/or into the sequestration chamber 430 in response to a pressure differential between the sequestration chamber 430 and the inlet 412 and/or the bodily fluid source. In some embodiments, the vent 424 can be configured to allow a flow of air or gas out of the sequestration chamber 430, which can facilitate the flow of the initial volume of bodily fluid into the sequestration chamber 430. In some embodiments, the vent 424 can be configured to vent the sequestration chamber 430 in a manner similar to the vents and/or the like described, for example, in the '117 publication.

The initial volume of bodily fluid can be any suitable volume of bodily fluid, such as any of the volumes or amounts described above. More specifically, in the embodiment shown in FIGS. 5A and 5B, the initial volume of bodily fluid can be sufficient to saturate and/or wet (or substantially saturate and/or wet) the absorbent material 431 disposed in the sequestration chamber 430 and to fill (or substantially fill) the sampling portion 435 of the sequestration chamber 430. In some embodiments, the filling of the sequestration chamber 430 can be serial in that the flow of the initial volume of bodily fluid is first absorbed by the absorbent material 431 until the absorbent material 431 is saturated and then a remaining portion of the initial volume of bodily fluid can flow into and/or fill the sampling portion 435 of the sequestration chamber 430. In some implementations, serially filling the sequestration chamber 430 can be such that the portion of the initial volume of bodily fluid (e.g., a first portion) can contain contaminants (e.g., associated with and/or resulting from a venipuncture event, fluidically coupling one or more components, and/or the like), while the portion of the initial volume of bodily fluid (e.g., a second portion) can contain a reduced amount of contaminants and/or can be substantially free of contaminants. In some instances, once the initial volume of bodily fluid is transferred into the sequestration chamber 430, the flow of bodily fluid can stop and/or a pressure differential can be substantially equalized that can slow or stop the flow of bodily fluid.

In some embodiments, after transferring the initial volume of bodily fluid into the sequestration chamber 430, the actuator 450 can be transitioned from its first state (FIG. 5A) to its second state (FIG. 5B). For example, in some embodiments, the actuator 450 can be moved, slid, switched, rotated, and/or otherwise transitioned relative to the inlet 412 and the outlet 413. In some embodiments, transitioning and/or moving the actuator 450 can include transitioning and/or moving at least a portion of the housing 410. In other embodiments, the actuator 450 can be moved relative to the housing 410 (e.g., the housing 410 need not be transitioned and/or moved).

As shown in FIG. 5B, transitioning the actuator 450 from the first state to the second state can establish fluid communication between the sampling portion 435 of the sequestration chamber 430 and the rapid testing device 470, and can sequester the sequestration chamber 430 from the inlet 412, the outlet 413, and/or one or more portions of the fluid flow path therebetween. In some embodiments, the arrangement of the actuator 450 can be such that placing the actuator 450 in the second state results in and/or increases an air gap between a portion of the sequestration chamber 430 including the absorbent material 431 and a portion of the sequestration chamber 430 including, forming, and/or defining the sampling portion 435. The air gap can facilitate the transfer of bodily fluid from the sampling portion 435 to the rapid testing device 470 (e.g., by allowing a desired relative pressure or pressure differential). In addition, in instances in which contaminants are contained in the portion of the initial volume absorbed by the absorbent material 431, such an arrangement can ensure that only the portion of the initial volume disposed in the sampling portion 435 of the sequestration chamber 430 is transferred to the rapid testing device 470.

At least a portion of the initial volume of bodily fluid can be transferred from the sampling portion 435 of the sequestration chamber 430 and into the rapid testing device 470 when the actuator 450 is transitioned from its first state to its second state. In some implementations, the transferring of the portion of the initial volume can be automatic. In other implementations, the transferring of the portion of the initial volume can be in response to one or more user inputs and/or the like. In some implementations, the placement of the actuator 450 in the second state can fluidically couple the rapid testing device 470 to the sampling portion 435 of the sequestration chamber 430, thereby allowing the fluid transfer therebetween.

In some embodiments, transferring the portion of the initial volume of bodily fluid into the rapid testing device 470 can initiate a test and/or assay of or on the portion of the initial volume of bodily fluid, as described in detail above with reference to the rapid testing device 270. In some instances, the system 400, the transfer device 405, and/or the rapid testing device 470 can be configured to provide a buffer 481 (or any other suitable solution) that can be mixed with the portion of the initial volume of bodily fluid, as shown in FIG. 5B. The rapid testing device 470 can be configured to perform any suitable test and/or assay. For example, the rapid testing device 470 can be an LFA configured to test for the presence of lactate and/or PCT, as described in detail above. Moreover, once the test or assay is complete, the rapid testing device 470 can be configured to output a test result, which can be detected and/or assessed by a human and/or one or more electronic devices, as described in detail above with reference to the rapid testing devices 170, 270, and/or 370.

Transitioning the actuator 450 from its first state to its second state can sequester, isolate, separate, and/or retain the initial volume of the bodily fluid in the sequestration chamber 430 and/or the rapid testing device 470. Said another way, the actuator 450 can sequester and/or isolate the sequestration chamber 430 from the inlet 412, the outlet 413, and one or more portions of the fluid flow path. In some instances, sequestering the initial volume of bodily fluid in the sequestration chamber 430 can also sequester contaminants in the initial volume (e.g., at least the portion of the initial volume absorbed by the absorbent material 431). Moreover, the arrangement of the rapid testing device 470 can be such that the tests and/or assays performed by the rapid testing device 470 are not susceptible to such contamination, which means that the accuracy of the test results output by the rapid testing device 470 is not affected by such contamination, as described in detail above. In other instances, having the first part or portion of the initial volume of bodily fluid received and/or absorbed by the absorbent material 431 can allow the rapid testing device 470 to perform one or more tests that may be at least partially sensitive to contaminants.

In addition, transitioning the actuator 450 to its second state establishes fluid communication between the inlet 412 and the outlet 413 via at least a portion of the fluid flow path disposed therebetween. For example, transitioning the actuator 450 from its first state to its second state can open or close a port or valve, move one or more seals, move or remove one or more obstructions, define one or more portions of a flow path, and/or the like. In some implementations, the outlet 413 can be placed in fluid communication with a fluid collection device prior to or after the actuator is placed in its second state. As described in detail above, the fluid collection device can define and/or can be configured to generate a negative pressure and/or suction force that can be operable to draw bodily fluid into the fluid collection device. Thus, in response to the negative pressure and/or suction force, one or more subsequent volume(s) of the bodily fluid can flow from the inlet 412, through any suitable fluid flow path or portion thereof, through the outlet 413, and into the fluid collection device. As described above, sequestering the initial volume of bodily fluid in the sequestration chamber 430 prior to collecting or procuring one or more subsequent volumes of bodily fluid reduces and/or substantially eliminates an amount of contaminants in the one or more subsequent volumes. Accordingly, the system 400 can be configured to procure the initial volume of bodily fluid, which can be used in one or more rapid testing processes, and the subsequent volume(s) of bodily fluid, which can be used in testing that has a relatively high sensitivity to contamination (e.g., blood culture testing), as described above with reference to the systems 100, 200, and/or 300.

FIGS. 6A-6D are schematic illustrations of at least a portion of a fluid transfer and assay system 500, according to an embodiment. The fluid transfer and assay system 500 (also referred to herein as "system") can include at least a fluid transfer device 505 and a rapid diagnostic testing device 570. Portions and/or aspects of the fluid transfer device 505 and/or the rapid diagnostic testing device 570 can be similar to and/or substantially the same as the fluid transfer devices 105, 205, 305, and/or 405, and/or the rapid diagnostic testing devices 170 (and/or the LFA 170A), 270, 370, and/or 470, respectively, described in detail above. Accordingly, such portions and/or aspects are not described in further detail herein.

The fluid transfer device 505 (also referred to herein as "transfer device") can be any suitable shape, size, and/or configuration. In some implementations, the transfer device 505 can be configured to withdraw bodily fluid (e.g., blood) from a patient and into and/or through the transfer device 505. In addition, the transfer device 505 can be configured to transfer at least some of the withdrawn bodily fluid to one or more other devices, reservoirs, containers, vials, machines, tests, assays, etc., such as the rapid diagnostic testing device 570 and/or one or more fluid collection devices (not shown in FIGS. 6A-6D). The transfer device 505 and/or aspects or portions thereof can be substantially similar to any of the transfer devices 105, 205, 305, and/or 405 described in detail above. Thus, the transfer device 505 is not described in further detail herein.

The rapid diagnostic testing device 570 (also referred to herein as "rapid testing device" or simply "testing device") can be any suitable testing device. In some implementations, the testing device 570 and/or aspects or portions thereof can be substantially similar to the rapid testing devices 170 (and/or the LFA 170A), 270, 370, and/or 470 described in detail above. Accordingly, the rapid testing device 570 and/or aspects or portions thereof is/are not described in further detail herein.

Figure 6D:
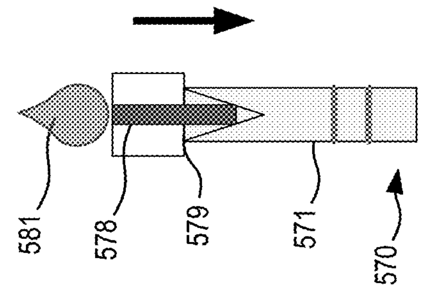
FIGS. 6A-6D are schematic illustrations of at least a portion of a fluid transfer and assay system in a first, a second, a third, and a fourth state, respectively, according to an embodiment.
Figure 6C:
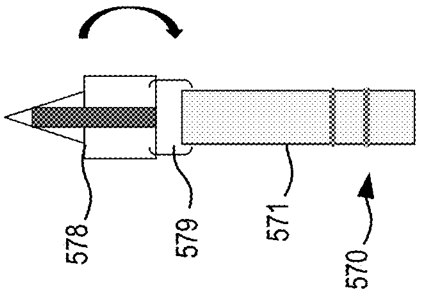
Figure 6B:
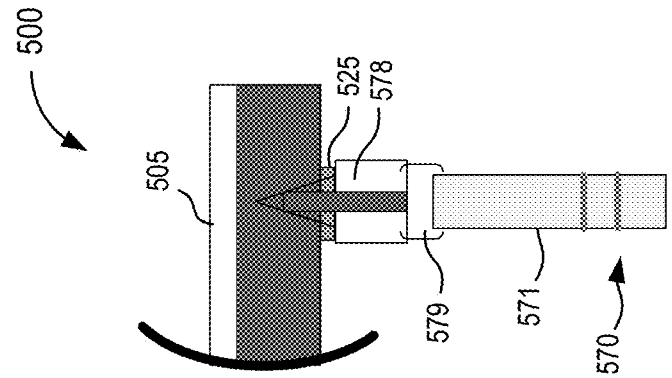
Figure 6A:
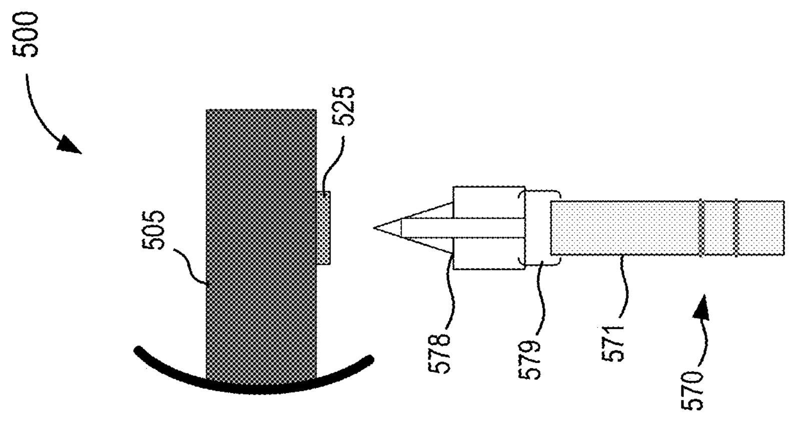

In the embodiment shown in FIGS. 6A-6D, the rapid testing device 570 can be an LFA or the like, as described in detail above with reference to the LFA 170A shown in FIG. 2. The rapid testing device 570 includes a substrate 571 having any suitable configuration of capillary beds or the like, as described in detail above. In addition, the rapid testing device 570 includes a coupling member 578 that can be coupled to the substrate 571 via an attachment mechanism 579. The coupling member 578 can be any suitable coupling member configured to establish fluid communication with an inner volume of the transfer device 505 in response to the rapid testing device 570 being coupled thereto. For example, as shown in FIGS. 6A and 6B, the rapid testing device 570 and/or the coupling member 578 thereof can be configured to couple to the transfer device 505 via a port 525 (e.g., any suitable port, vent, coupler, opening, valve, junction, etc.). In some embodiments, the coupling member 578 can be, for example, a puncture member, needle, tube, and/or the like that can puncture and/or otherwise advance through the port 525. In some embodiments, the coupling member 578 can be a capillary member or the like configured to transfer fluid via capillary action. In some embodiments, the port 525 can be self-healing allowing the port 525 to seal once the coupling portion 578 of the rapid testing device 570 is removed therefrom. In some embodiments, the port 525 and/or at least a portion of thereof can include and/or can form a vent similar to the vent 424.

The attachment mechanism 579 can be any suitable member, mechanism, device, etc. configured to attach the coupling member 578 to the substrate 571. In some embodiments, the attachment mechanism 579 can be configured to transition between two or more states or configuration to selectively place the coupling member 578 in fluid communication with a portion of the substrate 571 (e.g., a sample portion, element, and/or capillary bed). More particularly, the attachment mechanism 579 can be configured to transition between a first state and/or configuration (FIGS. 6A-6C) to a second state and/or configuration (FIG. 6D).

When in the first state, the rapid testing device 570 can be coupled to the transfer device 505 and the coupling portion 578 can establish fluid communication with the inner volume of the transfer device 505 (e.g., via the port 525). As shown in FIG. 6B, the coupling member 578 can receive at least portion of the volume of bodily fluid disposed in the transfer device 505 (e.g., via capillary action, a pressure differential, and/or any other fluid transfer modality). As shown in FIGS. 6C and 6D, once the coupling member 578 has received a desired volume of bodily fluid, the rapid testing device 570 can be decoupled from the transfer device 505 and the attachment mechanism 579 can be transitioned from its first state to its second state.

For example, in some embodiments, the attachment mechanism 579 can be a living hinge or the like that can be bent, folder, deformed, and/or otherwise reconfigured. When the attachment mechanism 579 is in the second state, the coupling member 578 can be in fluid communication with the portion of the substrate 571 (e.g., a sample portion, element, and/or capillary bed), as shown in FIG. 6D. Thus, the volume of bodily fluid contained in the coupling member 578 can be transferred to the portion of the substrate 571. In addition, in some implementations, when the attachment mechanism 579 is in the second state, a buffer 581 and/or any other suitable solution can be transferred to the substrate

571. The buffer 581 can be transferred to the substrate 571 via the coupling member 578, any suitable portion of the attachment mechanism 579, and/or any other suitable portion of the rapid testing device 570. As such, the buffer 581 can mix with the volume of bodily fluid and the mixture can flow along the substrate 571 for testing, as described in detail above. In some implementations, the rapid testing device 570 can be configured to test for the presence of lactate and/or PCT, which can be indicative of a patient condition such as sepsis. Moreover, once the test or assay is complete, the rapid testing device 570 can be configured to output a test result, which can be detected and/or assessed by a human and/or one or more electronic devices, as described in detail above with reference to the rapid testing devices 170, 270, 370, and/or 470.

FIGS. 7A-7D are schematic illustrations a fluid transfer and assay system 600, according to an embodiment. The fluid transfer and assay system 600 (also referred to herein as "system") can include at least a fluid transfer device 605 and a rapid diagnostic testing device 670. Portions and/or aspects of the fluid transfer device 605 and/or the rapid diagnostic testing device 670 can be similar to and/or substantially the same as the fluid transfer devices 105, 205, 305, 405, and/or 505, and/or the rapid diagnostic testing devices 170 (and/or the LFA 170A), 270, 370, 470, and/or 570, respectively, described in detail above. Accordingly, such portions and/or aspects are not described in further detail herein.

The fluid transfer device 605 (also referred to herein as "transfer device") can be any suitable shape, size, and/or configuration. In some implementations, the transfer device 605 can be configured to withdraw bodily fluid (e.g., blood) from a patient and into and/or through the transfer device 605. In addition, the transfer device 605 can be configured to transfer at least some of the withdrawn bodily fluid to one or more other devices, reservoirs, containers, vials, machines, tests, assays, etc., such as the rapid diagnostic testing device 670 and/or one or more fluid collection devices (not shown in FIGS. 7A-7D).

The transfer device 605 includes at least a housing 610 and an actuator 650. The housing 610 of the device 605 can be any suitable shape, size, and/or configuration. For example, in some embodiments, the housing 610 can be similar to and/or the substantially the same as the housings 210, 310, and/or 410 described above. Specifically, the housing 610 has and/or forms an inlet 612 and an outlet 613 and can define a fluid flow path 615 therebetween. The inlet 612 can be any suitable inlet or port and can be configured to establish fluid communication between the housing 610 to a bodily fluid source (e.g., a patient). The outlet 613 can be any suitable outlet or port and can be configured to establish fluid communication between the housing 610 and a fluid collection device (not shown in FIGS. 7A-7D), such as any of those described in detail above. The fluid flow path 615 defined by the housing 610 extends between the inlet 612 and the outlet 613 and can selectively establish fluid communication therebetween, as described in further detail herein.

As described above with reference to the housing 410, the housing 610 shown in FIGS. 7A-7D includes, forms, and/or couples to a sequestration chamber 630 configured to be selectively placed in fluid communication with the fluid flow path and/or at least the inlet 612. In addition, the sequestration chamber 630 includes, forms, and/or defines a sampling portion 635 and a port 625. The sequestration chamber 630 can have any suitable shape, size, and/or configuration. For example, in some embodiments, the sequestration chamber 630 and/or at least a portion thereof can be substantially similar in at least form and/or function to the sequestration chambers 330 and/or 430 described in detail above. Thus, portions and/or aspects of the sequestration chamber 630 are not described in further detail herein.

The port 625 is coupled to the housing 610 and/or the sequestration chamber 630 and is in fluid communication with an internal volume of the sequestration chamber 630. More specifically, as shown in FIGS. 7A-7D, the port 625 is included in and/or coupled to the housing 610 and in fluid communication with the sampling portion 635 of the sequestration chamber 630. In some embodiments, the port 625 and/or at least a portion thereof can be configured to vent and/or otherwise allow a flow of air or gas out of the sequestration chamber 630 as the initial volume of bodily fluid is transferred into the sequestration chamber 630, as described in detail above with reference to the vent 424. The sampling portion 635 of the sequestration chamber 630 can be placed in fluid communication with the rapid diagnostic testing device 670 to transfer a part of the initial volume of bodily fluid disposed in the sampling portion 635 into the rapid diagnostic testing device 670. In the embodiment shown in FIGS. 7A-7D, for example, the rapid diagnostic testing device 670 can be placed in fluid communication with the sampling portion 635 via the port 625 and/or any other suitable port, as described above with reference to the port 525 shown in FIGS. 6A and 6B.

The actuator 650 of the device 605 can be any suitable shape, size, and/or configuration. In some embodiments, the actuator 650 and/or aspects or portions thereof can be similar to and/or substantially the same as the actuators 150, 250, 350, and/or 450 described in detail above. In some embodiments, the actuator 650 can be at least partially disposed within and/or partially formed by the housing 610. As described above, the actuator 650 can be configured to control, direct, and/or otherwise facilitate a selective flow of fluid through at least a portion of the housing 610 and/or at least a portion of the one or more fluid flow paths. The actuator 650 can be any suitable member(s) or device(s) configured to transition between any number of states (e.g., two, three, four, or more) and in any suitable manner (e.g., user actuation, automatic actuation, mechanical actuation, electronic actuation, chemical actuation, and/or the like).

More particularly, in the embodiment shown in FIGS. 7A-7D, the actuator 650 includes a first member 651 and a second member 660. The first member 651 of the actuator 650 can be any suitable shape, size, and/or configuration. The first member 651 can be a plunger or the like having at least one seal 652 (e.g., disposed at an end portion of the first member 651). In some embodiments, the end portion of the first member 651 can, for example, separate and/or at least partially define the sampling portion 635 of the sequestration chamber 630. For example, the sampling portion 635 of the sequestration chamber 630 can be disposed on one side of the end portion of the first member 651 while the remaining portion of the sequestration chamber 630 is disposed on the opposite side of the end portion of the first member 651. Moreover, the arrangement of the seal 652 can be such that the seal 652 engages and/or contacts an inner surface of the housing 610 to form and/or define a substantially fluid tight seal therebetween. The first member 651 also includes one or more valves, ports, openings, channels, selectively permeable members, and/or the like (referred to herein as "valve 653") configured to establish selective fluid communication between the sampling portion 635 of the sequestration chamber 635 and the remaining portions of the sequestration chamber 630, as described in further detail herein.

The second member 660 of the actuator 650 can be any suitable shape, size, and/or configuration. For example, in the embodiment shown in FIGS. 7A-7D, the second member 660 can be disposed about and/or on at least a portion of the first member 651. The second member 660 includes a set of seals 661. More particularly, the second member 660 can include a set of three seals. As shown, the second member 660 can have a first end portion and a second end portion opposite the first end portion. The first end portion of the second member 660 includes an outer seal 661 configured to engage and/or contact an inner surface of the housing 610 to define a substantially fluid tight seal therebetween. In addition, the first end portion of the second member 660 includes an inner seal 661 configured to engage and/or contact a portion of the first member 651 to define a substantially fluid tight seal therebetween. The second end portion of the second member 660 includes an outer seal 661 configured engage and/or contact an inner surface of the housing to define a substantially fluid tight seal therebetween.

As shown in FIGS. 7A-7D, the arrangement of the first member 651 and the second member 660 of the actuator is such that a portion of the sequestration chamber 630 (e.g., the portion other than the sampling portion 635) is disposed and/or defined between, for example, the end portion of the first member 651 and the first end portion of the second member 660. In addition, the second member 660 is configured to at least partially define the fluid flow path 615 between the first end portion and the second end portion of the second member 660. Thus, the first end portion of the second member 660 and the seals 661 included in the first end portion, sequester and/or fluidically isolate the sequestration chamber 630 from the fluid flow path 615.

Figure 7A:
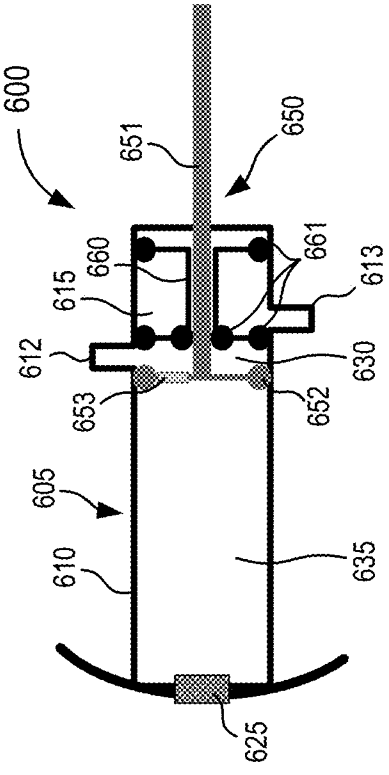
FIGS. 7A-7D are schematic illustrations of at least a portion of a fluid transfer and assay system in a first, a second, a third, and a fourth state, respectively, according to an embodiment.
Figure 7B:
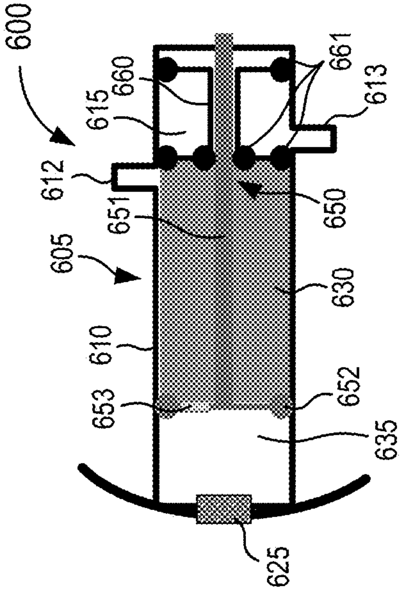
Figure 7C:
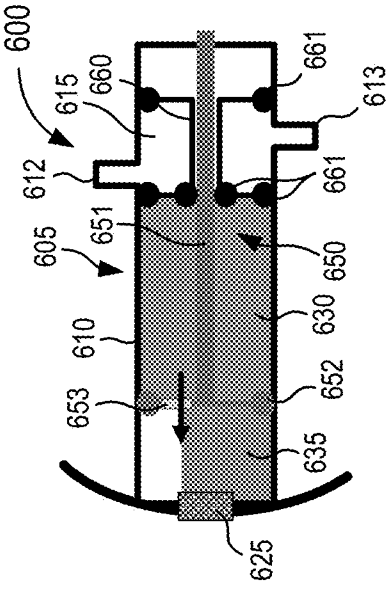
Figure 7D:
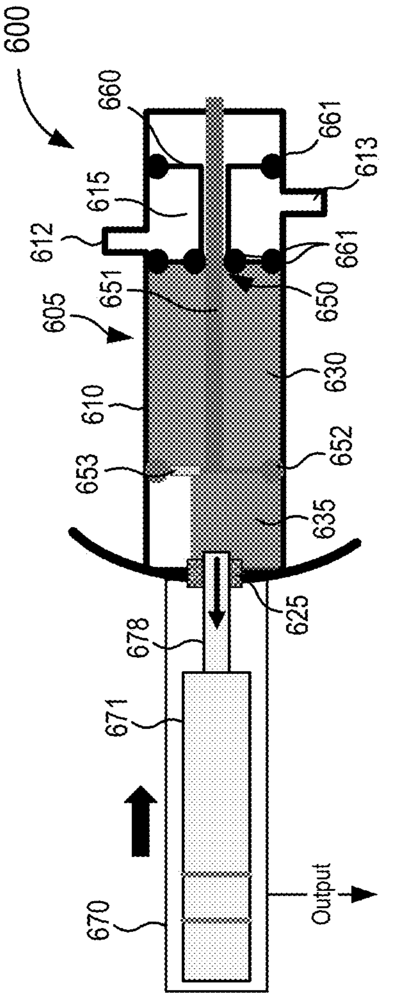

The actuator 650 is configured to transition between at least a first state, a second state, and a third state. As shown in FIGS. 7A-7D, the end portion of first member 651 and the seal 652 included therein are disposed on and maintained on a first side of the inlet 612 and a first side of the outlet 613, regardless of the state of the actuator 650. Similarly, the second end portion of the second member 660 and the seal member 661 included therein are disposed on and maintained on a second side of the inlet 612 (opposite the first side) and a second side of the outlet 613 (opposite the first side), regardless of the state of the actuator 650. The first end portion of the second member 660 and the seal members 661 disposed therein, however, are configured to be (i) disposed on the second side of the inlet 612 and the first side of the outlet 613 when the actuator 650 is in the first state and the second state (FIGS. 7A and 7B) and (ii) disposed on the first side of the inlet 612 and the first side of the outlet 613 when the actuator 650 is in the third state (FIGS. 7C and 7D). Thus, the arrangement of the actuator 650 is such that transitioning the actuator 650 can selectively direct and/or divert a flow of fluid between (i) the inlet 612 and the sequestration chamber 630 and (ii) the inlet 612 and the outlet 613 via the fluid flow path 615, as described in further detail herein.

The rapid diagnostic testing device 670 (also referred to herein as "rapid testing device" or simply "testing device") can be any suitable testing device. For example, the rapid testing device 670 can be an LFA or the like, as described in detail above with reference to the LFA 170A shown in FIG. 2. In some implementations, the testing device 670 and/or aspects or portions thereof can be substantially similar to the rapid testing devices 170, 270, 370, and/or 470 described in detail above. Accordingly, the rapid testing device 670 and/or aspects or portions thereof is/are not described in further detail herein.

As shown in FIG. 7D, the rapid testing device 670 can be configured to engage or couple to the housing 610 via the port 625. In some embodiments, for example, the port 625 can be a valve, coupler, and/or any suitable reconfigurable member or device configured to (i) vent air or gas from the sequestration chamber 630, as described above with reference to the vent 424, and (ii) receive a portion of the rapid testing device 670 to place the rapid testing device 670 in fluid communication with the sampling portion 635 of the sequestration chamber 630. For example, the rapid testing device 670 can include a coupling member 678 that can establish fluid communication with the sampling portion 635 of the sequestration chamber 630 when the rapid testing device 670 is coupled thereto. In some embodiments, the coupling member 678 can be, for example, a puncture member, needle, tube, capillary, and/or the like that can puncture and/or otherwise advance through the port 625. In some embodiments, the coupling member 678 can be substantially similar to the coupling member 578 described above with reference to FIGS. 6A-6D. In some embodiments, the port 625 can be self-healing allowing the port 625 to seal once the coupling portion 678 of the testing device 670 is removed therefrom. As shown in FIG. 7D, the coupling portion 678 of the testing device 670 can be coupled to a substrate 671 of the testing device 670 (e.g., coupled directly to the substrate 671 and/or coupled via an attachment mechanism such as the attachment mechanism 579). In this manner, the coupling portion 678 can transfer a volume of bodily fluid from the sampling portion 635 of the sequestration chamber 630 into the testing device 670. In response, the testing device 670 can use the volume of bodily fluid to perform one or more tests, assays, and/or diagnostic procedures.

The system 600 can be used to procure one or more volumes of bodily fluid from a patient, which can be used in one or more tests, assays, and/or diagnostic procedures. As described above, for example, the inlet 612 can be placed in fluid communication with a bodily fluid source. The actuator 650 can be in a first state when the inlet 612 is placed in fluid communication with the bodily fluid source (e.g., the portion of the patient), thereby establishing fluid communication between the inlet 612 and the sequestration chamber 630 and sequestering the outlet 613 from the inlet 612, as shown in FIG. 7A. Moreover, when the actuator 650 is in the first state, the end portion of the first member 651 can be near or adjacent to the first side of the inlet 612 and the first end portion of the second member 660 can be near or adjacent to the second side of the inlet 612. In this manner, the portion of the sequestration chamber 630 defined between the first member 651 and the second member 660 can have a first volume.

In some instances, once the inlet 612 is placed in fluid communication with the bodily fluid source, the actuator 650 can be transitioned from its first state to its second state. For example, as shown in FIG. 7B, the first member 651 can be transitioned or moved relative to the inlet 612 and the second member 660, which in turn, increases a volume of the portion of the sequestration chamber 630 disposed between the first member 651 and the second member 660. In addition, the transitioning and/or movement of the first member 651 can reduce a volume of the sampling portion 635 of the sequestration chamber 630, and the arrangement of the port 625 can be such that air or gas contained in the sampling portion 635 can be allowed to escape and/or flow out of the sampling portion 635. The end portion of the first member 651 can be configured to limit and/or substantially prevent a flow of air from the sampling portion 635 of the sequestration chamber 630 into the remaining portion of the sequestration chamber 630 such that the increase in the volume within the remaining portion of the sequestration chamber 630 results in a negative pressure differential operative in drawing the initial volume of bodily fluid from the bodily fluid source, through the inlet 612, and into the sequestration chamber 630, as shown in FIG. 7B.

The initial volume of bodily fluid can be any suitable volume of bodily fluid, such as any of the volumes or amounts described above. In some implementations, once the initial volume of bodily fluid is transferred into the sequestration chamber 630, the flow of bodily fluid can stop and/or a pressure differential can be substantially equalized that can slow or stop the flow of bodily fluid. In such implementations, the actuator 650 can then be transitioned from its second state to its third state. In other implementations, the transitioning of the actuator 650 through the three states can be a substantially continuous transition. In such implementations, the initial volume of bodily fluid can be a volume of bodily fluid that is transferred into the sequestration chamber 630 as the actuator 650 is transitioned from its first state to its second state, and continuing to transition the actuator 650 from its second state to its third state can be operable in stopping the flow into the sequestration chamber 630.

The actuator 650 can be transitioned from its second state to its third state when the initial volume of bodily fluid is contained in the sequestration 630. As shown in FIG. 7C, transitioning the actuator 650 to the third state can include transitioning and/or moving the second member 660 relative to the inlet 612 and the first member 651 of the actuator 650. The transitioning and/or moving of the second member 660 transitions and/or moves the first end portion of the second member from the second side of the inlet 612 to the first side of the inlet 612, thereby sequestering and/or fluidically isolating the sequestration chamber 630 from the inlet 612. Moreover, the transitioning and/or moving of the second member 660 relative to the first member 651 can decrease a volume of the portion of the sequestration chamber 630 disposed therebetween. In some implementations, the decrease in the volume of the portion of the sequestration chamber 630 results in an increase in pressure that can be operable in transitioning the valve 653 from a closed state to an open state, thereby allowing at least some of the initial volume of bodily fluid to be transferred into the sampling portion 635 of the sequestration chamber 630, as shown in FIG. 7C.

As shown in FIG. 7D, the rapid testing device 670 can be coupled to the housing 610 and/or can otherwise be placed in fluid communication with the sampling portion 635 of the sequestration chamber 630 (e.g., via the coupling member 678). Accordingly, at least a portion of the bodily fluid can be transferred from the sampling portion 635 of the sequestration chamber 630 and into the rapid testing device 670. In some implementations, the transferring of the portion of the initial volume can be automatic. In other implementations, the transferring of the portion of the initial volume can be in response to one or more user inputs and/or the like (e.g., via the actuator 650 and/or any other suitable actuation mechanism or the like not shown in FIGS. 7A-7D). In some embodiments, transferring the portion of the initial volume of bodily fluid into the rapid testing device 670 can initiate a test and/or assay of or on the portion of the initial volume of bodily fluid, as described in detail above with reference to the rapid testing device 270. Although not shown in FIGS. 7A-7D, in some instances, the system 600, the transfer device 605, and/or the rapid testing device 670 can be configured to provide a buffer (or any other suitable solution) that can be mixed with the portion of the initial volume of bodily fluid. The rapid testing device 670 can be configured to perform any suitable test and/or assay. For example, the rapid testing device 670 can be an LFA configured to test for the presence of lactate and/or PCT, as described in detail above. Moreover, once the test or assay is complete, the rapid testing device 670 can be configured to output a test result, which can be detected and/or assessed by a human and/or one or more electronic devices, as described in detail above with reference to the rapid testing devices 170, 270, 370, and/or 470.

As described above, transitioning the actuator 650 from its second state to its third state can sequester, isolate, separate, and/or retain the initial volume of the bodily fluid in the sequestration chamber 630 and/or the rapid testing device 670, which in turn, can also sequester contaminants in the initial volume. Moreover, the arrangement of the rapid testing device 670 can be such that the tests and/or assays performed by the rapid testing device 670 are not susceptible to such contamination, which means that the accuracy of the test results output by the rapid testing device 670 is not affected by such contamination, as described in detail above.

As shown in FIGS. 7C and 7D, transitioning the actuator 650 from its second state to its third state establishes fluid communication between the inlet 612 and the outlet 613 via the fluid flow path 615 disposed between the first end portion and the second end portion of the second member 660 of the actuator 650. More particularly, when the actuator 650 is in its third state, the first end portion of the second member 660 is disposed on the first side of the inlet 612 and the second end portion of the second member 660 is disposed on the second side of the outlet 613. In other words, both the inlet 612 and the outlet 613 are disposed between the first end portion and the second end portion of the second member 660. Thus, the fluid flow path 615 can establish fluid communication between the inlet 612 and the outlet 613 when the actuator 650 is in the third state.

In some implementations, the outlet 613 can be placed in fluid communication with a fluid collection device (not shown in FIGS. 7A-7D) prior to or after the actuator 650 is placed in its third state. As described in detail above, the fluid collection device can define and/or can be configured to generate a negative pressure and/or suction force that can be operable to draw bodily fluid into the fluid collection device. Thus, in response to the negative pressure and/or suction force, one or more subsequent volume(s) of the bodily fluid can flow from the inlet 612, through the fluid flow path 615, through the outlet 613, and into the fluid collection device. As described above, sequestering the initial volume of bodily fluid in the sequestration chamber 630 prior to collecting or procuring one or more subsequent volumes of bodily fluid reduces and/or substantially eliminates an amount of contaminants in the one or more subsequent volumes. Accordingly, the system 600 can be configured to procure the initial volume of bodily fluid, which can be used in rapid testing that has relatively low sensitivity to contamination, and the subsequent volume(s) of bodily fluid, which can be used in testing that has a relatively high sensitivity to contamination, as described above with reference to the systems 100, 200, 300, and/or 400.

FIGS. 8 and 9A-9D illustrate a fluid transfer and assay system 700, according to an embodiment. The fluid transfer and assay system 700 (also referred to herein as "system")

can include at least a fluid transfer device 705 and a rapid diagnostic testing device 770. Portions and/or aspects of the fluid transfer device 705 and/or the rapid diagnostic testing device 770 can be similar to and/or substantially the same as the fluid transfer devices 105, 205, 305, 405, 505, and/or 605, and/or the rapid diagnostic testing devices 170 (and/or the LFA 170A), 270, 370, 470, 570, and/or 670, respectively, described in detail above. Accordingly, such portions and/or aspects are not described in further detail herein.

The fluid transfer device 705 (also referred to herein as "transfer device") can be any suitable shape, size, and/or configuration. In some implementations, the transfer device 705 can be configured to withdraw bodily fluid (e.g., blood) from a patient and into and/or through the transfer device 705. In addition, the transfer device 705 can be configured to transfer at least some of the withdrawn bodily fluid to one or more other devices, reservoirs, containers, vials, machines, tests, assays, etc., such as the rapid diagnostic testing device 770 and/or one or more fluid collection devices (not shown in FIGS. 8 and 9A-9D).

The transfer device 705 includes at least a housing 710 and an actuator 750. The housing 710 of the device 705 can be any suitable shape, size, and/or configuration. For example, in some embodiments, the housing 710 can be similar to and/or the substantially the same as at least the housing 610 described above. Specifically, the housing 710 has and/or forms an inlet 712 and an outlet 713 and can define a fluid flow path 715 therebetween. The inlet 712 can be any suitable inlet or port and can be configured to establish fluid communication between the housing 710 to a bodily fluid source (e.g., a patient). The outlet 713 can be any suitable outlet or port and can be configured to establish fluid communication between the housing 710 and a fluid collection device (not shown in FIGS. 8-9D), such as any of those described in detail above. The fluid flow path 715 defined at least in part by the housing 710 extends between the inlet 712 and the outlet 713 and can selectively establish fluid communication therebetween, as described in further detail herein.

Figure 8:
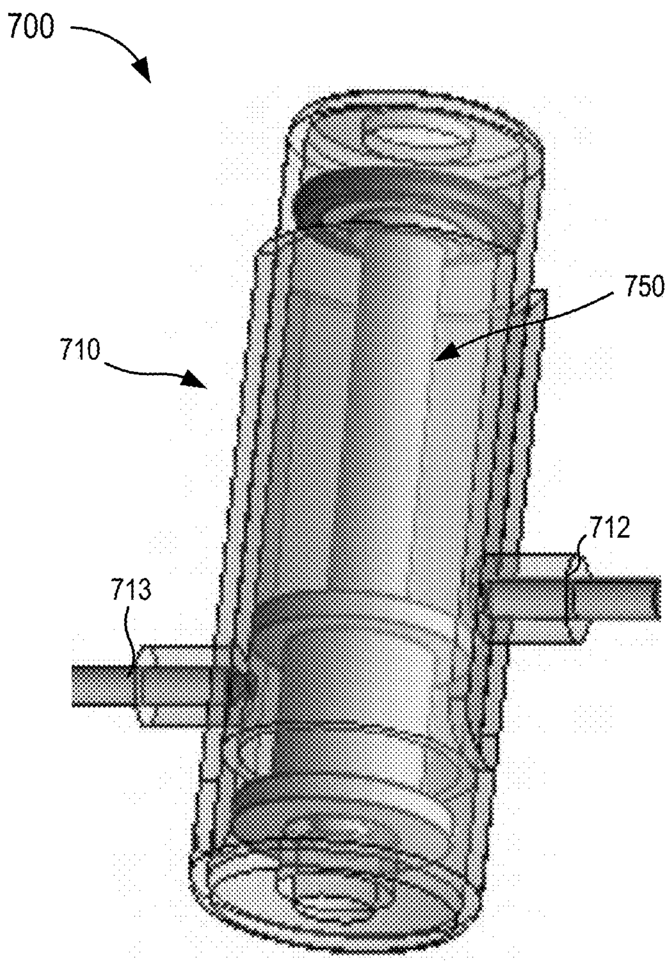
FIG. 8 is a perspective view of a fluid transfer and assay device (or system) according to an embodiment.
Figure 9B:
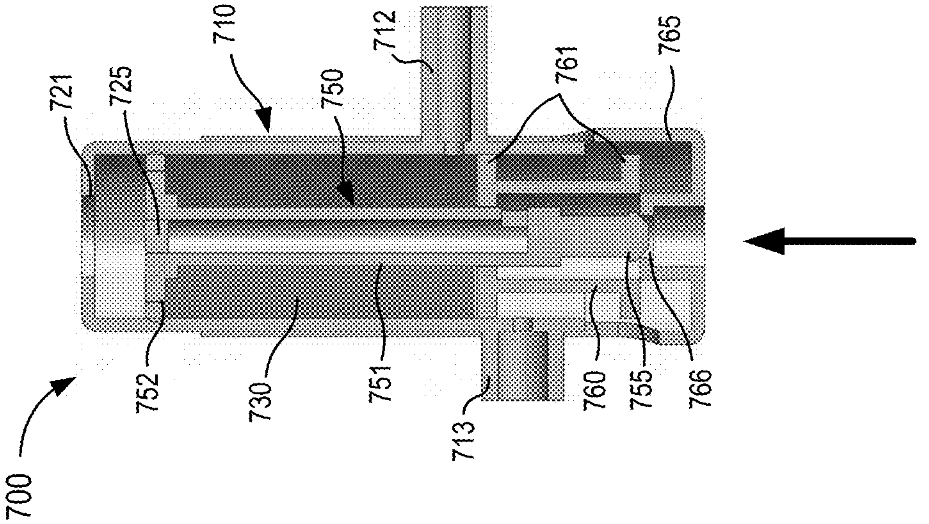
FIGS. 9A-9D are cross-sectional views of the fluid transfer and assay device (or system) of FIG. 12, shown in a first, a second, a third, and a fourth state, respectively.
Figure 9A:
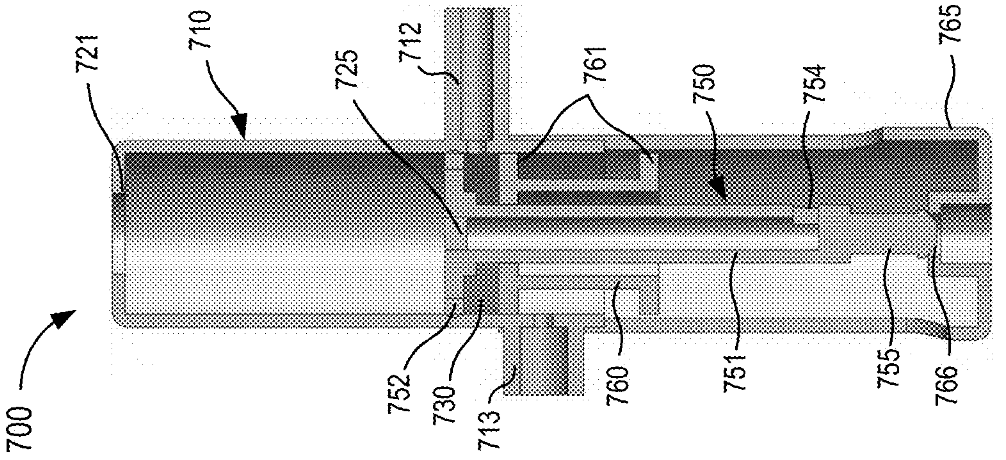
Figure 9D:
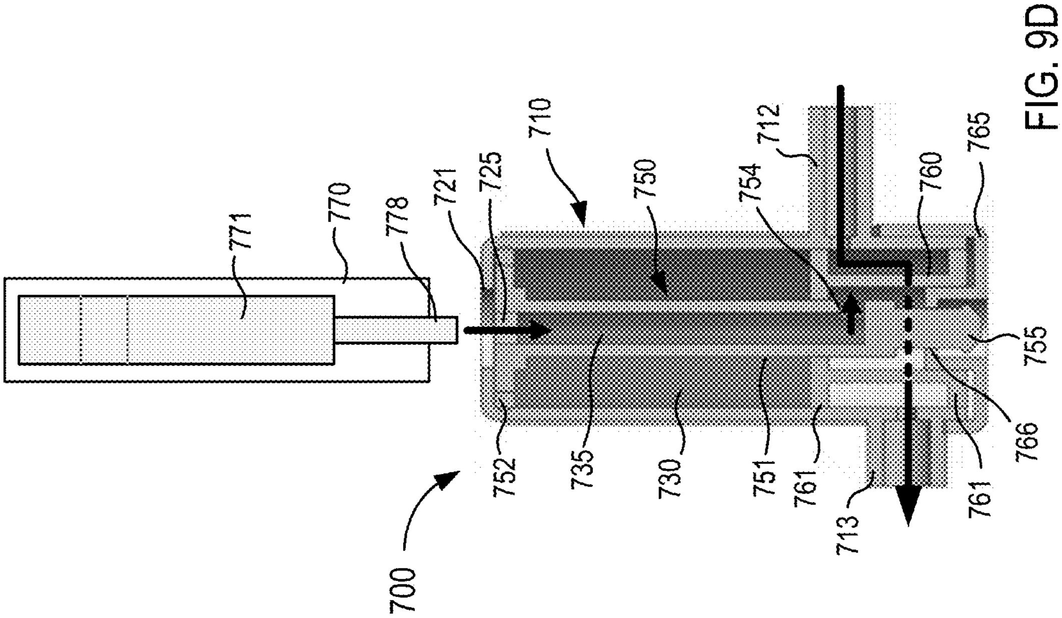

As described above with reference to at least the housing 610, the housing 710 shown in FIGS. 8-9D includes, forms, and/or couples to a sequestration chamber 730 configured to be selectively placed in fluid communication with the fluid flow path and/or at least the inlet 712. In addition, the housing defines an opening 721 and/or a port configured to receive a portion of the rapid diagnostic testing device 770, as described in further detail herein. The sequestration chamber 730 can have any suitable shape, size, and/or configuration. For example, in some embodiments, the sequestration chamber 730 and/or at least a portion thereof can be substantially similar in at least form and/or function to the sequestration chambers 330, 430, and/or 630 described in detail above. Thus, portions and/or aspects of the sequestration chamber 730 are not described in further detail herein.

The actuator 750 of the device 705 can be any suitable shape, size, and/or configuration. In some embodiments, the actuator 750 and/or aspects or portions thereof can be similar to and/or substantially the same as the actuators 150, 250, 350, 450, and/or 650 described in detail above. In some embodiments, the actuator 750 can be at least partially disposed within and/or partially formed by the housing 710. As described above, the actuator 750 can be configured to control, direct, and/or otherwise facilitate a selective flow of fluid through at least a portion of the housing 710 and/or at least a portion of the one or more fluid flow paths. The actuator 750 can be any suitable member(s) or device(s) configured to transition between any number of states (e.g., two, three, four, or more) and in any suitable manner (e.g., user actuation, automatic actuation, mechanical actuation, electronic actuation, chemical actuation, and/or the like).

More particularly, as shown in FIGS. 9A-9D, the actuator 750 includes a first member 751, a second member 760, and a third member 765. The first member 751 of the actuator 750 can be any suitable shape, size, and/or configuration. For example, the first member 751 can be similar in at least form and/or function to the first member 651 of the actuator 650, described in detail above. The first member 751 includes at least one seal 752 disposed at a first end portion of the first member 751. The arrangement of the seal 752 can be such that the seal 752 engages and/or contacts an inner surface of the housing 710 to form and/or define a substantially fluid tight seal therebetween.

The first end portion of the first member 751 also includes a port 725 that is in fluid communication with a sampling channel 735. In some embodiments, for example, the port 725 can be a valve, coupler, and/or any suitable reconfigurable member or device configured to (i) vent and/or allow a flow of air or gas out of the sampling channel 735 and (ii) receive a portion of the rapid testing device 770 to place the rapid testing device 770 in fluid communication with the sampling channel 735, as described above with reference to the port 625. The sampling channel 735 is disposed in and/or defined by the first member 751. For example, in some embodiments, the first member 751 can have a hollow elongate portion that defines the sampling channel 735. Moreover, such a portion of the first member 751 can define and/or can have an opening, port, valve, selectively permeable member, and/or the like configured to place the sampling channel 735 in selective fluid communication with the sequestration chamber 730. In some embodiments, while the sampling channel 735 is included in and/or defined by the first member 751 of the actuator 750, the sampling channel 735 can be similar in at least form and/or function to the sampling portion 635 of the sequestration chamber 630, described above with reference to FIGS. 7A-7D.

As shown in FIGS. 9A-9D, the first member 751 also includes an engagement member 755 disposed at or on a second end portion of the first member 751, opposite the first end portion. The engagement member 755 can be any suitable shape, size, and/or configuration. For example, in some embodiments, the engagement member 755 can be a protrusion, tab, button, knob, and/or any other suitable engagement member. The engagement member 755 is configured to selectively engage a portion of the third member 765 of the actuator 750 to direct and/or at least partially control a relative movement between the first member 751, the second member 760, and/or the third member 765, as described in further detail herein.

The second member 760 of the actuator 750 can be any suitable shape, size, and/or configuration. As shown in FIGS. 9A-9D, the second member 760 can be disposed about and/or on at least a portion of the first member 751. The second member 760 includes a set of seals 761. As shown, the second member 760 can includes a first end portion having an inner seal 761 and an outer seal 761, and a second end portion opposite the first end portion having an outer seal 761. In this manner, the second member 760 can be similar to and/or substantially the same as the second member 660 of the actuator 650. Accordingly, the second member 760 and/or aspects or portions thereof are not described in further detail herein.

The third member 765 can be any suitable shape, size, and/or configuration. In some embodiments, the third member 765 can be included in and/or can form a portion of the housing 710 and/or an exterior portion of the transfer device 705. For example, as shown in FIGS. 9A-9D, at least a portion of the housing 710, first member 751, and second member 760 can be disposed within a portion of the third member 765. More particularly, the third member 765 can be a substantially hollow cylinder or the like having an open end and a substantially closed end. The substantially closed end includes and/or defines a detent, recess, opening, and/or engagement structure (referred to herein as "engagement structure 766"). The engagement structure 766 can be in contact with and/or can otherwise selectively engage the engagement member 755 of the first member 751. For example, as described in further detail herein, the engagement member 755 can be configured to engage and/or contact the engagement structure 766, which in turn, can result in the first member 751 and the third member 765 being moved collectively and/or concurrently as the actuator 750 is transitioned between two or more states or configurations. Moreover, a portion of the transitioning of the actuator 750 can result in the engagement member 755 disengaging and/or moving relative to the engagement structure 766, which in turn, can result in the first member 751 being moved relative to the third member 765 (or vice versa), as described in further detail herein.

As shown in FIGS. 9A-9D, the arrangement of the first member 751 and the second member 760 of the actuator is such that the sequestration chamber 730 is disposed and/or defined between, for example, the first end portion of the first member 751 and the first end portion of the second member 760. In addition, the second member 760 is configured to at least partially define the fluid flow path 715 between the first end portion and the second end portion of the second member 760. Thus, the first end portion of the second member 760 and the seals 761 included in the first end portion, sequester and/or fluidically isolate the sequestration chamber 730 from the fluid flow path 715.

The actuator 750 is configured to transition between at least a first state, a second state, a third state, and a fourth state. As shown in FIGS. 9A-9D, the first end portion of first member 751 and the seal 752 included therein are disposed on and maintained on a first side of the inlet 712 and a first side of the outlet 713, regardless of the state of the actuator 750. Similarly, the second end portion of the second member 760 and the seal member 761 included therein are disposed on and maintained on a second side of the inlet 712 (opposite the first side) and a second side of the outlet 713 (opposite the first side), regardless of the state of the actuator 750. The first end portion of the second member 760 and the seal members 761 disposed therein, however, are configured to be (i) disposed on the second side of the inlet 712 and the first side of the outlet 713 when the actuator 750 is in the first state (FIG. 9A), the second state (FIG. 9B), and the third state (FIG. 9C), and (ii) disposed on the first side of the inlet 712 and the first side of the outlet 713 when the actuator 750 is in the fourth state (FIG. 9D). Thus, the arrangement of the actuator 750 is such that transitioning the actuator 750 can selectively direct and/or divert a flow of fluid between (i) the inlet 712 and the sequestration chamber 730 and (ii) the inlet 712 and the outlet 713 via the fluid flow path 715, as described in further detail herein.

The rapid diagnostic testing device 770 (also referred to herein as "rapid testing device" or simply "testing device") can be any suitable testing device. For example, the rapid testing device 770 can be an LFA or the like, as described in detail above with reference to the LFA 170A shown in FIG. 2. In some implementations, the testing device 770 and/or aspects or portions thereof can be substantially similar to the rapid testing devices 170, 270, 370, 470, 570, and/or 670 described in detail above. Accordingly, the rapid testing device 770 and/or aspects or portions thereof is/are not described in further detail herein.

As shown in FIG. 9D, the rapid testing device 770 includes a coupling member 778 that is coupled to and/or at least in fluid communication with a substrate 771 of the testing device 770 (e.g., coupled directly to the substrate 771 and/or coupled via an attachment mechanism such as the attachment mechanism 579). The coupling member 778 can be at least partially inserted through the opening 721 of the housing 710 to establish fluid communication with the sampling channel 735 when the rapid testing device 770 is coupled the transfer device 705. For example, the coupling member 778 can be a puncture member, needle, tube, capillary, and/or the like that can puncture and/or otherwise advance through the port 725. In some embodiments, the substrate 771 and the coupling member 778 can be substantially similar to the substrates 571 and/or 671, and the coupling members 578 and/or 678 described in detail above. Thus, the substrate 771 and the coupling member 778 (and/or aspects or portions thereof) are not described in further detail herein.

The system 700 can be used to procure one or more volumes of bodily fluid from a patient, which can be used in one or more tests, assays, and/or diagnostic procedures. As described above, for example, the inlet 712 can be placed in fluid communication with a bodily fluid source. The actuator 750 can be in a first state when the inlet 712 is placed in fluid communication with the bodily fluid source (e.g., the portion of the patient), thereby establishing fluid communication between the inlet 712 and the sequestration chamber 730 and sequestering the outlet 713 from the inlet 712, as shown in FIG. 9A. Moreover, when the actuator 750 is in the first state, the first end portion of the first member 751 can be near or adjacent to the first side of the inlet 712 and the first end portion of the second member 760 can be near or adjacent to the second side of the inlet 712. In this manner, the sequestration chamber 730 defined between the first member 751 and the second member 760 can have a first volume.

In some instances, once the inlet 712 is placed in fluid communication with the bodily fluid source, the actuator 750 can be transitioned from its first state to its second state. For example, as shown in FIG. 9B, a user can exert a force on the third member 765 that can be operative to move the third member 765 relative to the housing 710. As described above, the arrangement of the engagement member 755 of the first member 751 and the engagement structure 766 of the third member 765 is such that movement of the third member 765 relative to the housing 710 results in a similar movement of the first member 751. The movement of the first member 751 is also relative to the second member 760 (e.g., the second member 760 is not yet moved), which in turn, increases a volume of the sequestration chamber 730 disposed between the first member 751 and the second member 760. In addition, the transitioning and/or movement of the first member 751 can reduce a volume within the housing 710 on a side of the first member 751 opposite the sequestration chamber 730, and the opening 721 can be such that air or gas contained therein can be allowed to escape and/or flow out of the sampling channel 735. Thus, the transitioning of the actuator 750 from its first state (FIG. 9A) to its second state (FIG. 9B) can result in a negative pressure differential being generated within the sequestration chamber operative in drawing the initial volume of bodily fluid from the bodily fluid source, through the inlet 712, and into the sequestration chamber 730, as described in detail above with reference to the sequestration chamber 630. Moreover, the initial volume of bodily fluid can be any suitable volume of bodily fluid, such as any of the volumes or amounts described above.

The actuator 750 can be transitioned from its second state (FIG. 9B) to its third state (FIG. 9C) when the initial volume of bodily fluid is contained in the sequestration 730. As described above with reference to the transfer device 605, the transitioning of the actuator 750 from the second state to the third state can be in response to the initial volume of bodily fluid being disposed in the sequestration chamber 730, in response to an equalization of one or more pressure differentials, in response to a given point in a continuous process of transitioning the actuator 750 from the first to the fourth state, and/or the like. In some instances, the transitioning can be automatic or in response to an applied force.

Figure 9C:
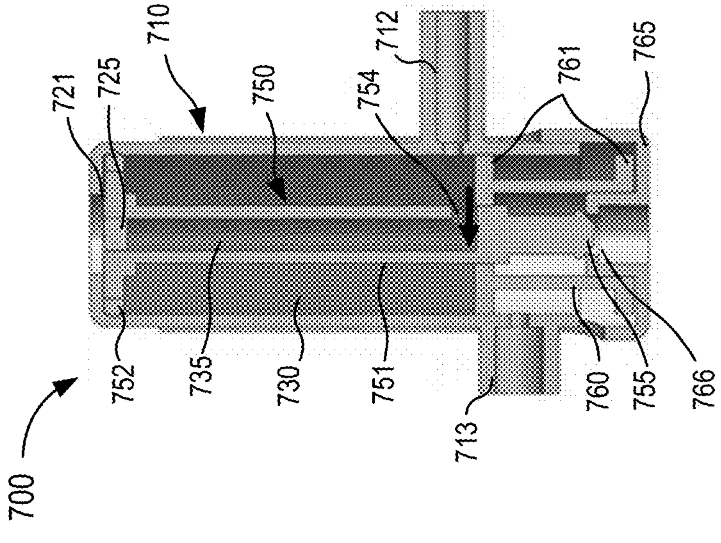
Figure 10:
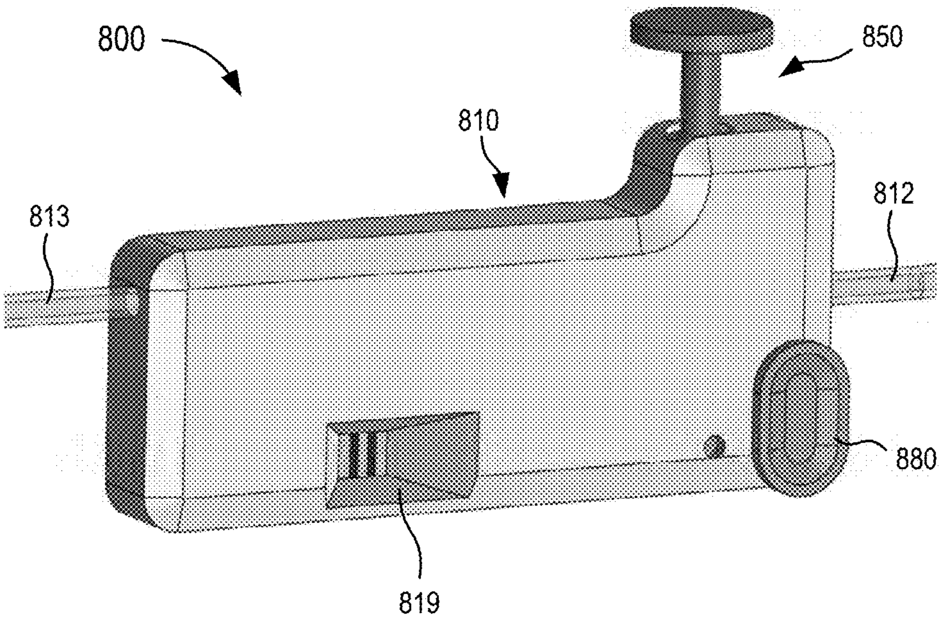
FIG. 10 is a perspective view of a fluid transfer and assay device (or system) according to an embodiment.

As shown in FIG. 9C, transitioning the actuator 750 to the third state can include transitioning and/or moving the first member 751 and the third member 765 an additional amount relative to the housing 710 and the second member 760. More specifically, when in the third state, the first member 751 can be placed in a position relative to the second member 760 such that an opening, port, valve, etc. (referred to herein as "opening 754") is placed in fluid communication with the sequestration chamber 730 and/or the inlet 712, as shown in FIG. 9C. In this manner, a volume of bodily fluid can be transferred into the sampling channel 735 defined by the first member 751. As described above, in some embodiments, the port 725 can be configured to vent the sampling channel 735 to facilitate the flow of bodily fluid into the sampling channel 735.

With a volume of bodily fluid contained in the sampling channel 735, the actuator 750 can be transitioned from its third state (FIG. 9C) to its fourth state (FIG. 9D). More specifically, in some implementations, the third member 765 and the second member 760 can be moved relative to the housing 710, while the first member 751 is maintained in a substantially fixed position relative to the housing 710. Said another way, the third member 765 and the second member 760 are moved together and relative to the first member 751.

As shown in FIG. 9D, the engagement member 755 is disengaged from and/or moved relative to the engagement surface 766 when the actuator 750 is transitioned to the fourth state. In some embodiments, the engagement member 755 and/or the engagement surface 766 can be sized and/or configured to maintain contact and/or engagement until a desired and/or predetermined force is exerted that is sufficient to overcome a force maintaining the engagement (e.g., a friction force, a force sufficient to elastically and/or plastically deform the engagement member 755 and/or the engagement surface 766, and/or any other suitable force). In other words, the third member 765 can be moved relative to the first member 751 when a force satisfies a criterion and/or is greater than a threshold amount of force.

The second member 760 of the actuator 750 is moved with and in the same direction as the third member 765 when the actuator 750 is transitioned to the fourth state. As shown in FIG. 9D, the transitioning and/or moving of the second member 760 transitions and/or moves the first end portion of the second member 760 from the second side of the inlet 712 to the first side of the inlet 712, thereby sequestering and/or fluidically isolating the sequestration chamber 730 from the inlet 712. Moreover, the transitioning and/or moving of the second member 760 relative to the first member 751 can place the opening 754 of the first member 751 on an opposite side of the inner seal 561 included in or on the first end portion of the second member 760, which in some instances, can allow the sampling channel 735 to be vented, as described in further detail herein.

As shown in FIG. 9D, the rapid testing device 770 can be coupled to the housing 710 and/or can otherwise be at least partially inserted into and/or through the opening 721 of the housing 710 to allow the coupling member 778 to establish fluid communication with the sampling channel 735 (e.g., via the port 725). Accordingly, at least a portion of the bodily fluid can be transferred from the sampling channel 735 and into the rapid testing device 770, as described in detail above with reference to the rapid testing devices 470, 570, and/or 670. In some embodiments, transferring the volume of bodily fluid from the sampling channel 735 into the rapid testing device 770 can initiate a test and/or assay of or on the portion of the initial volume of bodily fluid, as described in detail above with reference to the rapid testing device 270. Moreover, in some instances, venting the sampling channel 735 via the opening 754 can allow for a desired pressure differential within the sampling channel 735 that can facilitate the transfer of bodily fluid from the sampling channel 735 and into the rapid testing device 770. The rapid testing device 770 can be configured to perform any suitable test and/or assay (e.g., a test for the presence of lactate and/or PCT), such as any of those described in detail above. Moreover, once the test or assay is complete, the rapid testing device 770 can be configured to output a test result, which can be detected and/or assessed by a human and/or one or more electronic devices, as described in detail above with reference to the rapid testing devices 170, 270, 370, 470, 570, and/or 670.

As described above, transitioning the actuator 750 from its third state to its fourth state can sequester, isolate, separate, and/or retain the initial volume of the bodily fluid in the sequestration chamber 730 and/or the rapid testing device 770, which in turn, can also sequester contaminants in the initial volume. Moreover, the arrangement of the rapid testing device 770 can be such that the tests and/or assays performed by the rapid testing device 770 are not susceptible to such contamination, which means that the accuracy of the test results output by the rapid testing device 770 is not affected by such contamination, as described in detail above.

As shown in FIGS. 9D, transitioning the actuator 750 from its third state to its fourth state establishes fluid communication between the inlet 712 and the outlet 713 via the fluid flow path 715 disposed between the first end portion and the second end portion of the second member 760 of the actuator 750. When the actuator 750 is in its fourth state, the first end portion of the second member 760 is disposed on the first side of the inlet 712 and the second end portion of the second member 760 is disposed on the second side of the outlet 713, as described in detail above with reference to the actuator 650.

In some implementations, the outlet 713 can be placed in fluid communication with a fluid collection device (not shown in FIGS. 8-9D) prior to or after the actuator 750 is placed in its fourth state. As described in detail above, the fluid collection device can define and/or can be configured to generate a negative pressure and/or suction force that can be operable to draw bodily fluid into the fluid collection device. Thus, in response to the negative pressure and/or suction force, one or more subsequent volume(s) of the bodily fluid can flow from the inlet 712, through the fluid flow path 715, through the outlet 713, and into the fluid collection device. As described above, sequestering the initial volume of bodily fluid in the sequestration chamber

730 prior to collecting or procuring one or more subsequent volumes of bodily fluid reduces and/or substantially eliminates an amount of contaminants in the one or more subsequent volumes. Accordingly, the system 700 can be configured to procure the initial volume of bodily fluid, which can be used in rapid testing that has relatively low sensitivity to contamination, and the subsequent volume(s) of bodily fluid, which can be used in testing that has a relatively high sensitivity to contamination, as described above with reference to the systems 100, 200, 300, 400, and/or 600.

FIGS. 10, 11, and 12A-12D illustrate a fluid transfer and assay system 800, according to an embodiment. The fluid transfer and assay system 800 (also referred to herein as "system") can include at least a fluid transfer device 805 and a rapid diagnostic testing device 870. Portions and/or aspects of the fluid transfer device 805 and/or the rapid diagnostic testing device 870 can be similar to and/or substantially the same as the fluid transfer devices 105, 205, 305, 405, 505, 605, and/or 705, and/or the rapid diagnostic testing devices 170 (and/or the LFA 170A), 270, 370, 470, 570, 670, and/or 770, respectively, described in detail above. Accordingly, such portions and/or aspects are not described in further detail herein.

The fluid transfer device 805 (also referred to herein as "transfer device") can be any suitable shape, size, and/or configuration. In some implementations, the transfer device 805 can be configured to withdraw bodily fluid (e.g., blood) from a patient and into and/or through the transfer device 805. In addition, the transfer device 805 can be configured to transfer at least some of the withdrawn bodily fluid to one or more other devices, reservoirs, containers, vials, machines, tests, assays, etc., such as the rapid diagnostic testing device 870 and/or one or more fluid collection devices (not shown in FIGS. 10, 11, and 12A-12D).

Figure 11:
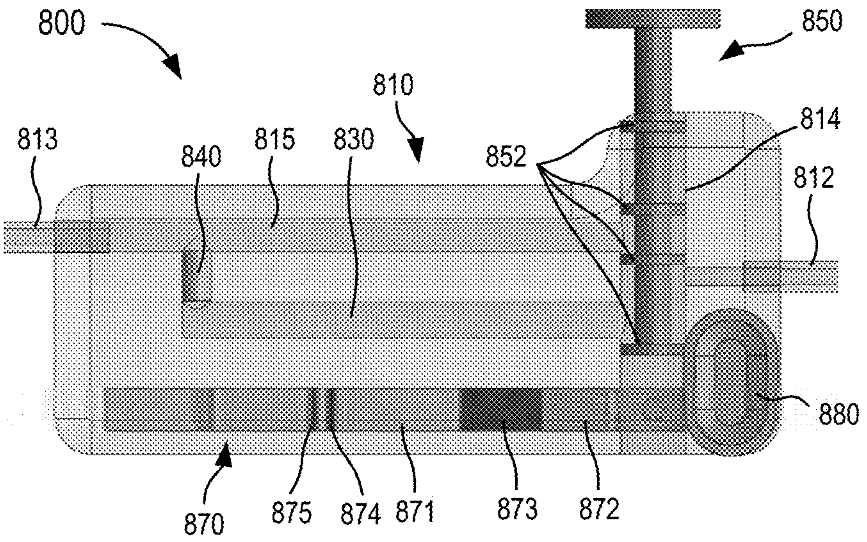
FIG. 11 is a side view of the fluid transfer and assay device (or system) of FIG. 10, with a housing of the device being partially transparent to illustrate internal features of the device.

The transfer device 805 includes at least a housing 810 and an actuator 850. The housing 810 of the device 805 can be any suitable shape, size, and/or configuration. For example, in some embodiments, the housing 810 can be similar to and/or the substantially the same as any of the housings 210, 310, 410, 510, 610, and/or 710 described above. Specifically, the housing 810 has and/or forms an inlet 812 and an outlet 813. The housing 810 can form and/or can define an actuator chamber 814, a fluid flow path 815, and a sequestration chamber 830. The inlet 812 can be any suitable inlet or port and can be configured to establish fluid communication between the housing 810 to a bodily fluid source (e.g., a patient). As shown in FIG. 11, the inlet 812 is in fluid communication with the actuator chamber 814, which in turn, is in fluid communication with the fluid flow path 815 and the sequestration chamber 830. The outlet 813 can be any suitable outlet or port and can be configured to establish fluid communication between the housing 810 and a fluid collection device (not shown in FIGS. 10-12D), such as any of those described in detail above. The outlet 813 is in fluid communication with the fluid flow path 815. In addition, the outlet 813 is configured to be in selective fluid communication with the sequestration chamber 830 via a flow controller 840, as described in further detail herein.

The sequestration chamber 830 can be configured to receive a flow and/or volume of bodily fluid from the inlet 812 and to sequester (e.g., separate, segregate, contain, retain, isolate, etc.) at least a portion of the flow and/or volume of bodily fluid within the sequestration chamber 830, as described in further detail herein. The sequestration chamber 830 can have any suitable shape, size, and/or configuration. For example, in some embodiments, the sequestration chamber 830 and/or at least a portion thereof can be substantially similar in at least form and/or function to the sequestration chambers 330, 430, 630, and/or 730 described in detail above. Thus, portions and/or aspects of the sequestration chamber 830 are not described in further detail herein.

The flow controller 840 is at least partially disposed within the housing 810 and is configured to control, direct, and/or otherwise facilitate a selective flow of fluid through at least a portion of the housing 810, at least a portion of the fluid flow path 815, and/or at least a portion of the sequestration chamber 830. The flow controller 840 can be configured to facilitate fluid displacement through one or more portions of the housing 810, which in some instances, can allow for or result in a pressure differential and/or pressure equalization across one or more portions of the housing 810. In this context, the flow of fluids, for example, can be a liquid such as water, oil, dampening fluid, bodily fluid, and/or any other suitable liquid, and/or can be a gas such as air, oxygen, carbon dioxide, helium, nitrogen, ethylene oxide, and/or any other suitable gas.

The flow controller 840 can be any suitable shape, size, and/or configuration. In some embodiments, the flow controller 840 can be similar to and/or substantially the same as the flow controller 340 described in detail above with reference to FIG. 4. For example, the flow controller 840 can be configured to transition from a first state to a second state in response to a pressure differential, suction force, contact with and/or a flow of bodily fluid, and/or the like. More specifically, in the embodiment shown in FIGS. 10-12D, the flow controller 840 can be a member or device formed of an absorbent or semi-permeable material configured to be permeable to a flow of a gas or air and impermeable to a flow of a liquid (e.g., blood or other bodily fluid) when in a first state and configured to be impermeable to both gases and liquids when in a second state. Accordingly, the flow controller 840 and/or aspects or portions thereof are not described in further detail herein.

The actuator 850 of the device 805 can be any suitable shape, size, and/or configuration. For example, the actuator 850 can be any suitable member(s) or device(s) configured to transition between any number of states (e.g., two, three, four, or more) and in any suitable manner (e.g., user actuation, automatic actuation, mechanical actuation, electronic actuation, chemical actuation, and/or the like). In some embodiments, the actuator 850 and/or aspects or portions thereof can be similar to and/or substantially the same as the actuators 150, 250, 350, 450, 650, and/or 750 described in detail above. As shown in FIG. 11, the actuator 850 forms and/or includes a rod that is at least partially movably disposed in a portion of the actuator chamber 814 of the housing 810. In addition, the actuator 850 includes a set of seals 852 disposed at predetermined positions along a length of the actuator 850 (or rod) that can allow the actuator 850 to control, direct, and/or otherwise facilitate a selective flow of fluid through at least a portion of the housing 810. As described in further detail herein, the actuator 850 includes a set of four seals 852 that are disposed at desired positions along a length of the actuator 850 (or rod) to selectively control fluid flow from the inlet 812 and into at least one of the sequestration chamber 830, the rapid diagnostic testing device 870, and/or the fluid flow path 815. Moreover, the arrangement of the seals 852 can also allow the actuator 850 to sequester the sequestration chamber 830, the rapid diagnostic testing device 870, and/or the fluid flow path 815 as the actuator 850 is transitioned between two or more states.

While the rapid testing devices included in the previous embodiments have be shown and/or described as being coupled to the housing 810, in the embodiment shown in FIGS. 10-12D, the rapid testing device 870 is disposed within and/or integrated into the housing 810. The rapid diagnostic testing device 870 (also referred to herein as "rapid testing device" or simply "testing device") can be any suitable testing device. For example, the rapid testing device 870 and/or aspects or portions thereof can be substantially similar to the rapid testing devices 170, 270, 370, 470, 570, 670, and/or 770 described in detail above. In some implementations, the rapid testing device 870 can be an LFA or the like, as described in detail above with reference to the LFA 170A shown in FIG. 2.

For example, as shown in FIG. 11, the rapid testing device 870 includes at least a sample element 872 disposed on an end portion of a substrate 871, a conjugate element 873 disposed on the substrate 871 downstream of the sample element 872, a capture element 874 disposed on the substrate 871 downstream of the conjugate element 873, and a control element 875 disposed on the substrate 871 downstream of the capture element 874. The rapid testing device 870 can be disposed within the housing 810 such that the capture element 874 and the control element 875 can be viewed from outside of the housing 810 via a viewing opening 819 or the like. Moreover, the housing 810 and/or the rapid testing device 870 includes and/or is coupled to a buffer actuator 880 that contains a volume of a buffer solution 881. In some embodiments, the buffer actuator 880 can be a blister pack, a frangible or pierceable container, a reservoir including one or more reconfigurable portions (e.g., one or more valves or flow controllers), and/or the like. The buffer actuator 880 can be actuated to provide the sample element 872 of the rapid testing device 870 with a flow of the buffer solution 881, which in turn, can mix with the volume of bodily fluid transferred to the sample element 872, as described in further detail herein.

The system 800 can be used to procure one or more volumes of bodily fluid from a patient, which can be used in one or more tests, assays, and/or diagnostic procedures. As described above, for example, the inlet 812 can be placed in fluid communication with a bodily fluid source. The actuator 850 can be in a first state when the inlet 812 is placed in fluid communication with the bodily fluid source (e.g., the portion of the patient), thereby establishing fluid communication between the inlet 812 and the sequestration chamber 830, as shown in FIG. 11. More specifically, when the actuator 850 is in the first state, the inlet 812 and the sequestration chamber 830 can be in fluid communication with a portion of the actuator chamber 814 defined between two of the seals 852 of the actuator 850. For example, a first seal 852 disposed at or near an end portion of the actuator 850 (e.g., an end seal) can be disposed within the actuator chamber 814 in a position between the rapid testing device 870 and the sequestration chamber 830 and a second seal 852 adjacent to (or closest to) the first or end seal 852 can be disposed within the actuator chamber 814 between the inlet 812 and the fluid flow path 815. In this manner, when the actuator 850 is in the first state, the inlet 812 is in fluid communication with the sequestration chamber 830, as shown in FIG. 11.

In the embodiment shown in FIGS. 10-12D, once the inlet 812 is placed in fluid communication with the bodily fluid source (e.g., the portion of the patient), the outlet 813 can be fluidically coupled to a fluid collection device, such as any of those described herein. For example, the fluid collection device can be any suitable reservoir, container, and/or device configured to receive a volume of bodily fluid. In some embodiments, the fluid collection device can be an evacuated reservoir or container that defines a negative pressure and/or can be a syringe that can be manipulated to produce a negative pressure. As such, coupling the fluid collection device to the outlet 813 selectively exposes at least a portion of the fluid flow path 815 to the negative pressure and/or suction force within the fluid collection device.

Figure 12A:
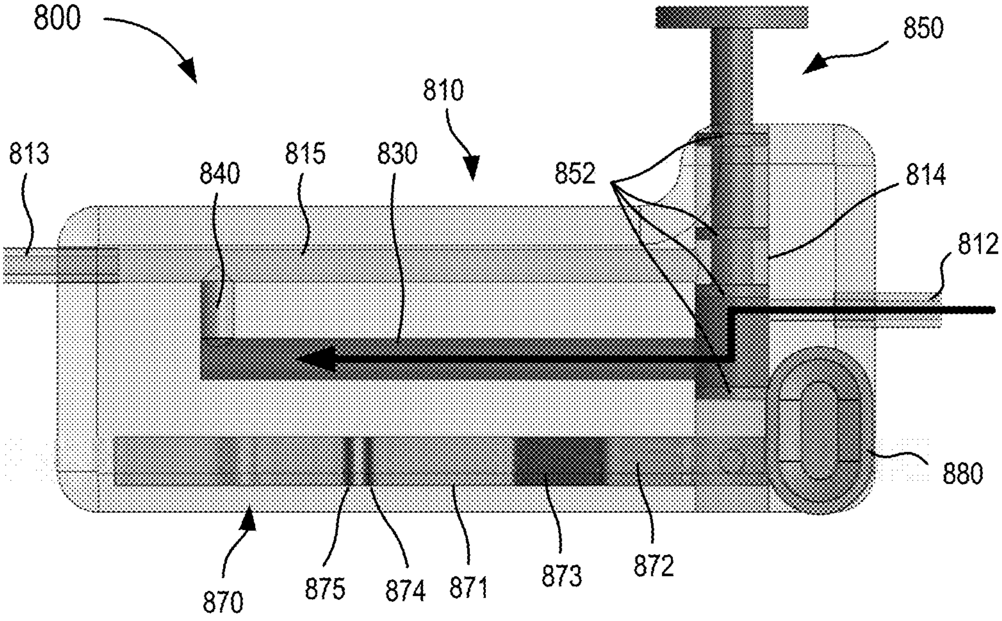
FIGS. 12A and 12B are side views of the fluid transfer and assay device (or system) of FIG. 11 in a first state.

The actuator 850 is configured to be in the first state when the fluid collection device is fluidically coupled to the outlet 813. As shown in FIG. 12A, the fluid flow path 815 is in fluid communication with a portion of the actuator chamber 814 defined between the seal 852 (e.g., second from the bottom) disposed between the inlet 812 and the fluid flow path 815 and an adjacent seal 852 (e.g., third from the bottom) disposed on an opposite side of the fluid flow path 815. In this manner, the fluid flow path 815 places the outlet 813 in fluid communication with a portion of the actuator chamber 814 that is sequestered and/or fluidically isolated by the seals 852 disposed on either side of the fluid flow path 815. As described above, the outlet 813 and/or the fluid flow path 815 is also in fluid communication with the flow controller 840, which can be in its first state when the fluid collection device is coupled to the outlet 813.

The arrangement of the flow controller 840 (e.g., the selectively permeable member) can be such that a flow of air or gas is allowed to pass through the flow controller 840 between the outlet 813 (and/or fluid flow path 815) and the sequestration chamber 830, while a flow of liquid (e.g., bodily fluid) is not allowed to pass through the flow controller 840. As a result, at least a portion of the negative pressure differential or suction force generated by the fluid collection device can be transferred into and/or through the sequestration chamber 830, which in turn, can be operable in drawing the initial volume of bodily fluid from the bodily fluid source, through the inlet 812, a portion of the actuator chamber 814 defined between the two corresponding seals 852, and into the sequestration chamber 830, as described in detail above with reference to the transfer device 305.

Figure 12B:
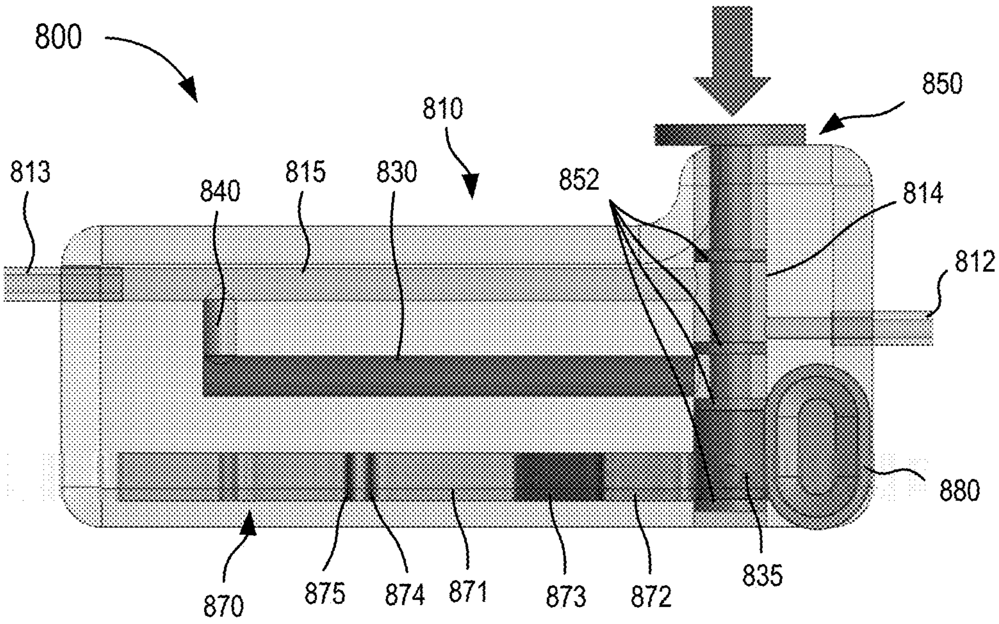

The initial volume of bodily fluid can be any suitable volume of bodily fluid, such as any of the volumes or amounts described above. For example, in some instances, the actuator 850 and/or the transfer device 805 can remain in the first state or configuration until a predetermined and/or desired volume (e.g., the initial volume) of bodily fluid is transferred to the sequestration chamber 830. In some embodiments, the initial volume can be associated with and/or at least partially based on a volume of the sequestration chamber 830 or a portion thereof (e.g., a volume sufficient to fill the sequestration chamber 830 or a desired portion of the sequestration chamber 830). In some embodiments, the transfer device 805 can be configured to transfer a flow of bodily fluid (e.g., the initial volume) into the sequestration chamber 830 until the flow controller 840 is transitioned to its second configuration. Said another way, in some embodiments, transferring the initial volume of bodily fluid into the sequestration chamber 830 can be operable to place the flow controller 840 in its second state or configuration. For example, transferring the initial volume of bodily fluid into the sequestration chamber 830 can be such that at least a portion of the initial volume wets and/or saturates the flow controller 840, which in turn, places the flow controller 840 in its second state, as described in detail above with reference to the flow controller 340. As shown in FIGS. 12A and 12B, the initial volume of bodily fluid can be sufficient to substantially fill the sequestration chamber 830 such that at least a portion of the initial volume is disposed within the actuator chamber 814 between the two seals 852 (e.g., the two lowest seals 852).

The flow controller 840 sequesters and/or fluidically isolates the sequestration chamber 830 from the outlet 813 when the flow controller 840 is transitioned to its second state and/or configuration. As such, the negative pressure and/or suction force produced by the fluid collection device no longer acts on or through the sequestration chamber 830. In some instances, this can allow a pressure differential between the sequestration chamber 830 and the inlet 812 to be substantially equalized and/or to be reduced below a desired threshold. In some instances, the pressure equalization can be such that a flow of bodily fluid into the sequestration chamber 830 stops.

The actuator 850 can be transitioned from its first state (FIGS. 11 and 12A) to its second state (FIGS. 12B and 12C) after the initial volume of bodily fluid is contained in the sequestration 830, thereby transitioning the transfer device 805 from its first state to its second state. As described above with reference to the transfer device 605, the transitioning of the actuator 850 from the first state to the second state can be in response to the initial volume of bodily fluid being disposed in the sequestration chamber 830, in response to an equalization of one or more pressure differentials, and/or the like. In some instances, the transitioning can be automatic or in response to an applied force (e.g., as indicated by the arrow in FIG. 12B).

As shown in FIG. 12B, when in the second state or configuration, the actuator 850 can be disposed within the actuator chamber 814 such that the seals 852 are in desired positions relative to the rapid testing device 870, the sequestration chamber 830, the inlet 812, and the fluid flow path 815. For example, the sequestration chamber 830 is in fluid communication with a portion of the actuator chamber 814 disposed between a seal 852 positioned between the rapid testing device 870 and the sequestration chamber 830 and a seal 852 positioned between the sequestration chamber 830 and the inlet 812. As such, when the flow controller 840 is in its second state and the actuator 850 is transitioned to its second state, the sequestration chamber 830 is sequestered and/or fluidically isolated from other portions of the transfer device 805 (see e.g., FIGS. 12B-12D). Said another way, the actuator 850 (and the flow controller 840) can sequester and/or isolate the sequestration chamber 830 from the inlet 812, the outlet 813, the fluid flow path 815, and the rapid testing device 870. In some instances, sequestering the initial volume of bodily fluid in the sequestration chamber 830 can also sequester contaminants in the initial volume.

Figure 12C:
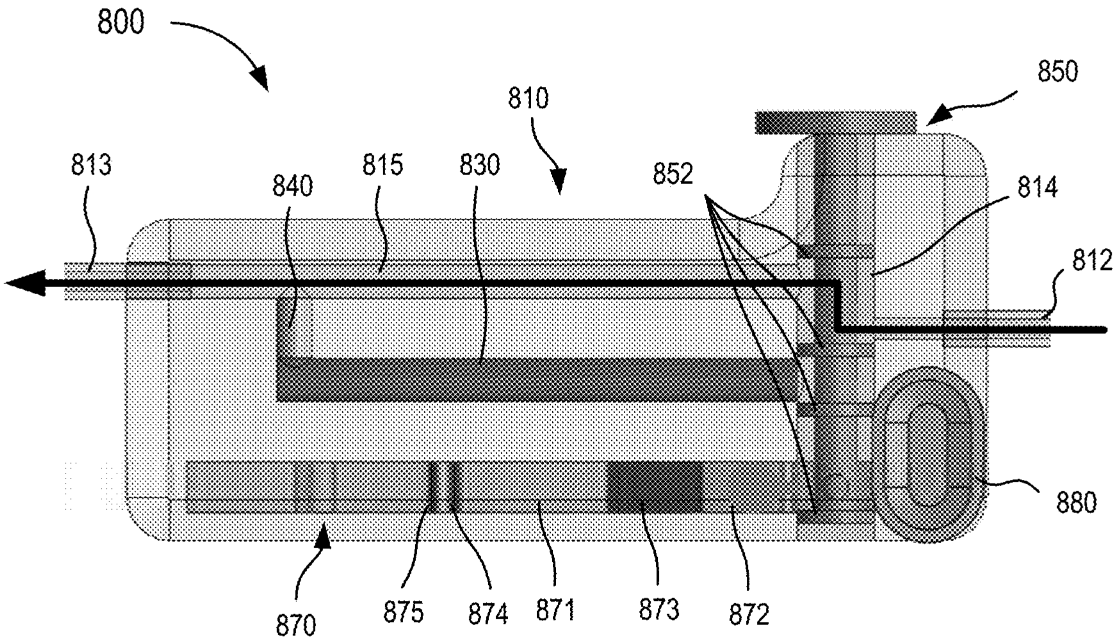
FIG. 12C is a side view of the fluid transfer and assay device (or system) of FIG. 11 in a second state.

As shown in FIG. 12C, when in the second state or configuration, the actuator 850 also establishes fluid communication between the inlet 812 and the outlet 813 via the fluid flow path 815 and a portion of the actuator chamber 814. For example, in some embodiments, the inlet 812 and the fluid flow path 815 are each in fluid communication with a portion of the actuator chamber 814 disposed between a corresponding pair of the seals 852 (e.g., a top pair of seals 852). Thus, in response to the negative pressure and/or suction force generated by the fluid collection device, one or more subsequent volume(s) of the bodily fluid can flow from the inlet 812, through the portion of the actuator chamber 814 and the fluid flow path 815, through the outlet 813, and into the fluid collection device (not shown). As described above, sequestering the initial volume of bodily fluid in the sequestration chamber 830 prior to collecting or procuring one or more subsequent volumes of bodily fluid reduces and/or substantially eliminates an amount of contaminants in the one or more subsequent volumes.

Figure 12D:
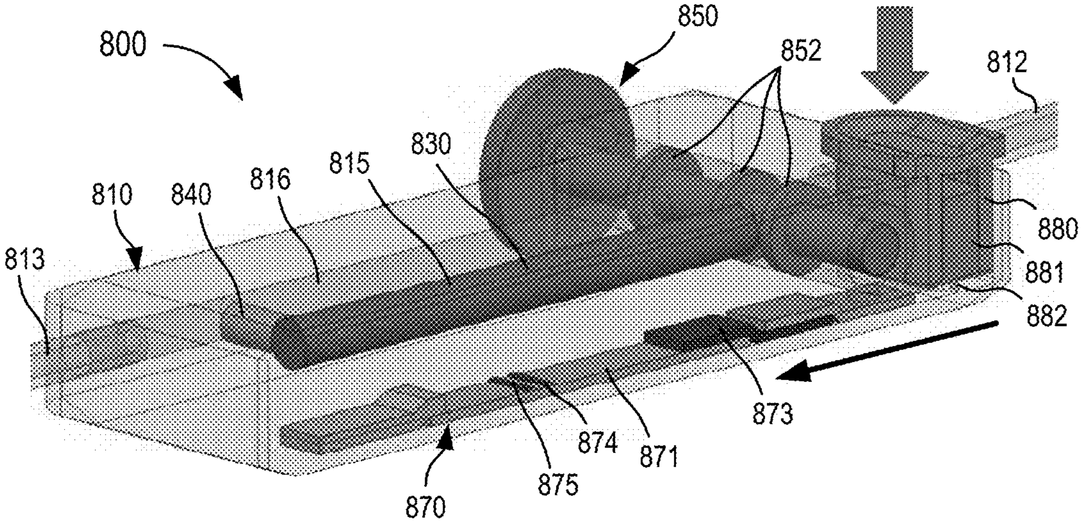
FIG. 12D is side perspective view of the fluid transfer and assay device (or system) of FIG. 11 in a third state.

As shown in FIG. 12C, when the actuator 850 is in the second state or configuration, the rapid testing device 870 is in fluid communication with a portion of the actuator chamber 814 disposed between a corresponding pair of seals 852 (e.g., an end pair), which can allow a portion of the initial volume of bodily fluid disposed within the actuator chamber 814 between the pair of seals 852 to be transferred into or onto the sample element 872 of the rapid testing device 870. As shown in FIG. 12D, the transfer device 805 can be transitioned from its second state to a third state by manipulating and/or engaging the buffer actuator 880 to transition the buffer actuator 880 from its first state to its second state to transfer at least a portion of the buffer solution 881 contained therein into or onto the sample element 872. For example, the buffer actuator 880 can include a frangible portion that can be broken and/or punctured in response applied by a user on the buffer actuator 880. As shown in FIG. 12D, the rapid testing device 870 and/or the housing 810 can include a puncture member 882 or the like that can be configured to break, puncture, and/or otherwise open the buffer solution. In such embodiments, the puncture member 882 can define a lumen that can be in fluid communication with the sample element 872. Thus, the force applied on the buffer actuator 880 can be operable to transfer at least a portion of the buffer solution 881 into and/or onto the sample element 872. Moreover, with volume of bodily fluid also transferred to the sample element 872, the bodily fluid and the buffer solution 881 can begin to mix.

In some embodiments, the mixing of the bodily fluid and the buffer solution 881 in or on the sample element 872 can initiate a test and/or assay of or on the bodily fluid, as described in detail above with reference to the rapid testing device 270. Moreover, the rapid testing device 870 can be configured to perform any suitable test and/or assay. In some embodiments, the buffer solution 881 can be based at least in part on the test being performed. For example, in some instances, the rapid testing device 870 can be configured to test for the presence of lactate and/or PCT, as described in detail above. Moreover, once the test or assay is complete, the rapid testing device 870 can be configured to output a test result, which can be detected and/or assessed. For example, in some instances, a human may observe the capture element 874 and/or the control element 875 via the viewing opening 819 defined by the housing 810. In other embodiments, an electronic device can perform one or more scans of the capture element 874 and/or the control element 875 via the viewing opening 819. In other embodiments, one or more electronic devices can be integrated and/or disposed in the housing 810 and the capture element 874 and/or the control element 875 need not be observed by a human.

As described in detail above, in some implementations, the arrangement of the rapid testing device 870 can be such that the tests and/or assays performed by the rapid testing device 870 are not susceptible to such contamination, which means that the accuracy of the test results output by the rapid testing device 870 is not affected by contamination that may be contained in the initial volume of bodily fluid, as described in detail above. Accordingly, the system 800 can be configured to procure the initial volume of bodily fluid, which can be used in rapid testing that has relatively low sensitivity to contamination, and the subsequent volume(s) of bodily fluid, which can be used in testing that has a relatively high sensitivity to contamination, as described above with reference to the systems 100, 200, 300, 400, 600, and/or 700.

FIGS. 13-16 illustrate at least a portion of a fluid transfer and assay system 900, according to an embodiment. The fluid transfer and assay system 900 (also referred to herein as "system") can include at least a fluid transfer device 905 and a rapid diagnostic testing device 970. Portions and/or aspects of the system 900 can be similar to and/or substantially the same as the systems (or devices) 100, 200, 300, 400, 500, 600, 700, and/or 800 described in detail above. Accordingly, such portions and/or aspects are not described in further detail herein.

The fluid transfer device 905 (also referred to herein as "transfer device") can be any suitable shape, size, and/or configuration. In some implementations, the transfer device 905 can be configured to withdraw bodily fluid (e.g., blood) from a patient and into and/or through the transfer device 905. In addition, the transfer device 905 can be configured to transfer at least some of the withdrawn bodily fluid to one or more other devices, reservoirs, containers, vials, machines, tests, assays, etc., such as the rapid diagnostic testing device 970 and/or one or more fluid collection devices (not shown in FIGS. 13-16). In some implementations, the transfer device 905 and/or aspects or portions thereof can be substantially similar to any of the transfer devices 105, 205, 305, 405, 505, 605, 705, and/or 805 described in detail above.

For example, the transfer device 905 includes at least a housing 910 and an actuator 950. The housing 910 has and/or forms an inlet 912 and an outlet 913. The inlet 912 can be any suitable inlet or port and can be configured to establish fluid communication between the housing 910 to a bodily fluid source (e.g., a patient). The outlet 913 can be any suitable outlet or port and can be configured to establish fluid communication between the housing 910 and a fluid collection device (not shown in FIGS. 13-16), such as any of those described in detail above. In addition, the housing 910 includes and/or defines a port 925 that can be configured to establish fluid communication between at least a portion of the housing 910 and/or one or more reservoirs or chambers disposed therein and, for example, the rapid diagnostic testing device 970. In some embodiments, the port 925 can be substantially similar in at least form and/or function to the port 525 described above with reference to FIGS. 6A-6D. In this manner, the housing 910 and/or portions or aspects thereof can be similar to and/or the substantially the same as any of the housings 210, 310, 410, 510, 610, 710, and/or 810 described above and thus, is/are not described in further detail herein.

The actuator 950 is at least partially disposed within the housing 910. The actuator 950 of the device 905 can be any suitable shape, size, and/or configuration. For example, the actuator 950 can be a member or device configured to transition between two or more states to control, direct, and/or otherwise facilitate a selective flow of fluid through at least a portion of the housing 910. Moreover, the actuator 950 can be actuated and/or transitioned between any number of states in any suitable manner. In the embodiment shown in FIGS. 13-16, the actuator 950 can be transitioned between at least a first state and a second state. When in the first state, the actuator 950 can be configured to allow an initial volume bodily fluid to from the inlet 912 into an initial or first portion of the housing 910 such as a sequestration chamber or the like described in detail above with reference to the sequestration chambers 330, 430, 630, 730, and/or 830. In some embodiments, the actuator 950 can be configured to sequester, separate, isolate, and/or otherwise prevent fluid communication between the outlet 913 and the inlet 912, and/or the outlet 913 and the initial or first portion of the housing 910 when in the first state. When in the second state, the actuator 950 can be configured to allow a subsequent volume of bodily fluid (e.g., a volume of bodily fluid after the initial volume of bodily fluid) to be transferred from the inlet 912, through at least a portion of the housing 910 (e.g., a second portion) and to the outlet 913 (and/or the fluid collection device fluidically coupled to the outlet 913). In addition, when in the second state, the actuator 950 can be configured to sequester, separate, isolate, and/or otherwise prevent fluid communication between the initial or first portion of the housing 910 and the inlet 912, the outlet 913, and/or one or more other portions of the housing 910. In this manner, the actuator 950 and/or portions or aspects thereof can be substantially similar to any of the actuators 250, 350, 450, 650, 750, and/or 850 described in detail above and thus, is/are not described in further detail herein.

The rapid diagnostic testing device 970 (also referred to herein as "rapid testing device" or simply "testing device") can be any suitable testing device. For example, the testing device 970 and/or aspects or portions thereof can be substantially similar to the rapid testing devices 170, 270, 370, 470, 570, 670, 770, and/or 870 described in detail above. In some implementations, the rapid testing device 970 can be an LFA or the like, as described in detail above with reference to the LFA 170A shown in FIG. 2. For example, the rapid testing device 970 includes at least a sample element 972 disposed on an end portion of a substrate 971, a conjugate element 973 disposed on the substrate 971 downstream of the sample element 972, a capture element 974 disposed on the substrate 971 downstream of the conjugate element 973, and a control element 975 disposed on the substrate 971 downstream of the capture element 974.

The rapid testing device 970 also includes a housing 983 configured to contain and/or house at least a portion of the rapid testing device 970 and a testing device actuator 986 configured to selectively establish fluid communication between the rapid testing device 970 and the housing 910. In some embodiments, the rapid testing device 970 can be configured as a substantially modular device that can be coupled to and/or attached to any suitable fluid transfer device, tubing, reservoir, mechanism, transfer adapter, etc. In some implementations, the modular arrangement of the testing device 970 can allow the transfer device 905 and the testing device 970 to be manufactured and/or shipped independently and coupled and/or assembled at a point of use. In some implementations, the modular arrangement of the testing device 970 can allow various versions of the testing device 970 to be compatible with the transfer device 905, with each version of the testing device 970 being configured to perform a different test or assay. Said another way, the modular arrangement of the testing device 970 can allow different versions of the testing device 970 to test for different biomarkers while maintaining substantially the same form factor and/or compatibility.

Figure 14:
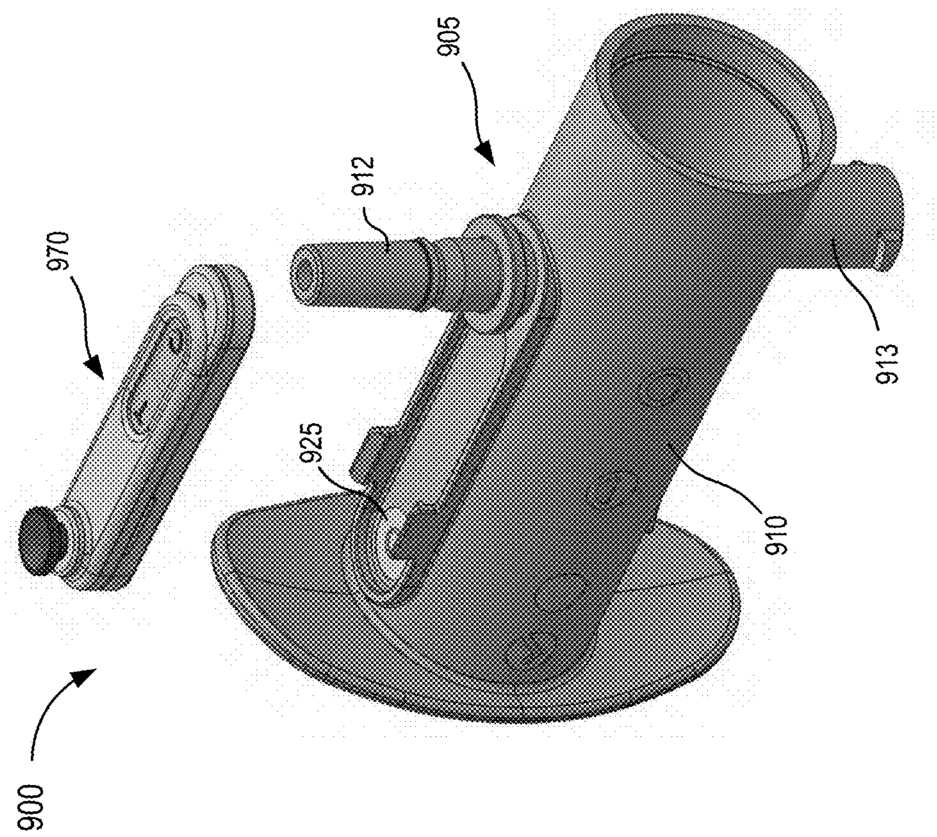
FIGS. 13-16 are various views of a fluid transfer and assay device (or system) according to an embodiment.
Figure 13:
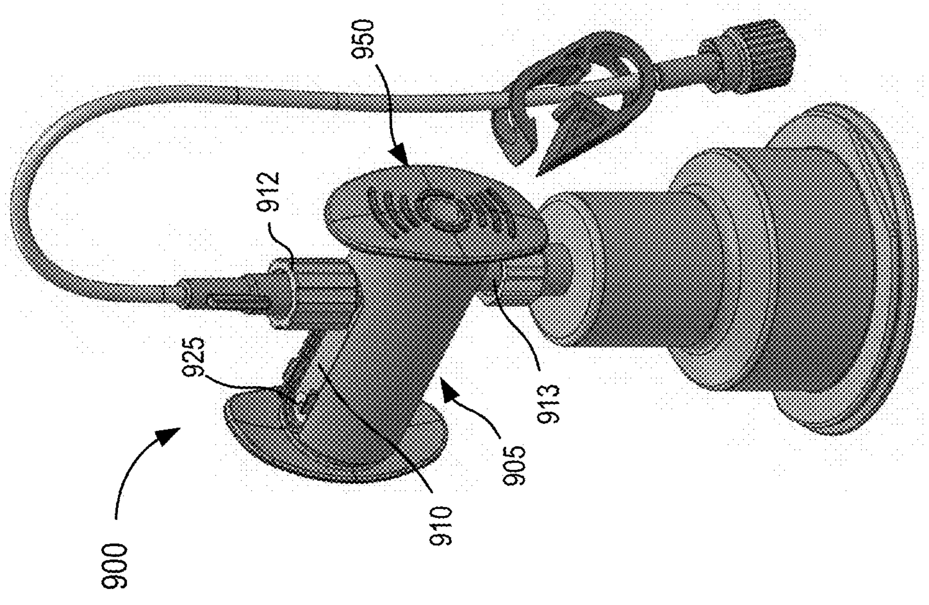
Figure 16:
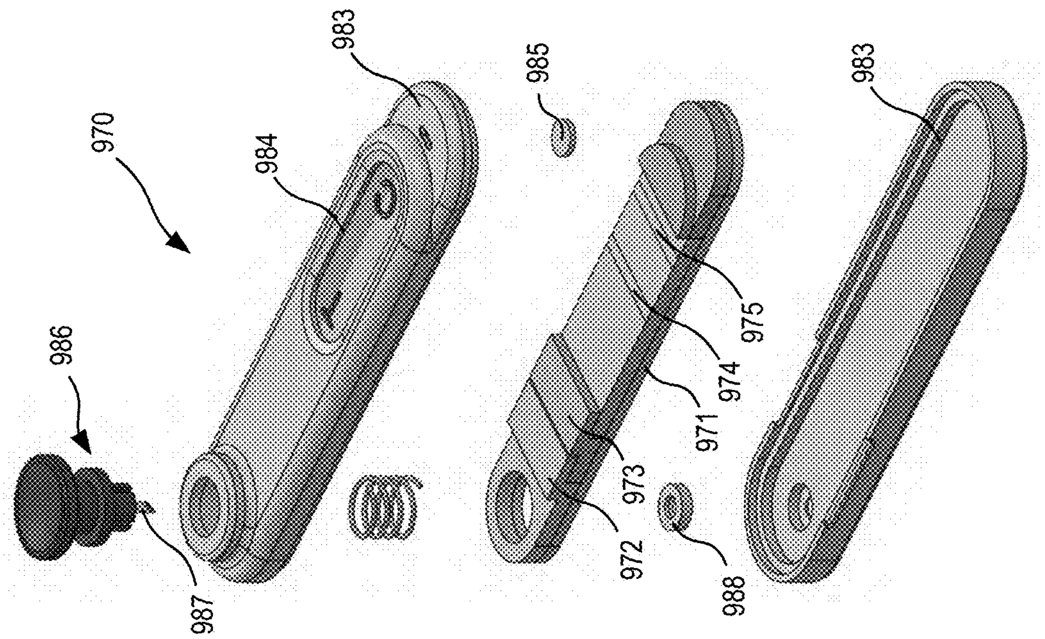
Figure 15:
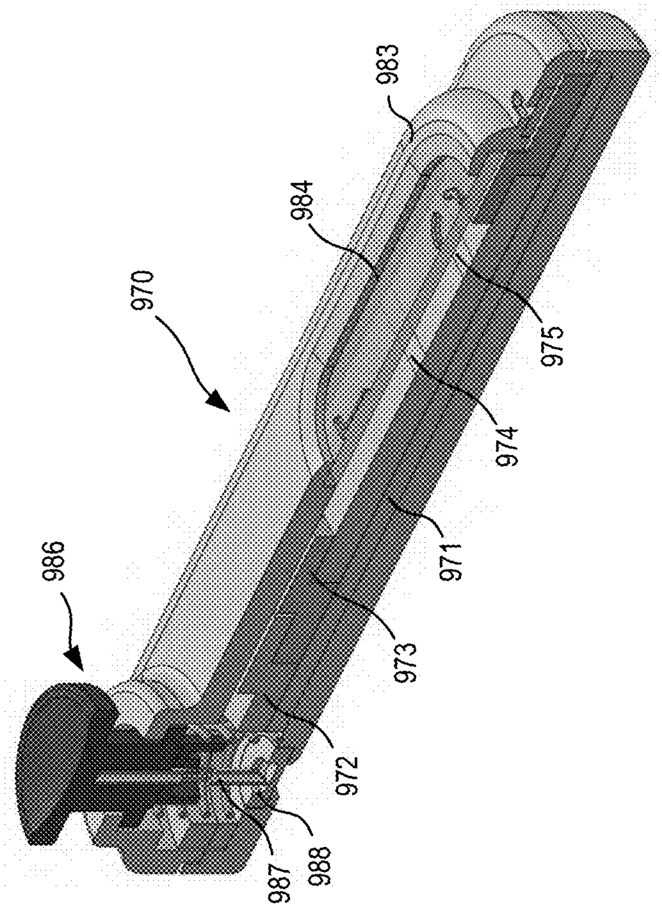

As shown in FIGS. 14-16, the housing 983 can be any suitable shape, size, and/or configuration. In some embodiments, the housing 983 of the testing device 970 can be configured to be coupled to a portion of the housing 910 of the transfer device 905. The housing 983 includes, houses, and/or defines a vent 985 configured to allow a flow of air or gas out of the housing 983. As described in detail above with reference to the transfer devices, in some implementations, venting the housing 983 of the testing device 970 can facilitate a flow of fluid through the testing device 970 (e.g., along the substrate 971). In addition, the housing 983 includes and/or defines a viewing opening 984. As shown in FIGS. 14 and 15, the testing device 970 can be disposed within the housing 983 such that at least the capture element 974 and/or the control element 975 are visible and/or detectable via the viewing opening 984.

The testing device actuator 986 is movably coupled to the housing 983 of the testing device 970 and is configured to be transitioned between a first state and a second state to establish fluid communication between the transfer device 905 and the testing device 905. For example, in some embodiments, the testing device actuator 986 can be a spring loaded button or the like that can include a puncture member 987. The testing device 970 and/or the housing 983 of the testing device 970 can include and/or can form a septum 988. In addition, the testing device actuator 986 can be aligned with the septum 988. In some implementations, the testing device actuator 986 can be configured such that the puncture member 987 is disposed on a first side of the septum 988 and within the housing 983 of the testing device 970 when the testing device actuator 986 is in a first state (see e.g., FIG. 15) and the puncture member 987 extends through the septum 988 and outside of the housing 983 of the testing device 970 when the testing device actuator 986 is in a second state (not shown in FIGS. 13-16).

The testing device 970 and/or the housing 983 thereof is configured to couple to the housing 910 of the transfer device 905 such that the testing device actuator 986 is substantially aligned with the port 925 included in and/or formed by the housing 910. As such, when the testing device actuator 986 is transitioned to its second state, the puncture member 987 can extend through the septum 988 of the testing device 970 and through the port 925 of the transfer device 905 to establish fluid communication therebetween. In this manner, the puncture member 987 can receive at least portion of the initial volume of bodily fluid disposed in the transfer device 905 (e.g., via capillary action, a pressure differential, and/or any other fluid transfer modality). As shown in FIG. 15, the puncture member 987 is in fluid communication with the portion of the substrate 971 such as, for example, the sample element 972. Thus, a flow of bodily fluid can be transferred from a portion of the transfer device 905 (e.g., a portion of the housing, a sequestration chamber, and/or the like) to the sample element 972.

Although not shown in FIGS. 13-16, in some implementations, the testing device 970 can be configured to convey a buffer solution or the like to the sample element 972 in conjunction with the volume of bodily fluid (e.g., as described above with reference to the testing device 870). In such implementations, the buffer solution can mix with the volume of bodily fluid and the mixture can flow along the substrate 971 for testing, as described in detail above. In some implementations, the rapid testing device 970 can be configured to test for the presence of lactate and/or PCT, which can be indicative of a patient condition such as sepsis. Moreover, once the test or assay is complete, the rapid testing device 970 can be configured to output a test result, which can be detected and/or assessed. For example, in some instances, a human may observe the capture element 974 and/or the control element 975 via the viewing opening 984 defined by the housing 983 of the testing device 970. In other embodiments, an electronic device can perform one or more scans of the capture element 974 and/or the control element 975 via the viewing opening 984. In other embodiments, one or more electronic devices can be integrated and/or disposed in the housing 910 and the capture element 974 and/or the control element 975 need not be observed by a human.

In addition to transferring a volume of bodily fluid to the rapid testing device 970, in some instances, the transfer device 905 can be configured to transfer one or more subsequent volumes of bodily fluid to any suitable device, reservoir, test, etc. coupled to the outlet 913. Accordingly, the system 900 can be configured to procure the initial volume of bodily fluid, which can be used in rapid testing (e.g., that has relatively low sensitivity to contamination), and the subsequent volume(s) of bodily fluid, which can be used in subsequent testing (e.g., that has a relatively high sensitivity to contamination), as described above with reference to the systems 100, 200, 300, 400, 600, 700, and/or 800.

Figure 17:
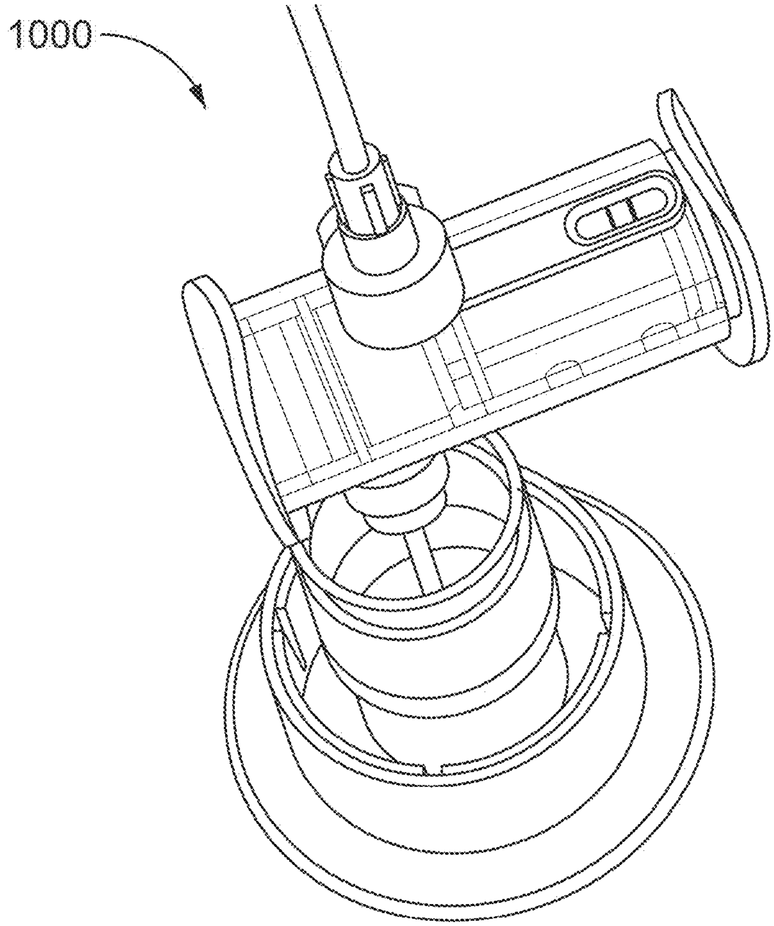
FIGS. 17-20 are various views of a fluid transfer and assay device (or system), each according to a different embodiment.

FIGS. 17-20 illustrate various examples of fluid transfer and assay systems and/or devices according to different embodiments. For example, FIG. 17 illustrates a fluid transfer and assay system 1000 (also referred to herein as "system"). The system 1000 can be substantially similar in form and/or function to the system 900 described above with reference to FIGS. 13-16. While the port 925 of the transfer device 905 is shown in FIG. 14 as being disposed at or near an end portion of the housing 910, in the embodiment shown in FIG. 17, a transfer device included in the system 1000 can include and/or form a port disposed near or adjacent to an inlet thereof. In this manner, a flow of bodily fluid through a rapid testing device that is coupled to the transfer device of the system 1000 can be in a substantially opposite direction relative to a flow of bodily fluid through, for example, the rapid testing device 970 described above with reference to FIGS. 13-17.

Figure 18:
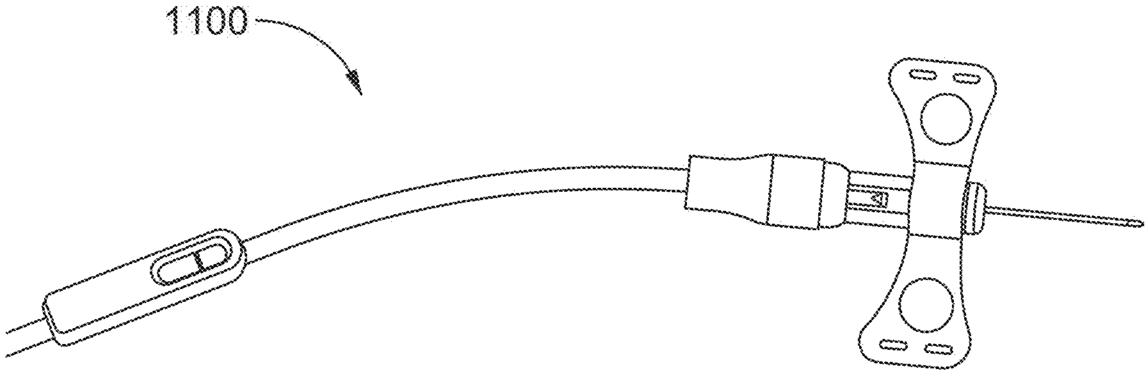

FIG. 18 illustrates a fluid transfer and assay system 1100 (also referred to herein as "system"). In this embodiment, the system 1100 includes an "in-line" rapid diagnostic testing device. For example, in some embodiments, the system 1100 can include an in-line rapid diagnostic testing device that is included in and/or coupled to and inlet tubing, an outlet tubing, and/or any other suitable portion of the system 1100. In some implementations, the in-line rapid testing device included in the system can receive a flow of bodily fluid and can perform a test or assay as described in detail above. Moreover, in some instances, the in-line rapid testing device can include one or more flow through or bypass mechanisms or the like (e.g., an automatic or manually actuated mechanism) that can allow a flow of bodily fluid through the in-line rapid testing device after it receives an initial volume of bodily fluid. Thus, the in-line rapid testing device can perform one or more tests or assays on an initial volume of bodily fluid while a subsequent volume of bodily fluid continues to flow through the system 1100.

Figure 19:
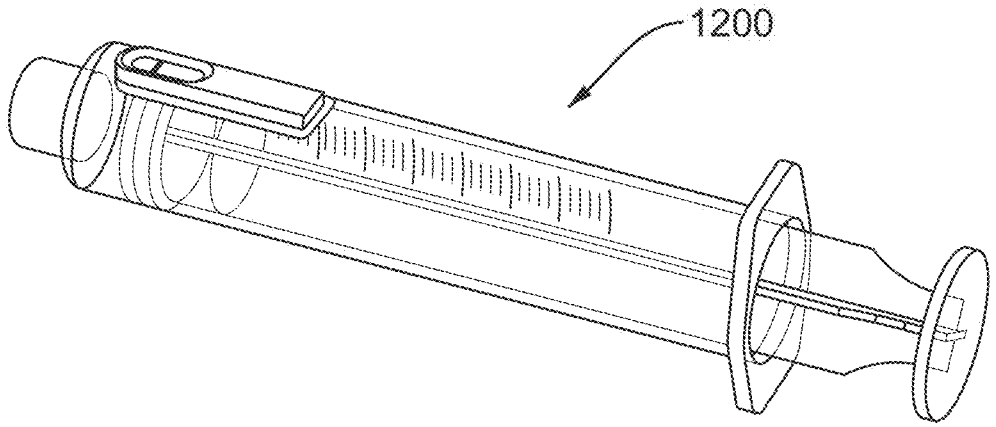

FIG. 19 illustrates a fluid transfer and assay system 1200 (also referred to herein as "system"). In this embodiment, the system 1200 includes a fluid transfer device that is configured as a syringe. In some embodiments, the syringe can be, for example, a standard syringe configured to withdraw a volume of bodily fluid. In other embodiments, the syringe can be, for example, a syringe configured to withdraw and sequester an initial volume of bodily fluid prior to withdrawing a "sample volume" of bodily fluid. For example, such a syringe can be similar to and/or substantially the same as any of those described in the '495 patent and/or the '006 publication incorporated by reference above. As shown in FIG. 19, the system 1200 can include a rapid diagnostic testing device that can be coupled to any suitable portion of the syringe to be placed in fluid communication with an inner volume thereof. In embodiments in which the syringe is configured to withdraw and sequester an initial volume of bodily fluid, the rapid testing device can couple to the syringe such that fluid communication is established between the sequestered portion of the syringe and the rapid testing device. In this manner, the system 1200 can be similar to at least the systems 300, 400, 600, 700, and/or 800 described in detail above.

Figure 20:
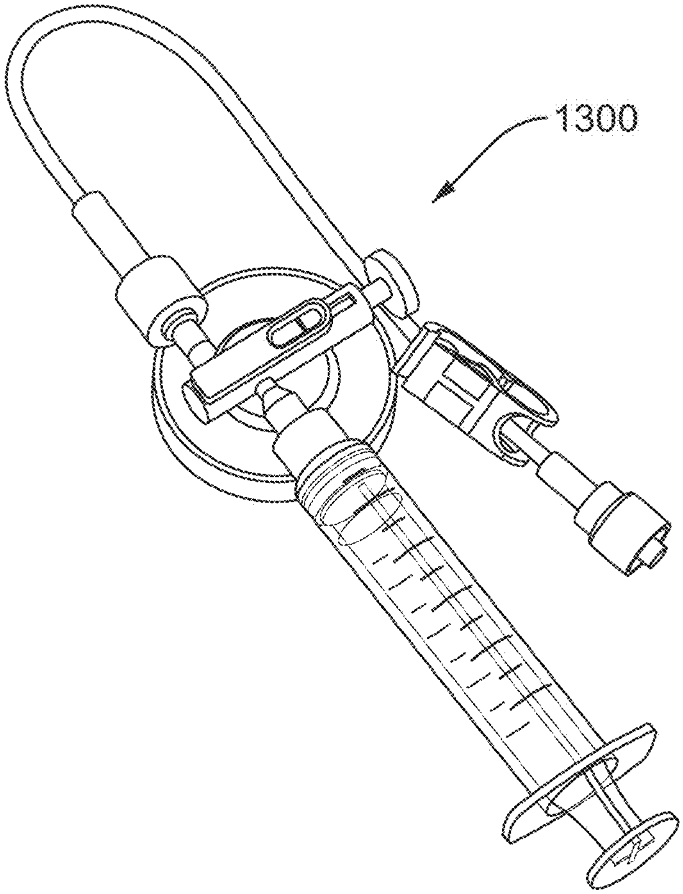

FIG. 20 illustrates a fluid transfer and assay system 1300 (also referred to herein as "system"). In this embodiment, the system 1300 includes a fluid transfer device that is fluidically coupled to, for example, a syringe. As described above with reference at least the systems 200, 300, and 800, the system 1300 can include a fluid transfer device that is configured to withdraw an initial volume of bodily fluid into a sequestration chamber and configured to withdraw a subsequent volume of bodily fluid in response to, for example, a negative pressure differential produced by a fluid collection device or the like. While some of the embodiments are described herein as being coupled to an evacuated container (e.g., a Vacutainer® or the like), the embodiment shown in FIG. 20 is configured to be coupled to a syringe that can be manipulated to produce a negative pressure differential. Moreover, the fluid transfer device shown in FIG. 20 is configured to be coupled to a rapid testing device such as any of those described herein. In this manner, the system 1300 can be similar in at least form and/or function to any of the systems described in detail herein.

While various embodiments have been described above, it should be understood that they have been presented by way of example only, and not limitation. For example, while some of the embodiments are described herein as being used for procuring bodily fluid for one or more assays, tests, and/or the like, it should be understood that the embodiments are not limited to such a use. Any of the embodiments and/or methods described herein can be used to transfer a flow of bodily fluid to any suitable device that is placed in fluid communication therewith. Thus, while specific examples are described herein, the devices, methods, and/or concepts are not intended to be limited to such specific examples.

While the embodiments have been particularly shown and described, it will be understood that various changes in form and details may be made. Where schematics and/or embodiments indicate certain components arranged in certain orientations or positions, the arrangement of components may be modified. Although various embodiments have been described as having particular features, concepts, and/or combinations of components, other embodiments are possible having any combination or sub-combination of any features, concepts, and/or components from any of the embodiments described herein.

The specific configurations of the various components can also be varied. For example, the size and specific shape of the various components can be different from the embodiments shown, while still providing the functions as described herein. In some embodiments, varying the size and/or shape of such components may reduce an overall size of the device and/or may increase the ergonomics of the device without changing the function of the device. In some embodiments, the size and/or shape of the various components can be specifically selected for a desired or intended usage. For example, in some implementations, a device configured for use with or on seemingly healthy adult patients can be configured to procure a first amount of bodily fluid while a device configured for use with or on, for example, very sick patients and/or pediatric patients can be configured to procure a second amount of bodily fluid that is less than the first volume. Thus, it should be understood that the size, shape, and/or arrangement of the embodiments and/or components thereof can be adapted for a given use unless the context explicitly states otherwise.

The embodiments described herein and/or portions thereof can include components formed of one or more parts, features, structures, etc. When referring to such components it should be understood that the components can be formed by a singular part having any number of sections, regions, portions, and/or characteristics, or can be formed by multiple parts or features. For example, when referring to a structure such as a wall or chamber, the structure can be considered as a single structure with multiple portions, or as multiple, distinct substructures or the like coupled to form the structure. Thus, a monolithically constructed structure can include, for example, a set of substructures. Such a set of substructures may include multiple portions that are either continuous or discontinuous from each other. A set of substructures can also be fabricated from multiple items or components that are produced separately and are later joined together (e.g., via a weld, an adhesive, or any suitable method).

Any of the embodiments described herein can be used in conjunction with any suitable diagnostic testing device or machine, rapid diagnostic testing device, assay device (e.g., a lateral flow assay device), and/or the like. Any of the embodiments described herein can include and/or can be used in conjunction with any suitable fluid transfer device, fluid collection device, and/or fluid storage device such as, for example, a sample reservoir, vessel, container, bottle, adapter, dish, vial, syringe, and/or device (including, for example, micro- and/or nano-configurations thereof). Moreover, any of the embodiments described herein can incorporate, can include, and/or can be used in conjunction with any suitable fluid transfer device, transfer adapter, and/or component thereof such as any of the devices and/or components described in the '420 patent, the '783 patent, the '510 publication, the '117 publication, the '241 patent, the '724 patent, the '495 patent, the '006 publication, the '999 application, the '074 publication, the '380 application, and/or the '477 application, the disclosures of which are incorporated herein by reference in their entireties.

While some of the embodiments described above include a flow controller and/or actuator that physically and/or mechanically sequesters one or more portions of a fluid transfer device, in other embodiments, a fluid transfer device need not physically and/or mechanically sequester one or more portions of the fluid transfer device. For example, in some embodiments, an actuator such as any of those described herein can be transitioned from a first state in which an initial volume of bodily fluid can flow from an inlet to a sequestration chamber or portion, to a second state in which (1) the sequestration chamber or portion is physically and/or mechanically sequestered and (2) the inlet is in fluid communication with an outlet of the fluid transfer device. In other embodiments, however, an actuator and/or any other suitable portion of a fluid transfer device can transition from a first state in which an initial volume of bodily fluid can flow from an inlet to a sequestration chamber or portion, to a second state in which the inlet is placed in fluid communication with the outlet without physically and/or mechanically sequestering (or isolating) the sequestration chamber or portion. When such a transfer device is in the second state, one or more features and/or geometries of the transfer device can result in a preferential flow of bodily fluid from the inlet to the outlet and the initial volume of bodily fluid can be retained in the sequestration chamber or portion without physically and/or mechanically being sequestered or isolated.

Although not shown, any of the devices described herein can include an opening, port, coupler, septum, Luer-Lok, gasket, valve, threaded connecter, standard fluidic interface, etc. (referred to for simplicity as a "port") in fluid communication with the sequestration chamber. In some such embodiments, the port can be configured to couple to and/or accept any suitable device, reservoir, pressure source, testing device, etc. For example, in some embodiments, the port can be configured to couple to any of the rapid diagnostic testing devices described herein. In some embodiments, the port can be coupled to a negative pressure source such as an evacuated container, a pump, a syringe, and/or the like to collect a portion or the full volume of the bodily fluid in the sequestration chamber, channel, reservoir, etc. and can use that volume of bodily fluid (e.g., the pre-sample volume) for additional clinical and/or in vitro diagnostic testing purposes. In some embodiments, the sequestration chamber can be configured with the addition of rapid diagnostic testing components integrated into the chamber (e.g., any of the rapid diagnostic testing devices described herein) allowing at least a portion of the initial volume of bodily fluid to be used for that test. In still other embodiments, the sequestration chamber and/or a rapid testing device coupled to or forming a portion of the sequestration chamber can be designed, sized, and configured to be removable and compatible with testing equipment and/or specifically accessible for other types of bodily fluid tests commonly performed on patients with suspected conditions (e.g., the rapid diagnostic testing devices described herein configured to test for sepsis and/or the like). In some embodiments, a port (or the like) can be coupled to any suitable pressure source or infusion device configured to infuse at least a portion of the initial volume of bodily fluid sequestered in the sequestration chamber back into the patient and/or bodily fluid source (e.g., in the case of pediatric patients, very sick patients, patients having a low blood volume, and/or the like).

While some embodiments described herein include a rapid diagnostic testing device that is coupled to or inserted into a portion of a fluid transfer device to receive a volume of bodily fluid for testing, in other embodiments, rapid diagnostic testing device can be integrated into one or more portions of a transfer device. For example, any of the embodiments described herein can include an integrated transfer and assay device such as the device(s) described above with reference to the system 800. While the rapid testing device 870 is shown as being disposed or housed within the housing 810, in other embodiments, a rapid testing device can form and/or can be at least temporarily coupled to an outer portion of a fluid transfer device.

Although not shown, in some embodiments, a fluid transfer device can include one or more lumen, channels, flow paths, etc. configured to selectively allow for a "bypass" flow of bodily fluid, where an initial amount or volume of bodily fluid can flow from the inlet, through the lumen, cannel, flow path, etc. to bypass the sequestration chamber (or rapid testing device), and into the collection device. In some embodiments, the fluid transfer device can include an actuator having, for example, at least three states—a first in which bodily fluid can flow from the inlet to the sequestration chamber (or rapid testing device), a second in which bodily fluid can flow from the inlet to the outlet after the initial volume is sequestered in the sequestration chamber, and a third in which bodily fluid can flow from the inlet, through the bypass flow path, and to the outlet. In other embodiments, the transfer device can include a first actuator configured to transition the device between a first and second state, as described in detail above with reference to specific embodiments, and can include a second actuator configured to transition the device to a bypass configuration or the like. In still other embodiments, the transfer device can include any suitable device, feature, component, mechanism, actuator, controller, etc. configured to selectively place the fluid transfer device in a bypass configuration or state.

While some methods are described herein as including steps recited in a certain order, in other embodiments, the ordering of certain events and/or procedures in any of the methods or processes described herein may be modified and such modifications are in accordance with the variations of the invention. Additionally, certain events and/or procedures may be performed concurrently in a parallel process when possible, as well as performed sequentially as described above. Certain steps may be partially completed or may be omitted before proceeding to subsequent steps.

For example, while some devices are described herein as transitioning from a first state to a second state in a discrete operation or the like, it should be understood that the devices described herein can be configured to automatically and/or passively transition from the first state to the second state and that such a transitioning may occur over a period of time. In other words, the transitioning from the first state to the second state may, in some instances, be relatively gradual. For example, in some instances, as a last portion of an initial volume of bodily fluid is transferred into a device (e.g., an initial or sequestration portion thereof), the device can begin to transition from the first state to the second state. In some instances, the rate of change when transitioning from the first state to the second state can be selectively controlled to achieve one or more desired characteristics associated with the transition. Moreover, in some such instances, the inflow of the last portion of the initial volume can limit and/or substantially prevent bodily fluid already disposed in the initial or sequestration portion from escaping therefrom. Accordingly, while the transitioning from the first state to the second state may occur over a given amount of time, the initial or sequestration portion of the device can nonetheless sequester the initial volume of bodily fluid disposed therein.

Some embodiments and/or methods described herein include one or more electronic devices configured to perform one or more processes included in and/or associated with the fluid transfer and/or rapid diagnostic testing systems and methods described herein. The electronic device(s) described herein (e.g., the electronic device 190) can be any suitable hardware-based computing device configured to receive, process, define, and/or store data such as, for example, one or more diagnostic test results, test standards against which to measure results data, predetermined and/or predefined treatment plans, patient profiles, disease profiles, etc. In some instances, the electronic device(s) can receive data associated with a diagnostic test, assay, and/or the like (e.g., the rapid testing device 170) and can be configured to analyze, process, and/or otherwise use the data to produce one or more qualitative and/or quantitative test results associated with the tests. In some instances, such a test can be, for example, a test for sepsis and/or any other disease condition.

Examples of electronic devices and/or components thereof are provided below. While certain devices and/or components are described, it should be understood that they have been presented by way of example only, and not limitation. Any other suitable electronic devices and/or an electronic having any other suitable components that are capable of performing the processes, procedures, and/or methods described herein may be used.

The electronic device(s) described herein can be, for example, a mobile electronic device (e.g., a smartphone, a tablet, a laptop, and/or any other mobile or wearable device), a PC, a workstation, a server device or a distributed network of server devices, a virtual server or machine, a virtual private server and/or the like that is executed and/or run as an instance or guest on a physical server or group of servers, and/or any other suitable device. In some implementations, the electronic device(s) can be configured to provide a graphic and/or digital representation of the test results produced by any of the rapid testing devices described herein. In addition, in some implementations, based on data associated with and/or representing test results, the electronic device(s) can be configured to determine and graphically or digitally present one or more diagnoses, one or more treatment plans, one or more simulations, and/or any other suitable data associated with the bodily fluid sample, the patient, and/or the medical treatment of the patient.

The components of the electronic device(s) can be contained within a single housing or machine or can be distributed within and/or between multiple physical machines, virtual machines, and/or any combination thereof. In some embodiments, the electronic device(s) can be stored, run, executed, and/or otherwise implemented in a cloud-computing environment. In some embodiments, the electronic device(s) can include and/or can be collectively formed by a client or mobile device (e.g., a smartphone, a tablet, a wearable device, and/or the like) and a server or host device(s), which can be in communication via one or more networks. Moreover, the electronic device(s) and/or any of the components thereof can be included, housed, and/or integrated in any of the fluid transfer devices and/or rapid diagnostic testing devices described herein, or any suitable combination thereof.

The electronic device(s) included in the embodiments described herein can include at least a memory, a processor, and a communication interface. The memory, the processor, and the communication interface can be connected and/or electrically coupled (e.g., via a system bus or the like) such that electric and/or electronic signals may be sent between the memory, the processor, and the communication interface. The electronic device(s) can also include and/or can otherwise be operably coupled to a database and/or one or more user interfaces or input/output (I/O) devices, as described in further detail herein.

In some embodiments, a memory can be, for example, a random access memory (RAM), a memory buffer, a hard drive, a read-only memory (ROM), an erasable programmable read-only memory (EPROM), an electrically erasable programmable read-only memory (EEPROM), a flash memory, and/or the like, or suitable combinations thereof. In some implementations, the memory can be physically housed and/or contained in or by the electronic device(s) or can be operatively coupled to the electronic device(s) and/or at least the processor thereof. In such implementations, the memory can be, for example, included in and/or distributed across one or more devices such as, for example, server devices, cloud-based computing devices, network computing devices, and/or the like. The memory can be configured to store, for example, one or more software modules and/or code that can include instructions that can cause the processor to perform one or more processes, functions, and/or the like (e.g., processes, functions, etc. associated with storing, analyzing, and/or presenting data associated with the fluid transfer and/or rapid diagnostic testing systems and methods described herein).

The memory and/or at least a portion thereof can include and/or can be in communication with one or more data storage structures such as, for example, one or more databases and/or the like. A database can be any suitable data storage structure(s) such as, for example, a table, a repository, a relational database, an object-oriented database, an object-relational database, a structured query language (SQL) database, an extensible markup language (XML) database, and/or the like. In some embodiments, the database can be disposed in a housing, rack, and/or other physical structure including at least the memory, the processor, and/or the communication interface. In other embodiments, the electronic device(s) can include and/or can be operably coupled to any number of databases. In some implementations, the database can be configured to store data associated with the fluid transfer and/or rapid diagnostic testing systems and methods described herein.

In some embodiments, a processor can be a hardware-based integrated circuit (IC) and/or any other suitable processing device configured to run or execute a set of instructions and/or code stored, for example, in the memory. For example, the processor can be a general purpose processor, a central processing unit (CPU), an accelerated processing unit (APU), an application specific integrated circuit (ASIC), a network processor, a front end processor, a field programmable gate array (FPGA), a programmable logic array (PLA), and/or the like. The processor can be in communication with the memory (and any other component of the electronic device) via any suitable interconnection, system bus, circuit, and/or the like. The processor can include any number of engines, processing units, cores, etc. configured to execute code, instructions, modules, processes, and/or functions associated with the fluid transfer and/or rapid diagnostic testing systems and methods described herein.

In some embodiments, a communication interface can be any suitable hardware-based device in communication with the processor and the memory and/or any suitable software stored in the memory and executed by the processor. In some implementations, the communication interface can be configured to communicate with a network and/or any suitable device in communication with the network. The communication interface can include one or more wired and/or wireless interfaces, such as, for example, a network interface card (NIC), universal serial bus (USB) card, and/or any other suitable communication and/or peripheral card or device. For example, in some implementations, the NIC can include, for example, one or more Ethernet interfaces, optical carrier (OC) interfaces, asynchronous transfer mode (ATM) interfaces, one or more wireless radios (e.g., a WiFi® radio, a Bluetooth® radio, Near Field Communication (NFC) radios, etc.), and/or the like. In some implementations, the communication interface can be configured to send data to and/or receive data from (e.g., via one or more networks) any suitable portion or device included in the fluid transfer and/or assay devices and/or systems described herein, one or more peripheral components (e.g., a reader, scanner, camera, analyzer, detector, I/O device, etc.), a user or client device (e.g., a smartphone, a tablet, a wearable electronic device, a PC, etc.), and/or the like.

In some implementations, a network can be any type of network(s) such as, for example, a local area network (LAN), a wireless local area network (WLAN), a virtual network such as a virtual local area network (VLAN), a wide area network (WAN), a metropolitan area network (MAN), a worldwide interoperability for microwave access network (WiMAX), a telephone network (such as the Public Switched Telephone Network (PSTN) and/or a Public Land Mobile Network (PLMN)), an intranet, the Internet, an optical fiber (or fiber optic)-based network, a cellular network, and/or any other suitable network. Moreover, the network and/or one or more portions thereof can be implemented as a wired and/or wireless network. For example, the network can include one or more networks of any type such as, for example, a wired or wireless LAN and the Internet. In some implementations, the network can be any suitable combination of devices connected and/or otherwise placed in communication via a wired or wireless connection (e.g., a USB connection, an Ethernet connection, a WiFi network, a Bluetooth network, an NFC network, and/or the like).

In some embodiments, a user interface can be a display or screen such as, for example, a cathode ray tube (CRT) monitor, a liquid crystal display (LCD) monitor, a light emitting diode (LED) monitor, and/or the like. In some instances, the display can be a touch sensitive display or the like (e.g., the touch sensitive display of a smartphone, tablet, wearable device, PC, and/or the like). In some instances, the display can provide a user interface for a software application (e.g., a mobile application, a PC application, an internet web browser, and/or the like) that can allow the user to manipulate the electronic device(s). In some implementations, the user interface can include any suitable type of human-machine interface device, human-computer interface device, a batch interface, graphical user interface (GUI), and the like. In some implementations, the user interface can be any other suitable user interface and/or input/output (I/O) device(s) such as, for example, a holographic display, a wearable device such as a contact lens display, an optical head-mounted display, a virtual reality display, an augmented reality display, a mouse, a keyboard, and/or the like, or combinations thereof. Accordingly, the electronic device(s) described herein can receive, process, define, and/or store data such as, for example, one or more diagnostic test results, test standards against which to measure results data, predetermined and/or predefined treatment plans, patient profiles, disease profiles, etc. In addition, the electronic device(s) can present (e.g., on the display thereof) one or more qualitative and/or quantitative test results associated with any of the rapid diagnostic testing methods described herein (e.g., rapid diagnostic tests for sepsis and/or any other disease condition).

Some embodiments described herein relate to a computer storage product with a non-transitory computer-readable medium (e.g., memories or one or more memories) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for a specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, ROM devices, RAM devices, and/or Programmable Logic Devices (PLDs). Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a CPU, an FPGA, an ASIC, and/or the like. Software modules (executed on hardware) can be expressed in a variety of software languages (e.g., computer code), including C, C++, Java™, Ruby, Visual Basic™, Python™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, FORTRAN, etc.), functional programming languages (Haskell, Erlang, etc.), logical programming languages (e.g., Prolog), object-oriented programming languages (e.g., Java, C++, etc.) or other suitable programming languages and/or development tools, and/or combinations thereof (e.g., Python™). Additional examples of computer code include, but are not limited to, control signals, encrypted code, and compressed code.

What is claimed:

1. A system, comprising:

a fluid transfer device, the fluid transfer device including a housing forming an inlet configured to be placed in fluid communication with a bodily fluid source and an outlet configured to be placed in fluid communication with a sample reservoir, the housing including a sequestration chamber and a port in fluid communication with the sequestration chamber, the sequestration chamber configured to be placed in fluid communication with the inlet via a first flow path to receive a first volume of bodily fluid when the fluid transfer device is in a first state, the outlet configured to be placed in fluid communication with the inlet via a second flow path to receive a second volume of bodily fluid when the fluid transfer device is in a second state; and a flow-based assay device disposed in the housing between the inlet and the outlet, the flow-based assay device coupled to the port to receive a portion of the first volume of bodily fluid via a third flow path when the fluid transfer device is in a third state, the flow-based assay device configured to provide an indication associated with the presence of a target analyte in the portion of the first volume of bodily fluid.

2. The system of claim 1, wherein the third flow path is different from each of the first flow path and the second flow path.

3. The system of claim 1, wherein the first volume of bodily fluid is sequestered from the first flow path when the fluid transfer device is in the second state.

4. The system of claim 3, wherein the second volume of bodily fluid flows through the second flow path, thereby bypassing the sequestration chamber and the first volume of bodily fluid sequestered therein.

5. The system of claim 1, wherein the port is configured to transition from a closed state to an open state to place the fluid transfer device in the third state.

6. The system of claim 5, wherein the flow-based assay device is in fluid communication with the sequestration chamber when the port is in the open state.

7. The system of claim 1, wherein the flow-based assay device is one of a sandwich lateral flow assay device or a competitive lateral flow assay device.

8. The system of claim 1, wherein the bodily fluid is blood, the target analyte is a biomarker for detecting sepsis in the blood, the biomarker being one of procalcitonin or lactate.

9. The system of claim 8, wherein the flow-based assay device includes a conjugate element including a matrix of at least one of enzymes, antibodies, or aptamers.

10. The system of claim 9, wherein the matrix includes a combination of chitosan and trehalose configured to stabilize at least a portion of the matrix.

* * * * *